US006800458B1

(12) United States Patent
Nick et al.

(10) Patent No.: US 6,800,458 B1
(45) Date of Patent: Oct. 5, 2004

(54) MANGANESE SUPEROXIDE DISMUTASE REGULATORY ELEMENTS AND USES THEREOF

(75) Inventors: Harry S. Nick, Gainesville, FL (US); Richard Rogers, Gainesville, FL (US); John F. Valentine, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/856,766

(22) PCT Filed: Nov. 30, 1999

(86) PCT No.: PCT/US99/28331

§ 371 (c)(1),
(2), (4) Date: Aug. 28, 2001

(87) PCT Pub. No.: WO00/32801

PCT Pub. Date: Jun. 8, 2000

Related U.S. Application Data

(60) Provisional application No. 60/110,334, filed on Nov. 30, 1998.

(51) Int. Cl.[7] ........................ C12N 15/00; C12N 15/09; C12N 15/86; C07H 21/04; C12P 21/06

(52) U.S. Cl. .................... 435/69.2; 536/23.1; 536/23.2; 536/24.1; 435/69.1; 435/320.1; 435/325; 435/455

(58) Field of Search ............................... 435/320.1, 325, 435/455, 69.1; 536/23.1, 23.2, 24.1, 23.5

(56) References Cited

PUBLICATIONS

Akashi, M. et al. Irradiation increases manganese superoxide dismutase mRNA levels in human fibroblasts. Possible mechanisms for its accumulation. *J. Biol. Chem.* Jun. 30, 1995;270(26):15864–9.

Borrello, S. et al. Diethyldithiocarbamate treatment up regulates manganese superoxide dismu–tase gene expression in rat liver. *Biochem. Biophys. Res. Commun.* Mar. 27, 1996;220(3):546–52.

Church, S.L. Manganese superoxide dismutase: nucleotide and deduced amino acid sequence of a cDNA encoding a new human transcript. *Biochim. Biophys. Acta.* Oct. 23, 1990;1087(2):250–2.

Del Maestro, R. et al. Subcellular localization of superoxide dismutases, glutathione peroxidase and catalase in developing rat cerebral cortex. *Mech. Ageing Dev.* Apr. 1989;48(1):15–31.

DiSilvestre, D. et al. Structure and DNA Sequence of the Mouse MnSOD Gene. *Mammalian Genome.* Apr. 1995;6(4):281–4.

Dougall, W.C. et al. Manganese superoxide dismutase: a hepatic acute phase protein regulated by interleukin–6 and glucocorticoids. *Endocrinology.* Nov. 1991;129(5):2376–84.

Eastgate, J. et al. A role for manganese superoxide dismutase in radioprotection of hematopoietic stem cells by interleukin–1, *Blood.* Feb. 1, 1993;81(3):639–46.

Fujii J. et al. Phorbol ester induces manganese–superoxide dismutase in tumor necrosis factor–resistant cells. *J. Biol. Chem.* Dec. 5, 1991;266(34):23142–6.

Gwinner, W. et al. Regulation of manganese superoxide dismutase in glomerular epithelial cells: mechanisms for interleukin 1 induction. *Kidney Int.* Aug. 1995;48(2):354–62.

Harris, C.A. et al. Manganese superoxide dismutase is induced by IFN–gamma in multiple cell types. Synergistic induction by IFN–gamma and tumor necrosis factor or IL–1. *J. Immunol.* Jul. 1, 1991;147(1):149–54.

Ho, Y.–S. et al. Molecular Structure of a Functional Rat Gene for Manganese–containing Superoxide Dismutase. *American Journal of Respiratory Cell and Molecular Biology.* Mar. 1991;4(3):278–86.

Hurt, J. et al. Multiple mRNA species generated by alternate polyadenylation from the rat manganese superoxide dismutase gene. *Nucleic Acids Res.* Jun. 25, 1992;20(12):2985–90.

Imaizumi, S. et al. Liposome–entrapped superoxide dismutase ameliorates infarct volume in focal cerebral ischaemia. *Acta Neurochir. Suppl.* (Wien). 1990;51:236–8.

Imaizumi, S. et al. Liposome–entrapped superoxide dismutase reduces cerebral infarction in cerebral ischemia in rats. *Stroke.* Sep. 1990;21(9):1312–7.

Jones, P.L. et al. Tumor Necrosis Factor Alpha and Interleukin–1β Regulate the Murine Manganese Superoxide Dismutase Gene through a Complex Intronic Enhancer Involving C/EBP–β and NF–kB. *Molecular and Cellular Biology.* Dec. 1997;17(12):6970–81.

Kifle, Y. et al. Regulation of the manganese superoxide dismutase and inducible nitric oxide synthase gene in rat neuronal and glial cells. *J. Neurochem.* May 1996;66(5):2128–35.

Melov, S. et al. A novel neurological phenotype in mice lacking mitochondrial manganese superoxide dismutase. *Nat. Genet.* Feb. 1998;18(2):159–63.

(List continued on next page.)

*Primary Examiner*—Gerry Leffers
*Assistant Examiner*—Ramin Akhavan
(74) *Attorney, Agent, or Firm*—Lahive & Cockfield, LLP; Jane E. Remillard, Esq.; Jill A. Mello

(57) ABSTRACT

A novel transcriptional regulatory element which was isolated from the MnSOD gene and which exhibits promoter-enhancer activity is disclosed. The promoter-enhancer activity of the element is further modulated by inflammatory mediators to regulate transcription. Methods of using the promoter-enhancer element to regulate gene expression, and therapeutic uses involving the promoter-enhancer element are also described.

23 Claims, 23 Drawing Sheets

PUBLICATIONS

Suzuki, K. et al. Manganese–superoxide dismutase in endothelial cells: localization and mechanism of induction. *Am. J. Physiol.* Oct. 1993;265(4 Pt 2):H1173–8.

Tannahill, C.L. et al. Induction and immunolocalization of manganese superoxide dismutase in acute acetic acid–induced colitis in the rat. *Gastroenterology.* Sep. 1995;109(3):800–11.

Valentine, J.F. et al. Mesalamine (5–ASA) Induction of Manganese Superoxide Dismutase: A New Mechanism of 5–ASA Action. *Gastroenterology*. Mar. 14–17, 1995;108(4 Suppl.):A933 (Abstract).

Valentine, J.F. et al. Acute-phase induction of mangansese superoxide dismutase in intestinal epithelical cell lines. *Gastroenterology.* Sep. 1992;103(3):905–12.

Valentine, J.F. et al. Colitis and interleukin 1β up–regulate inducible nitric oxide synthase and superoxide dismutase in rat myenteric neurons. *Gastroenterology.* Jul. 1996;111(1):56–64.

Visner, G.A. et al. Regulation of manganese superoxide dismutase: IL–1 and TNF induction in pulmonary artery and microvascular endothelial cells. *Biochem. Biophys. Res. Commun.* Oct. 15, 1992;188(1):453–62.

Visner, G.A. et al. Regulation of manganese superoxide dismutase in porcine pulmonary artery endothelial cells. *Am. J. Physiol.* Jun. 1991;260(6 Pt 1):L444–9.

Visner, G.A. et al. Regulation of manganese superoxide dismutase by lipopolysaccharide, interleukin–1, and tumor necrosis factor. Role in the acute inflammatory response. *J. Biol. Chem.* Feb. 15, 1990;265(5):2856–64.

Wan, X.S. et al. Molecular Structure and Organization of the Human Manganese Superoxide Dismutase Gene. *DNA and Cell Biology.* Nov. 1994;13(11):1127–36.

Warner, B.B. et al. Redox regulation of manganese superoxide dismutase. *Am. J. Physiol.* Jul. 1996;271(1 Pt 1):L150–8.

Wispe, J.R. et al. Human Mn–superoxide dismutase in pulmonary epithelial cells of transgenic mice confers protection from oxygen injury. *J. Biol. Chem.* Nov. 25, 1992;267(33):23937–41.

Wong, G.H.W. et al. Manganous superoxide dismutase is essential for cellular resistance to cytotoxicity of tumor necrosis factor. *Cell.* Sep. 8, 1989;58(5):923–31.

Xu, Y. et al. An Intronic NF–kB Element Is Essential for Induction of the Human Manganese Superoxide Dismutase Gene by Tumor Nectoris Factor–α and Interleukin–1β. *DNA and Cell Biology.* Sep. 1999;18(9):709–22.

Yeh, C.–C. et al. Transcriptional Regulation of the 5' Proximal Promoter of the Human Manganese Superoxide Dismutase Gene. *DNA and Cell Biology.* Nov. 1998;17(11):921–30.

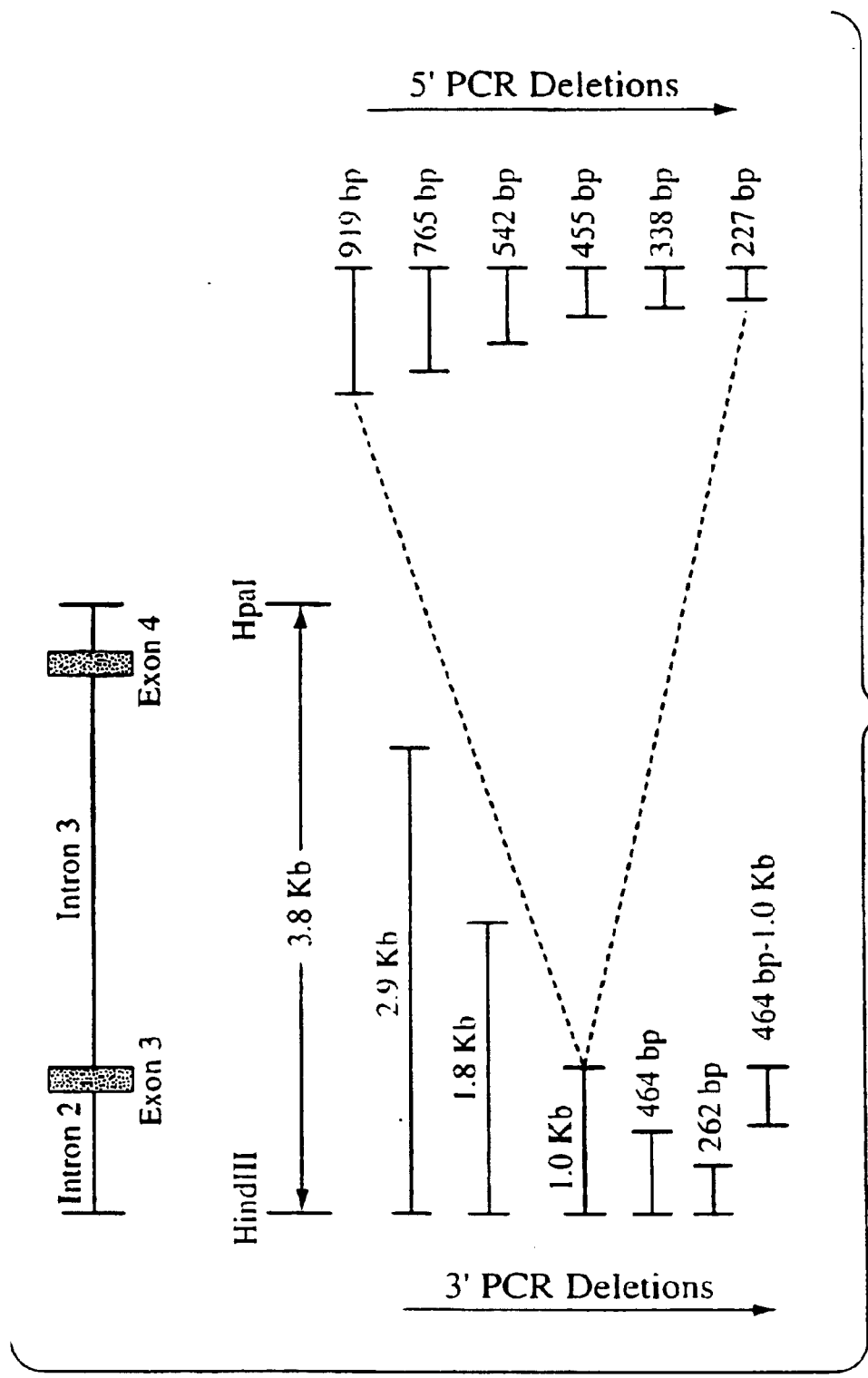

```
RAT   4190  GGGGCATCTAGTGGAGAAGTGTGGTATTTTAGCATAGTTGTGTAAGTGGCCCAACCAAGAG
             ||||||||||||||||||| ||  ||||||||||  |||||||| | ||||  ||| ||
HUM   2577  GAGGCATCTAGTGGAAAAATGCAGTATTTCAGCCTGATTGTGTTTGAAGTAAATGATTAAAAGAG
                                                          4231

RAT   4251  AAGGAAATTACCACATTCTCTGGAAATTTACTTGCAATAAGCAAATCACATAATCGTGAATACGGGAAGAGACTC
             |||||| ||||||||||||||||||| ||||||| ||||| ||||   ||||| |||||||||||||||||
HUM   2657  GAGGAAGTTACCACATTCTCTGGAAGATTTACTTGAGACAGATGAACCTTGAATTACGGGAAAAGGCCCCG
                                                          4374

RAT   4325  TGATTTAGGAAATGACAGATTTGGGAAGGCTGTGTGGTAATAGTGAGTAGGGGAAAAGCCCCAGTTGGGAAATCG
             |||||||||||| |||| ||||||||  ||   |||||| | ||||  ||||||||| || ||||||||||
HUM   2711  TGATTTAGGAAATAACAAATTTGGGAAAACATGTAATGGGAGAGACTGGGAATACCCCAGTTGTGAAAGTA
                                                          4348

RAT   4397  TTTCCCTCTAAGGTGACATCTGACAACTTTCCTCTTAAATGTGTAAAAACATGGT
             ||||| ||||||||||||||||||| |||||||  ||  ||  ||
HUM   2783  CTTCCTGTAAGGCAACATCTGACACCAGGAACCTTTCTCTTCAGTATTTAAAA

RAT   4451  GATTTCAACCCTTCCGTGGAGACAGAGCTGTATTTGTTAGTGAATGCTG
             ||   |||||||||  | ||| |||||||| |||  || |||||| ||
HUM   2837  ACAACTTAATTTCAGTCCTTACTTGTGGAATCAGAGCCTTACTTATGTAA
                                                          4491
```

Fig. 5

Cellular and Stimulus-Specific Responses of the MnSOD Gene

| CELL TYPES | LPS | IL-1β | TNF-α | IL-6 | PHORBOL ESTER | IFN-γ | GLUCOCORTICOI | ENHANCER RESPONSE TO LPS IL-1 AND TNF |
|---|---|---|---|---|---|---|---|---|
| Pulmonary Epithelial | ⇈⇈⇈ | ⇈⇈⇈ | ⇈⇈⇈ | − | ⇈⇈ | − | ⇊⇊ | X |
| Pulmonary Microvascular Endothelial | ⇈⇈⇈ | ⇈⇈⇈ | ⇈⇈⇈ | − | ⇈⇈ | − | ⇊⇊ | X |
| Pulmonary Fibroblasts | ⇈⇈ | ⇈⇈ | ⇈⇈ | ND | ND | ND | ND | X |
| Pulmonary Artery Endothelial | ⇈⇈⇈ | ⇈⇈⇈ | ⇈⇈⇈ | − | ND | − | ⇊⇊ | X |
| Small Intestinal Epithelial | ⇈⇈⇈ | ⇈⇈⇈ | ⇈⇈⇈ | − | ND | − | ⇊⇊ | X |
| Small Intestinal Smooth Muscle | ⇈⇈⇈ | ⇈⇈⇈ | ⇈⇈⇈ | ND | ND | ND | ND | ND |
| Myenteric Neurons | − | − | − | ⇈⇈⇈ | ND | ND | ⇊⇊ | ND |
| Hepatocytes | − | − | − | ⇈⇈⇈ | ND | ND | ND | ND |
| Hepatoma | ⇈⇈⇈ | ⇈⇈⇈ | ⇈⇈ | ND | ⇈⇈ | − | ⇊⇊ | ND |
| Glomerular Epithelial | ⇈⇈⇈ | ⇈⇈⇈ | ⇈⇈⇈ | ND | ND | ⇈⇈⇈ | ⇊⇊ | ND |
| Mesangial | ⇈⇈⇈ | ⇈⇈⇈ | ⇈⇈⇈ | ND | ND | ⇈⇈⇈ | ⇊⇊ | ND |
| Primary Neuronal | ⇈⇈⇈ | ⇈⇈⇈ | ⇈⇈⇈ | − | ND | − | ND | ND |
| Primary Glial | ⇈⇈⇈ | ⇈⇈⇈ | ⇈⇈⇈ | ND | ND | ⇈⇈⇈ | ND | X |

⇈⇈⇈ 15-20 Fold Induction    ⇈⇈ 5-10 Fold Induction    ⇊⇊ 75-80% Inhibition    ND No Data

Fig. 12

SEQUENCE LISTING

<160> NUMBER OF SEQ ID NOS: 5

<210> SEQ ID NO 1
<211> LENGTH: 554
<212> TYPE: DNA
<213> ORGANISM: Rattus norvegicus

<400> SEQUENCE: 1

```
ctcttattgc ctctcaggtc tgggaaacgg gttgagtaat tggttcactg ggggcatcta    60
gtggagaagt gtggtatttt agcatagttg tgtaagtggc ccaaccaaga gaaggaaatt   120
accacattct ggaaatttta cttgcaataa gcaaatcaca taatcgtgaa tacgggaaga   180
gactctgatt taggaaatga cagatttggg aaggctgtgg taatagtgag taggggaaaa   240
gcccagttgg gaaatcgttt cctctaaggt gacatctgac aactttcctc ttaatgttgt   300
aaaaacatgg tgatttcaac ccttccgtgg agacagagct gtatttgttt agtgaatgct   360
gctgggaata agaaagccgt ggttttattg acctggctga ggatggattt tgaaaaggtg   420
tttacgtttt atatttcagg agatgttaca actcaggttg ctcttcagcc tgcactgaag   480
ttcaatggcg ggggccatat caatcacagc attttctgga caaacctgag ccctaagggt   540
ggtggagaac ccaa                                                     554
```

<210> SEQ ID NO 2
<211> LENGTH: 466
<212> TYPE: DNA
<213> ORGANISM: Homo sapiens

<400> SEQUENCE: 2

```
cgttagtggt ttgcacaagg aagataatcg atagtcatgt tttttagacg ctctgtattg    60
cttggtaagc tacgtagtaa aaaatgttta cttttcctta aatgttttga atttcggggt   120
tatgaaattt gttgagtaat ttttagacag tcacatcttg ttgactggag gcatctagtg   180
gaaaaatgca gtatttcagc ctgattgtgt ttgaagtaaa tgattaaaag aggaggaagt   240
taccacattc tggaagattt acttgagaca gacgaacctt gaattacggg aaaaggcccc   300
gtgatttagg aaataacaaa tttgggaaac atgtaatggg gagagactgg ggaatacccc   360
agttgtgaaa gtacttcctg taaggcaaca tctgacacca ggaacctttc tcttcagtat   420
tttaaaaaca acttaatttc agtcctttac ttgtggaatc agagcc                  466
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primers

<400> SEQUENCE: 3

```
cgttagtggt ttgcacaagg aagataatcg                                    30
```

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primers

```
<400> SEQUENCE: 4
ggctctgatt ccacaagtaa aggactg                                    27

<210> SEQ ID NO 5
<211> LENGTH: 261
<212> TYPE: DNA
<213> ORGANISM: Rattus norvegicus

<400> SEQUENCE: 5
gtaagtggcc caaccaagag aaggaaatta ccacattctg gaaattttac ttgcaataag    60
caaatcacat aatcgtgaat acgggaagag actctgattt aggaaatgac agatttggga   120
aggctgtggt aatagtgagt agggaaaag cccagttggg aaatcgtttc ctctaaggtg   180
acatctgaca actttcctct taatgttgta aaaacatggt gatttcaacc cttccgtgga   240
gacagagctg tatttgttta g                                           261
```

MANGANESE SUPEROXIDE DISMUTASE REGULATORY ELEMENTS AND USES THEREOF

This application claims priority to U.S. Provisional Application No. 60/110,334, filed Nov. 30, 1998.

GOVERNMENT FUNDING

This invention was made with government support under grant HL-39593 a warded by the National Institutes of Health. The United States government has certain rights in the invention.

FIELD OF THE INVENTION

The invention relates to novel transcriptional regulatory elements derived from manganese superoxide dismutase (MnSOD) genes, as well as methods of identifying and using the regulatory elements to control gene expression.

BACKGROUND OF THE INVENTION

Precise control of regulated gene expression has multiple potential applications including inducible gene targeting, overexpression of cytotoxic or cytoprotective genes, antisense RNA expression, and somatic gene therapy (Wettstein et al., 1988).

The ability to produce biologically active polypeptides is increasingly important to the pharmaceutical industry. Over the last decade, advances in biotechnology have led to the production of important proteins and factors from bacteria, yeast, insect cells and from mammalian cell culture. Mammalian cultures have advantages over cultures derived from the less advanced life forms in their ability to post-translationally process complex protein structures such as disulfide-dependent folding and glycosylation. Neuroendocrine cell types have added unique capacities of endoproteolytic cleaving, C-terminal amidation and regulated secretion. Indeed, mammalian cell culture is now a preferred source of a number of important proteins for use in human and animal medicine, especially those which are relatively large, complex or glycosylated. Improved methods for expressing desirable polypeptides in mammalian host cells are highly desirable.

Gene therapy involves the transfer of one or more functional homologous genes, and the sequences controlling their expression, into a target cell. The purpose of gene therapy is to replace a defective or deficient gene, the absence of which produces a pathological state or to supplement an endogenous gene product to achieve a therapeutic effect (Berns and Giraud, 1995). Viral vectors are widely used vehicles for the effective delivery of genes into mammalian cells which have the capability to infect high proportions of cells in a cell population (Friedmann and Yee, 1995; Friedmann, 1997). Some of the best examples of viral gene targeting vectors are based on retroviral, adeno (Ad) or adeno-associated (AAV) viruses. However, vectors developed from these viruses all lack some level of specificity which presents an obstacle for appropriate and controlled expression of foreign genes (Friedmann, 1996). For example, retroviruses are generally limited to transduction of dividing cells whereas Ad and AAV can transduce non-dividing cells. On the other hand, repeated administration of recombinant Ad based vectors, is often limited by host immune responses against viral structural proteins. Presently, AAV may hold the greatest promise in that rAAV does not appear to induce an inflammatory or immune response, and is only limited by the inability to easily produce high rAAV virion titers.

AAV is a single stranded human DNA virus with a genome length of 4.7 kb (Muzyczka, 1992; Srivastava et al., 1983; Yang and Trempe, 1993) that requires a helper virus for productive growth. Adeno (Ad) or herpes virus family members can provide helper function in established human tissue culture lines, whereas only adenovirus is found associated with AAV in human isolates. The normal route of infection for AAV is via the respiratory or intestinal tracts analogous to Ad. If a helper virus is not available during AAV infection, the AAV genome integrates into a human chromosome 19 and is propagated as a stable provirus. Superinfection with Ad leads to AAV provirus excision and a normal productive growth cycle that results in the production of a mixed viral stock consisting of both wild type AAV and Ad virus particles. AAV possesses unique biological properties, which has led to its exploitation as a versatile gene therapy vector. Most notably AAV undergoes a latency phase, which often involves stable integration within a region of chromosome 19 known as the AAVS1 site, thus establishing a persistent infection with very little host response (Cheung et al., 1980; Conrad et al., 1996). Perhaps the most attractive AAV feature is that even though human exposure to this virus is commonplace, no diseases has been associated with AAV infections in either animal or human populations (Blacklow et al., 1967; Blacklow et al., 1968, Blacklow et al., 1971; Hoggan, 1970), nor have there been any reports of rAAV induced inflammatory responses. In addition, it has been demonstrated that recombinant AAV (rAAV) vectors do not integrate in lung epithelial cells (Flotte et al., 1993; Afione et al., 1996), rAAV persists for up to six months potentially as an unintegrated episome.

Numerous AAV vectors have been developed to exploit the latency pathway, where, in general, vectors are generated by deleting the viral coding sequences and substituting the appropriate transgene controlled by a promoter and flanked by the AAV-TRs. By keeping the construct size at ~5 kb which is within the packaging limit, these vectors can be incorporated into infectious virions in trans in Ad-infected cells. Such recombinant virions have been found to infect a variety of cell types in vitro and in vivo including hematopoietic cells (Goodman et al., 1994) neurons (Kaplitt et al., 1994), airway epithelial cells (Flotte et al., 1992), as well as skeletal and cardiac muscle (Kessler et al., 1996).

One of the main issues in potential clinical application of gene therapy is the need for increased gene transfer efficiency and target specificity associated with regulated expression at therapeutically relevant levels in vivo (Chow et al., 1997). Effective gene therapy, therefore, must include the design of crucial regulatory elements, promoters and enhancers, which possess cell type specific activities and can be activated by certain physiologically relevant induction factors (e.g., hormones, cytokines, chemokines, irradiation, heat shock) via responsive elements. Controlled and restricted expression can be achieved using such regulatory elements to drive the expression of therapeutic genes in plasmid based as well as viral vector constructs (Hwang et al., 1997; Sandig and Strauss, 1996; Finke et al., 1998). In addition to high level and efficient gene expression, minimizing or excluding inappropriate gene expression in surrounding non-target cells will be of great importance for numerous gene therapy applications (Namba et al., 1998; Hesdorffer et al., 1998; Gossen and Bujard, 1992).

Unfortunately, almost all of the presently available inducible promoters used in gene therapy vectors require exogenous stimulation by non-physiological or artificial substances such as tetracycline (No et al., 1996), ecdysone (Delort and Capecchi, 1996), or RU486 (Massie et al., 1998). One of the disadvantages of these systems is that they all require expression of two gene products. Namely, the expression of the desired transgene driven by an inducible promoter which requires the expression of a non-endogenous receptor. This is usually accomplished by co-transfection of separate plasmids into mammalian cells, thus potentially limiting the size of the transgene when a viral vector system is used for transgene delivery. In addition, to maintain high levels of expression with the aforementioned inducible promoters, the exogenous substance must be continuously supplied. The disadvantages of these systems include the continuous treatment with the exogenous substance and slow clearance from the organism, which interferes with quick and precise induction. Alternatively high levels of constitutive expression can be obtained with the cytomegalovirus (CMV) promoter in many cell types, which will be beneficial in certain disease states, where an example might be the CFTR gene product for cystic fibrosis.

It has been suggested that the enhancer elements of mammalian genes might allow the desired precise control of gene regulation needed for transgene expression (Maxwell et al., 1996; Clesham et al., 1996; Walther and Stein, 1996; Hofmann et al., 1996; Raoul et al., 1998). Such an enhancer element should be tissue-specific and stimulant-specific, allowing the transgene expression to be kept at a low basal level. However, such an element should allow dramatic induction in response to the precise stimulus. Ideally, the stimulus causing this induction could be endogenously produced and potentially associated with the disease pathology. Most intracellular trans-activators of enhancer elements are typically stimulated as part of signal transduction pathways from transmembrane or intracellular receptors responding to extracellular ligands (hormones, cytokines, chemokines). Therefore, unlike the presently available inducible promoters systems, an ideal regulatory sequence would function through an endogenous stimulus, receptor and signal transduction pathway.

Many diseases amenable to gene therapy will not require continuous high constitutive gene expression since the disease state itself is episodic in nature (inflammatory or ischemic diseases). In these situations, low levels of gene expression during the normal state are adequate, but the capacity to increase expression during the onset of inflammation or ischemia would be advantageous for the precise control sought. High level expression of cytoprotective proteins (such as MnSOD. Hohmeier et al., 1998; Majima et al., 1998; Epperly et al., 1998) during inflammation/ischemia of various organ systems (lungs, brain, small and large intestine) would either halt or slow progression of the disease process (Waxman et al., 1998; Manna et al., 1998; Arai et al., 1990). However, available inducible promoters do not allow the cell to control the timing of expression of the transgene or its fold induction. An ideal inducible element would make use of the cell or tissues own signaling system to increase expression of the transgene of interest. Under conditions of inflammation, the most precise inducible element would probably utilize the cytokine systems.

BRIEF DESCRIPTION OF THE DRAWINGS

FIG. 3A shows a schematic representation of serial deletions of the 3.8 Kb internal enhancer fragment of the rate MnSOD gene.

FIG. 5 shows an alignment of the rat MnSOD enhancer region (SEQ ID NO:3) with the analogous region of intron 2 (SEQ ID NO:2) of the human MnSOD gene.

FIG. 12 shows regulation of the MnSOD gene by inflammatory mediators in various cell types.

SUMMARY OF THE INVENTION

Figure 1A:
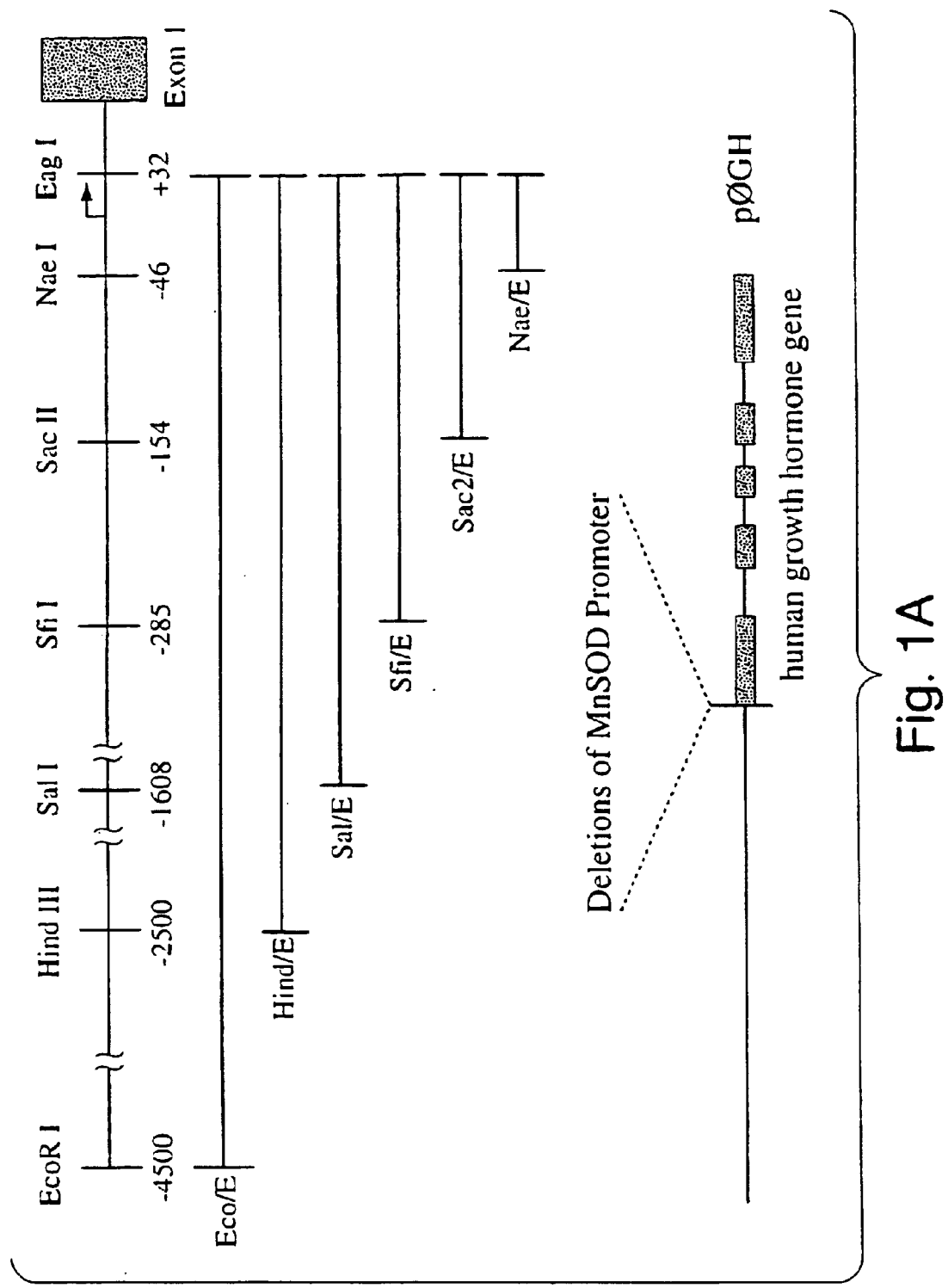
FIG. 1A shows a schematic representation of the promoter deletions of the 5' flanking sequence of the rat MnSOD gene. The first exon is depicted by a box, and numbers indicate the position of the restriction enzyme sites relative to the first ATG signal. Placement of the deletion fragments 5' to the human growth hormone reporter gene in the promoter less human growth hormone vector (pØGH) is indicated.

In one aspect, the invention provides an isolated polynucleotide comprising a manganese superoxide dismutase (MnSOD) regulatory element capable of causing inducible transcription or expression of an operably linked heterologous polynucleotide. In one embodiment, the regulatory element is derived from intron 2 of the rat MnSOD gene and, in particular, the region of intron 2 having the nucleotide sequence shown in SEQ ID NO:1. In a specific embodiment, the regulatory element comprises the 260 nucleotides from SEQ ID NO:1 shown in SEQ ID NO:5. In another embodiment, the element is derived from intron 2 of the human MnSOD gene and, in particular, the region of intron 2 having the nucleotide sequence shown in SEQ ID NO:2.

The invention also encompasses highly homologous (e.g., having at least about 60% sequence identity) regulatory elements from other mammalian MnSOD genes which also are capable of causing inducible transcription or expression of an operably linked heterologous polynucleotide. In particular embodiments, the invention encompasses an MnSOD regulatory element comprising a nucleotide sequence which is at least about 70% identical to SEQ ID NO:1 or at least about 90% identical to SEQ ID NO:2.

In another aspect the invention provides an isolated manganese superoxide dismutase regulatory element operably linked to a heterologous polynucleotide such that, upon activation of the regulatory element, transcription or expression of the heterologous polynucleotide is induced. In one embodiment, the regulatory element is activated (i.e., induces transcription or expression of an operatively linked heterologous polynucleotide) in the presence of an inflammatory stimulus, such as TNF-α, IL-1β or LPS. In another embodiment, the regulatory element is activated in the presence of 5-aminosalicylic acid.

The heterologous polynucleotide can be any polynucleotide capable of being transcribed or expressed such as a gene encoding a protein or polypeptide (e.g., a cytoprotectant) or a polynucleotide which is transcribed as an antisense mRNA. The invention also provides a cell (e.g., a mammalian cell) transformed either in vivo or in vitro with an isolated MnSOD regulatory element of the invention. In another aspect, the invention provides an inducible expression system comprising (a) an isolated MnSOD regulatory element of the invention which induces transcription or expression of an operably linked heterologous polynucleotide upon activation; and (b) a compound which activates the regulatory element, or a polynucleotide encoding a compound which activates the regulatory element.

The inducible expression system can also include a heterologous polynucleotide operably linked to the MnSOD regulatory element such that, upon activation of the MnSOD regulatory element by the compound, transcription or expression of the heterologous polynucleotide is induced. The inducible expression system can further include a heterologous promoter (i.e., a promoter which is not derived from the MnSOD regulatory element itself) to further increase transcription/expression, levels of the heterologous polynucleotide.

Accordingly, in yet another aspect, the invention provides a method for achieving inducible transcription or expression of a heterologous polynucleotide in a cell by introducing the above-described MnSOD regulatory element or expression system into a cell under conditions suitable for transcription and/or expression of a heterologous polynucleotide. The method can further include the step of introducing into the cell an effective amount of a compound which activates the regulatory element to induce transcription or expression of an operatively linked polynucleotide, or a polynucleotide encoding the compound.

Other aspects and embodiments of the invention shall be apparent from the following detailed description.

DETAILED DESCRIPTION OF THE INVENTION

The present invention is based on the identification and isolation of a novel inducible MnSOD transcriptional regulatory element having dual promoter-enhancer ("prohancer") functions. The inducible prohancer element can be regulated by inflammatory mediators, (e.g., lipopolysaccharide (LPS), tumor necrosis factor alpha (TNF-α), interleukin-1 beta (IL-1β)), as well as other compounds, for the control of gene expression.

Definitions

Before further description of the invention, certain terms employed in the specification, examples, and appended claims are defined below.

An "isolated polynucleotide" or "isolated nucleic acid molecule" refers to a polynucleotide (e.g., DNA, RNA) which is removed from its natural sequence context. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. The isolated polynucleotide can be any polynucleotide that is capable of being transcribed or translated in a cell. The isolated polynucleotide (genomic or cDNA clone) can be, for example, cloned into a vector. Except as noted hereinafter, standard techniques for cloning, DNA isolation, amplification and purification, for enzymatic reactions involving DNA ligase, polymerase, restriction endonucleases and the like and various separation techniques are those known and commonly employed by those skilled in the art. A number of standard techniques are described in: Maniatis et al. (1982) Molecular Cloning, Cold Spring Harbor Laboratory, Cold Spring Harbor, N.Y.; Wu (ed.)(1979) Meth. Enzymol 68; Wu et al. (Eds.) (1983) Meth. Enzymol. 100 & 101; Grossman and Moldave (eds.) (1980) Meth. Enzymol. 65; Miller (ed) (1972) Exp. Mol. Genetics, Cold Spring Harbor, N.Y.; Old and Primrose (1981) Principles of Gene Manipulation, Univ. of Cal. Press, Berkeley; Schlief and Wensink (1982) Practical Methods in Molecular Biology; Glover (ed) 1985 (DNA Cloning, Vols. I and II, IRL Press, Oxford, UK; Sellow and Hollaender (1979) Genetic Engineering: Principles and Methods, Vols I, Plenum Press, N.Y,: which are incorporated by reference in their entirety herein. Abbreviations, where employed, are those deemed standard in the field and commonly used in professional journals such as those cited herein.

As used herein, the term "nucleic acid molecule" or "polynucleotide" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "derived from", as used herein, refers to an actual or theoretical source or origin for isolated polynucleotides of the invention. For example, a polynucleotide that is "derived from" a particular polynucleotide (e.g., a MnSOD gene) will be identical or highly homologous in nucleotide sequence to a relevant portion of the reference polynucleotide (e.g., a MnSOD gene). Thus, for example, a polynucleotide that is "derived from" the intronic sequences (e.g., intron 2) of a MnSOD gene may correspond in nucleotide sequence to all or a portion of the intronic sequences of a wild-type MnSOD gene. Isolated polynucleotides of the invention which are "derived from" MnSOD genes (e.g., intron 2) also include those which have been modified by insertion, deletion or substitution of one or more nucleotides but which retain substantially the same activity or function.

A DNA "coding sequence", "coding region", or a "sequence encoding" a particular protein is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, cDNA from eukaryotic mRNA, genomic DNA sequences from eukaryotic (e.g., mammalian, animal, avian, etc.) or prokaryotic sources, as well as synthetic DNA sequences. A transcription termination sequence will usually be located 3' to the coding sequence.

A "MnSOD gene", as used herein, refers to a MnSOD gene (e.g., a cloned genomic gene or a cDNA), including its untranscribed upstream and downstream regions and transcribed, untranslated regions from any species which naturally expresses MnSOD. The nucleotide sequence for the genomic human MnSOD gene is available at GenBank Accession No. S77127. A "nonhuman MnSOD gene", as used herein, refers to a MnSOD gene (e.g., a cloned genomic gene or a cDNA), including its untranslated regulatory regions, from any species excepting human (e.g., rat, mouse, avian, sheep, porcine, bovine). For example, the nucleotide sequence for the rat MnSOD is available at GenBank Accession No. X56600.

The terms "regulatory element", "control element" and "regulatory sequence" are used interchangeably herein, and refer to a nucleic acid which, when operably linked to a polynucleotide, modulates transcription and/or expression levels of the polynucleotide in a cell. Genetic regulatory elements of the present invention may include promoters, enhancers, or a combination thereof, as well as other cis-acting sequences involved in the binding of transcription factors. Regulatory elements include both positive and negative regulators of transcription.

The term "promoter", as used herein, refers to a DNA sequence which is generally placed adjacent to the 5' end of a structural gene, located proximal to the start codon, that is involved in the initiation of transcription of the adjacent gene. Promoters contain DNA sequence elements that mediate the binding of an RNA polymerase, and modulate the level of transcription. Further, specific regulatory sequences within or adjacent to promoters that are functional in the regulation (induction and repression) of gene expression responsive to stimuli or specific chemical species may also be present. If a promoter is "inducible", then the rate of transcription increases in response to an inducing agent or "inducer".

The term "enhancer", as used herein, refers to a regulatory sequence, which can function in either orientation and in any location with respect to a promoter, to modulate (e.g., increase) the effect of a promoter (e.g., to increase transcription levels). For example, an enhancer of the present invention may act in a position-independent and an orientation-independent manner to induce transcription of an operatively linked polynucleotide.

The terms "promoter-enhancer" or "prohancer" are used interchangeably herein and refer to an inducible regulatory element capable of initiating transcription and/or expression of a polynucleotide sequence to which it is operatively linked. A prohancer element can act independently of a classical promoter to initiate and regulate transcription when it is operatively linked upstream (e.g., 5') of a gene, thus acting as a promoter. A prohancer element can also function as an enhancer, acting in a position and orientation independent fashion in conjunction with a promoter (e.g., herpes virus TK promoter) to regulate inducible gene transcription (e.g., under conditions of inflammation).

The terms "inducible transcription" or "induction of transcription" are used interchangeably herein, and refer to the initiation of transcription by interaction of an "inducer" with a transcriptional regulatory protein and/or element. An "inducer" includes, but is not limited to, any protein, polypeptide, nucleic acid, carbohydrate, small molecule, or stimulus that, either directly or indirectly, triggers gene transcription by binding to a transcriptional regulatory protein and/or, element. For example, gene expression is regulated by factors such as environmental factors (e.g., temperature, light, and oxygen tension), chemical species (e.g., nutrients, metabolites, heavy metal ions), cytokines and steroids. The exact mechanism of regulation by such signals or stimuli is likely to be complex, involving multiple protein interactions. By analogy to previous mechanistic studies of transcriptional regulation, however, regulatory control is expected to involve changing the ability of RNA polymerase to bind to DNA sequences in the promoter region. Suitable inducers of MnSOD prohancer elements of the invention include inflammatory mediatiors (e.g., LPS, TNF-α and IL-1β) and benzene derivatives, e.g., 5-aminosalicylic acid.

"Expression" of a gene requires both transcription of DNA into mRNA, and the subsequent translation of the mRNA into protein products.

As used herein, the term "heterologous" is defined in relation to a predetermined reference polynucleotide sequence, and includes any non-identical polynucleotide, or any polynucleotide that does not naturally occur adjacent to the reference sequence. For example, with respect to a reference promoter sequence, a heterologous polynucleotide includes any polynucleotide that is not identical to the promoter to which it is operatively linked.

The term "operatively linked" or "operably linked" is intended to mean that molecules are functionally coupled to each other in that the change of activity or state of one molecule is affected by the activity or state of the other molecule. Nucleotide sequences are "operably linked" when a transcriptional regulatory sequence functionally relates to the DNA sequence encoding the polypeptide, protein, or antisense mRNA of interest. For example, a promoter nucleotide sequence is operably linked to a DNA sequence encoding a protein, polypeptide, or antisense mRNA of interest if the promoter nucleotide sequence controls the transcription of the DNA sequence encoding the protein or mRNA of interest. Typically, two polypeptides that are operatively linked are covalently attached through peptide bonds.

The term "reporter gene", as used herein, refers to a gene encoding a protein which is readily quantifiable or observable. Because gene regulation usually occurs at the level of transcription, transcriptional regulation and promoter activity are often assayed by quantitation of gene products. For example, promoter regulation and activity has often been quantitatively studied by the fusion of the easily assayable $E.$ $coli$ lacZ gene to heterologous promoters (Casadaban and Cohen (1980) J. Mol. Biol. 138:179–207). The structural gene for chloramphenicol acetyl transferase (CAT), human growth hormone (hGH), and green fluorescence protein (GFP) are other genes commonly used to detect activity of a promoter or other regulatory sequence.

A "vector" is a replicon, such as a plasmid, phage, or cosmid, to which another DNA segment may be attached so as to bring about the replication of the attached segment. As used herein, the term vector is intended to include a nucleic acid molecule capable of transporting another nucleic acid to which it has been linked. A vector may be characterized by one or a small number of restriction endonuclease sites at which such DNA sequences may be cut in a determinable fashion without the loss of an essential biological function of the vector, and into which a DNA fragment may be spliced in order to bring about its replication and cloning. A vector may further contain a marker suitable for use in the identification of cells transformed with the vector. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. However, the invention is intended to include other forms of expression vectors, such as viral vectors (e.g., replication defective retroviruses, adenoviruses and adeno-associated viruses), which serve equivalent functions.

An "expression vector" means any DNA vector (e.g., a plasmid vector) containing the necessary genetic elements for expression of a desired gene, including a promoter region of the present invention. These elements are "operably linked" to the gene, meaning that they are located at a position within the vector which enables them to have a functional effect on transcription of the gene. The regulatory elements need not be contiguous with the coding sequence, so long as they function to direct the expression thereof. Thus, for example, intervening untranslated yet transcribed sequences can be present between a promoter and the coding sequence and the promoter can still be considered "operably linked" or "in operable linkage to" the coding sequence.

A cell has been "transformed" by exogenous DNA (e.g., a transgene) when such exogenous DNA has been introduced inside the cell membrane. Exogenous DNA may or may not be integrated into the chromosomal DNA comprising the genome of the cell. With respect to eukaryotic cells, a stably transformed cell is one in which the exogenous DNA has become integrated into the chromosome such that it is inherited by daughter cells though chromosome replication.

A "cell" or "host cell" of the invention includes any cell that can be modified by the introduction of heterologous DNA. A host cell of the present invention includes prokaryotic cells and eukaryotic cells. Prokaryotes include gram negative or gram positive organisms, for example, $E.$ $Coli$ or Bacilli. Suitable prokaryotic host cells for transformation include, for example, *E. coli, Bacillus subtilis, Salmonella typhimurium*, and various other species within the genera Pseudomonas, Streptomyces, and Staphylococcus. Eukaryotic cells include, but are not limited to, yeast cells, plant cells, fungal cells, insect cells (e.g., baculovirus), mammalian cells, and the cells of parasitic organisms, e.g., trypanosomes.

As used herein, the term "yeast" includes not only yeast in a strict taxonomic sense, i.e., unicellular organisms, but also yeast-like multicellular fungi of filamentous fungi. Exemplary species include *Kluyverei lactis, Schizosaccharomyces pombe, Ustilaqo maydis*, and *Saccharomyces cerevisiae*. Other yeast which can be used in practicing the present invention are *Neurospora crassa, Aspergillus niger, Aspergillus nidulans, Pichia pastoris, Candida tropicalis*, and *Hansenula polymorpha*.

Mammalian host cell culture systems include established cell lines such as COS cells, L cells, 3T3 cells, Chinese hamster ovary (CHO) cells, embryonic stem cells, and HeLa cells.

A "transgene" refers to a nucleic acid which is introduced into a cell. Typically, the transgene is integrated into the genome of the cell by gene targeting or homologous recombination. The transgene can encode a protein which is not expressed in the cell or which is expressed in the cell at low levels or in defective form.

A "transgenic animal" is an animal carrying in its cells at least one transgene which has been introduced into the germline of the animal, such that the introduced gene is present in all somatic and germline cells. A transgenic animal can contain a transgene that is either homologously or non-homologously integrated into an endogenous chromosomal location (Hogan et al (1994) Manipulating the Mouse Embryo, Cold Spring Harbor Laboratory, Cold Spring Harbor, N.Y.).

I. MnSOD Prohancer Elements

Novel MnSOD transcriptional regulatory elements or "prohancers" of the invention can act as a promoter and/or an enhancer when operatively to a heterologous polynucleotide sequence. In the absence of stimulus, negligible levels of transcription occur, but transcription is significantly increased in the presence of an inducer (e.g., an inflammatory mediator or 5-aminosalicylic acid).

MnSOD prohancer elements of the invention can be located within intron 2 of the MnSOD gene and are typically conserved among different species. The element acts as a true enhancer of gene transcription in response to inflammatory mediators (e.g., lipopolysaccharide (LPS), tumor necrosis factor alpha (TNF-$\alpha$), interleukin-1 beta (IL-1$\beta$)). However, a novel property of the element is that it can additionally function in the absence of a promoter to stimulate gene transcription of a heterologous gene. Thus, the element has been designated a "prohancer" to signify that it is a true enhancer which can promote transcription in the absence of a true promoter, most importantly, under physiologic conditions of inflammation.

Accordingly, one aspect of the invention pertains to an isolated polynucleotide which includes an MnSOD prohancer element, or biologically active portion thereof as well as nucleic acid hybridization probes which can be used to identify MnSOD prohancer elements (e.g., used as PCR primers for the amplification or mutation of MnSOD prohancer elements).

Novel MnSOD prohancer elements of the invention (e.g., comprising all or a portion of the nucleotide sequence shown in SEQ ID NO:1 or 2) can be isolated using standard molecular biology techniques and the sequence information provided herein. For example, using all or portion of the nucleic acid sequence of SEQ ID NO:1 or 2 as a hybridization probe, MnSOD prohancer elements can be isolated using standard hybridization and cloning techniques (e.g., as described in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989).

Prohancer elements comprising all or a portion of SEQ ID NO:1 or 2 also can be isolated by polymerase chain reaction (PCR) using synthetic oligonucleotide primers corresponding to all or a portion of the sequences of SEQ ID NO:1 and 2. For example, prohancer elements can be amplified using cDNA, mRNA or, alternatively, genomic DNA, as a template and appropriate oligonucleotide primers according to standard PCR amplification techniques. The nucleic acid so amplified can be cloned into an appropriate vector and characterized by DNA sequence analysis. Oligonucleotides corresponding to MnSOD prohancer elements nucleotide sequences can be prepared by standard synthetic techniques, e.g., using an automated DNA synthesizer.

In one embodiment, an isolated prohancer element of the invention is derived from (i.e., comprises all or a portion of) the nucleotide sequence set forth in SEQ ID NO:1 or the complement thereof, corresponding to a portion of intron 2 of the rat MnSOD gene. Within the sequence of SEQ ID NO:1, a minimal effective promoter element has been mapped to a region of about 260 base pairs shown in SEQ ID NO:5.

In another embodiment, an isolated prohancer element of the invention is derived from the nucleolide sequence set forth in SEQ ID NO:2 or the complement thereof, corresponding to a portion of intron 2 of the human MnSOD gene. Minimal effective promoter elements within SEQ ID NO:2 can be mapped in the same manner as is described herein for SEQ ID NO:1.

Isolated regulatory elements having the biological activty of an MnSOD prohancer element generally consist of at least about 230, 230–260, 260, 260–300, 300–350, 350 or more nucleotides in length and can be derived from SEQ ID NO:1 or SEQ ID NO:2. For example, the 260 bp element shown in SEQ ID NO:5 corresponds to a prohancer element derived from SEQ ID NO:1 (rat).

The nucleotide sequences provided in SEQ ID NOS: 1 and 2 also allow for the generation of probes and primers which can be used to identify and/or clone MnSOD prohancer elements from other species. The probe/primer typically comprises substantially purified oligonucleotide. Probes based on the provided MnSOD prohancer nucleotide sequences can be used to detect transcripts or genomic sequences encoding the same or related prohancer elements. Thus, the probe can also contain a label group attached thereto, e.g., the label group can be a radioisotope, a fluorescent compound, an enzyme, or an enzyme co-factor. Suitable oligonucleotide probes typically comprise a region of nucleotide sequence that hybridizes under stringent conditions to at least about 12 or 15, preferably about 20 or 25, more preferably about 30, 35, 40, 45, or 50 consecutive nucleotides of a sense sequence of SEQ ID NO:1 or 2, of an anti-sense sequence of SEQ ID NO:1 or 2, or of a naturally occurring variant or mutant of SEQ ID NO:1 or 2.

Accordingly, proenhancer elements of the invention also include regulatory sequences which are highly homologous (i.e., which share at least about 60%, preferably at least about 70%, and more preferably about 80–90% or more sequence identity) with all or a biologically active portion of SEQ ID NOS:1 and 2. In a particular embodiment, the prohancer element comprises a nucleic acid sequence having at least about 90%, 95%, 98%, or more identity with the sequence of SEQ ID NO:1. In another particular embodiment, the prohancer element comprises a nucleic acid sequence having at least about 70%, 75%, 80%, 85%, 90%, 95%, or more identity with the sequence of SEQ ID NO:2. The percent identity to the prohancer sequence of either SEQ ID NO:1 or SEQ ID NO:2 need not be limited to the specific percentages given, but is also meant to include all sequences derived from the nucleotide sequence of SEQ ID NO:1 or SEQ ID NO:2, which retain prohancer function, e.g., the ability to promote inducible transcription of a polynucleotide operatively linked to the prohancer element.

Highly homologous nucleic acid molecules (e.g., corresponding to naturally occurring variants of the provided MnSOD prohancer elements and/or functionally related prohancer elements) can be isolated based on their homology to the MnSOD prohancer elements disclosed herein using the polynucleotide sequences disclosed herein, or a portion thereof, as a hybridization probe according to standard hybridization techniques under stringent hybridization conditions. For example, nucleic acid molecules corresponding to related MnSOD prohancer elements can be mapped to the same intronic locus (e.g., intron 2) within MnSOD genes from species other than rat and human.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 2. In another embodiment, a polynucleotide of the present invention comprises a nucleotide sequence which is at least about 150, 200, 250, 260, 300, 350, 400, 450 or more nucleotides in length and hybridizes under stringent hybridization conditions to the nucleotide sequence of SEQ ID NO:1 or 2, and has prohancer function. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, N.Y. (1989). 6.3.1–6.3.6. A preferred, non-limiting example of stringent hybridization conditions are hybridization in 6× sodium chloride/sodium citrate (SSC) at about 45° C. followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of SEQ ID NO:1 or 2 corresponds to a naturally-occurring nucleic acid molecule. As used herein, a "naturally-occurring" nucleic acid molecule refers to an RNA or DNA molecule having a nucleotide sequence that occurs in nature.

To determine the percent identity of two nucleic acid sequences, the sequences are aligned for optimal comparison purposes (e.g., gaps can be introduced in one or both of a first and a second nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90% or 95% of the length of the reference sequence. The nucleotides at corresponding nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two nucleotide sequences is determined using the algorithm of E. Meyers and W. Miller (CABIOS, 4:11–17 (1989) which has been incorporated into the ALIGN program (version 2.0) (available at http://vega.igh.cnrs.fr/bin/alignguess.egi).

Nucleic acid sequences can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain homologous nucleotide sequences. To obtain gapped alignments for comparison purposes, Gapped BLAST can be utilized as described in Altschul et al., (1997) *Nucleic Acids Res.* 25(17): 3389–3402. When utilizing BLAST and Gapped BLAST programs, the default parameters of the respective programs (e.g., NBLAST) can be used. See URL: ncbi.nlm.nlh.gov.hhttp://www.ncbi.nlm.nib.gov. Additionally, the "Clustal" method (Higgins and Sharp, Gene, 73:237–44, 1988) and "Megalign" program (Clewley and Arnold, Methods Mol. Biol, 70:119–29. 1997) can be used to align sequences and determine similarity, identity, or homology.

In addition to naturally-occurring variations in the MnSOD prohancer sequences (e.g., between species), the skilled artisan will further appreciate that changes can be introduced by mutation into the nucleotide sequences of SEQ ID NO:1, 2, or 5 without altering the functional ability of the MnSOD prohancer elements.

Accordingly, another aspect of the invention pertains to nucleic acid molecules comprising MnSOD prohancer elements that contain changes in nucleic acid residues, yet which retain prohancer activity. Mutations can be introduced into SEQ ID NO:1, 2, or 5 by standard techniques, such as site-directed mutagenesis and PCR-mediated mutagenesis, and the resultant mutants can be screened for MnSOD prohancer activity to identify mutants that retain transcriptional regulatory activity.

In addition to the polynucleotides encoding MnSOD prohancer elements described above, another aspect of the invention pertains to isolated nucleic acid molecules which are antisense thereto. An "antisense" nucleic acid comprises a nucleotide sequence which is complementary to a "sense" nucleic acid sequence. Accordingly, an antisense nucleic acid can hydrogen bond to a sense nucleic acid.

Given the coding strand or "sense" sequences encoding MnSOD prohancer elements disclosed herein (e.g., SEQ ID NO:1, 2, or 5), antisense nucleic acids of the invention can be designed according to the rules of Watson and Crick base pairing. The antisense nucleic acid molecule can be complementary to the entire MnSOD prohancer element, but more preferably is an oligonucleotide which is antisense to only a portion of the MnSOD prohancer element. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouraci, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA comprising an MnSOD prohancer element. In one embodiment, an antisense nucleic acid molecule of the invention can be used to inhibit expression (e.g., basal or inducible expression) of a nucleic acid operatively linked to a MnSOD prohancer element, e.g., by forming triple helical structures that prevent transcription of the target nucleic acids in target cells. See generally, Helene, C. (1991) *Anticancer Drug Des.* 6(6):569–84; Helene. C. et al. (1992) *Ann. N.Y. Acad. Sci.* 660:27–36; and Maher, L. J. (1992) *Bioassays* 14(12):807–15.

The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In yet another embodiment, the MnSOD prohancer element nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of MnSOD prohancer element nucleic acid molecules can be used in therapeutic and diagnostic applications. For example, PNAs can be used as antisense or antigene agents for sequence-specific modulation of gene expression by, for example, inducing transcription or translation arrest or inhibiting replication, or as probes or primers for DNA sequencing or hybridization (Hyrup B. et al. (1996) supra; Perry-O'Keefe supra).

In another embodiment, PNAs of MnSOD prohancer elements can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of prohancer element nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For An example, a DNA chain can be synthesized on a solid support using standard phosphoramidite coupling chemistry and modified nucleoside analogs, e.g., 5'-4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents: (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

In certain embodiments, it will be advantageous to employ nucleic acid sequences of the present invention in combination with an appropriate means, such as a label, for determining hybridization. A wide variety of appropriate indicator means are known in the art including fluorescent, radioactive, enzymatic or other ligands, such as avidin/ biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

II. Transcriptional Regulation by MnSOD Prohancer Elements

MnSOD prohancer elements of the invention are capable, when induced, of promoting transcription of one or more operatively linked heterologous polynucleotide sequence(s). Accordingly, an important aspect of the present invention is the ability to modulate, alter, or regulate, either positively, or negatively, the activity or efficiency of a prohancer element through the use of transcriptional activators, and particularly, transcriptional inducers.

In particular, prohancer elements of the invention provide for inducible expression of sequences that are operatively linked to said elements. In one embodiment, induction of gene expression is provided by inflammatory mediators. Exemplary inflammatory mediators include for example, lipopolysaccharide (LPS), tumor necrosis factor-alpha (TNF-α), and interleukin-1 beta (IL-1β) which are shown in the Examples provided herein to activate, or increase the activity of, the prohancer elements. Other suitable inducers include compounds related to these inflammatory mediators.

For example, inflammatory cytokines can be divided into two groups: those involved in acute inflammation and those responsible for chronic inflammation. IL-1, TNF-alpha, IL-6, IL-11, IL-8 and other chemokines, G-CSF, and GM-CSF play an important role in acute inflammation. Another subset of cytokines is involved in chronic inflammation. This latter group can be subdivided into cytokines mediating humoral responses such as IL-4, IL-5, IL-6, IL-7, IL-12 and IL-13, and those mediating cellular responses such as IL-1, IL-2, IL-3, IL-4, IL-7, IL-9, IL-10, and IL-1 5, the interferons, and transforming growth factors In another embodiment, a compound such as 5-amionsalicylic acid can be used to induce a prohancer element of the invention. In fact, the use of any molecule or inducer which regulates the activity of the disclosed prohancers are contemplated to be useful. The inventors contemplate that one could either directly contact a transformed cell or animal comprising the prohancer element constructs disclosed herein with such an inducer, and thus cause an increase in transcription from the prohancer constructs. Alternatively, contact with one or more substances which increase the production of the inflammatory mediators can be used to induce a prohancer element of the invention. In the case of an whole organism, the activity of a prohancer element could be naturally activated in vivo during a physiologic inflammatory response.

In certain embodiments, the heterologous polynucleotide sequence to be transcriptionally controlled (or promoted) by one or more of the prohancer elements include, but are not limited to, heterologous nucleotide sequences encoding heterologous proteins, ribozymes, and antisense constructs.

III. Recombinant Vectors and Host Cells

In another embodiment, the invention provides a vector, preferably an expression vector, containing one or more MnSOD prohancer elements of the invention in opertive linkage with a heterologous polynucleotide(s) of interest, such that expression of the heterologous polynucleotide(s) is under the transcriptional control of the MnSOD prohancer element. The MnSOD prohancer elements of the invention may be used under the appropriate conditions to direct high level or regulated expression of the heterologous polynucleotide(s) either alone, or with a heterologous promoter. The use of recombinant promoters to achieve protein expression is generally known to those of skill in the art of molecular biology, for example, see Sambrook et al., (1989). For eukaryotic expression, preferred promoters include those such as a CMV promoter, an RSV LTR promoter, a β-actin promoter, thymidine kinase promoter, an insulin promoter, an SV40 promoter.

The MnSOD prohancer elements of the invention may be cloned into an expression vector in the form of multiple untis, in numerous combinations and organizations, in forward and reverse orientations, and the like. The precise optimal location of the prohancer sequences with respect to the heterologous polynucleotide sequence to be expressed may vary. A recombinant vector of the invention may also contain other regulatory elements, e.g., transcription termination sequences, polyadenylation signals, tissue-specific regulatory sequences.

The recombinant expression vectors of the invention can be designed for inducible expression of a protein and/or RNA in prokaryotic or eukaryotic cells. It will be appreciated by those skilled in the art that the design of a recombinant vector can depend on such factors as the choice of the host cell to be transformed, the level of expression desired, and the like. The recombinant vectors of the invention can be introduced into host cells to thereby produce proteins or peptides, including fusion proteins or peptides, and/or functional RNAs, e.g, antisense RNA or ribozymes, encoded by a polynucleotide operatively linked to a prohancer element. In certain embodiments, the recombinant vector may be dispersed in a pharmaceutically acceptable solution.

The recombinant vector may be a plasmid, a cosmid, a BAC (bacterial artificial chromosomes), HAC (human artificial chromosomes), YAC (yeast artificial chromosomes), or a viral vector. Viral vectors include replication defective retroviruses. adenoviruses and adeno-associated viruses. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. The genome of adenovirus can be manipulated such that it encodes and expresses a heterologous protein or RNA under the control of an prohancer element of the invention, but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Alternatively, an adeno-associated virus vector such as that described in Tratschin et al. (1985) *Mol. Cell. Biol.* 5:3251–3260 can be used.

Appropriate cloning and expression vectors that may be modified for use with prohancer elements of the invention, are known in the art, and are described in, for example, Powels et al. (*Cloning Vectors: A Laboratory Manual,* Elsevier, N.Y., 1985). For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, e.d, Cold Spring Harbor Laboratory, Cold Spring Harbor Laboratory Press, Cold Spring Harbor, N.Y., 1989. Another aspect of the invention pertains to host cells containing a nucleic acid molecule of the invention, e.g., a prohancer element operatively linked to a heterolgous polynucleotide sequence within a recombinant expression vector or a transgene.

Host cells include bacterial cells such as *E. coli,* insect cells (using baculovirus expression vectors) yeast cells, mammalian cells, or plant cells. Suitable host cells are discussed further in Goeddel, *Gene Expression Technology: Methods in Enzymology* 185, Academic Press, San Diego, Calif. (1990). Host cells in which the genetic constructs of the present invention may be expressed include mammalian cells, and in particular mammalian cells such as those from a human, monkey, hamster, caprine, feline, canine, equine, porcine, lupine, or murine. A host cell may also be a cell cultured in vitro or a cell present in vivo (e.g., a cell targeted for gene therapy). The host cell can further be a fertilized oocyte, embryonic stem cell or any other stem cell used in the creation of non-human transgenic or homologous recombinant animals.

IV Methods of Nucleic Acid Delivery and DNA Transfection

Nucleic acids of the invention can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, and receptor-mediated mechanisms (Curiel et al. 1991, 1992; Wagner et al., 1992a; 1992b). Suitable methods for transfecting host cells can be found in Sambrook et al. (*Molecular Cloning: A Laboratory Manual,* 2nd Edition, Cold Spring Harbor Laboratory press (1989)), and other laboratory textbooks.

The number of host cells transformed with a nucleic acid of the invention will depend, at least in part, upon the type of recombinant expression vector used and the type of transfection technique used. Nucleic acids can be introduced into a host cell transiently, or more typically, for long term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acid of interest. Preferred selectable markers include those which confer resistance to certain drugs, such as G418 and hygromycin. Selectable markers can be introduced on a separate plasmid from the nucleic acid of interest or, are introduced on the same plasmid. Host cells transfected with a nucleic acid of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418. Cells that have incorporated the selectable marker gene will survive, while the other cells die.

Nucleic acids can also be transferred into cells in vivo, for example by application of a delivery mechanism suitable for introduction of nucleic acid into cells in vivo, such as retroviral vectors (see e.g., Ferry, N et al. (1991) *Proc. Natl. Acad. Sci. USA* 88:8377–8381; and Kay, M. A. et al. (1992) *Human Gene Therapy* 3:641–647), adenoviral vectors (see e.g., Rosenfeld, M. A. (1992) *Cell* 68:143–155; and Herz, J. and Gerard, R. D. (1993) *Proc. Natl. Acad. Sci. USA* 90:2812–2816), receptor-mediated DNA uptake (see e.g., Wu, G. and Wu, C. H. (1988) *J. Biol. Chem.* 263:14621; Wilson et al. (1992) *J. Biol. Chem.* 267:963–967; and U.S. Pat. No. 5,166.320), direct injection of DNA (see e.g., Acsadi et al. (1991) *Nature* 332: 815–818; and Wolff et al. (1990) *Science* 247:1465–1468) or particle bombardment (see e.g., Cheng, L. et al. (1993) *Proc. Natl. Acad. Sci. USA* 90:4455–4459; and Zelenin, A. V. et al. (1993) *FEBS Letters* 315:29–32). For gene therapy purposes, cells can be modified in vitro and administered to a subject or, alternatively, cells can be directly modified in vivo.

Liposomes and/or nanocapsules may also be used for the introduction of polynucleotides comprising the prohancer elements of the present invention into suitable host cells. In particular, the prohancer polynucleotide compositions of the present invention may be formulated for delivery in a solution, such as DMSO, or alternatively encapsulated in lipid particle, liposomes, vesicle, nanosphere, or nanoparticle. Should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition. sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the prohancer nucleic acids of the present invention. Nanocapsules can generally entrap compounds in a stable and reproducible way (Henry-Michelland et al., 1987). To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1984; 1988).

In certain embodiments, a cell can be transformed in vitro or in vivo with a prohancer element of the invention, either alone or operably linked to a heterologous polynucleotide sequence (e.g., a transgene), which can be inserted into a particular locus in the cell genome. Methods for gene targeting a site-specific insertion of transgenes into chromosomal DNA are well known in the art and include, for example, the mammalian Cre/lox system (Sauer et al. (1998) Methods 14:381–392) or homologous recombination (see, e.g., U.S. Pat. No. 5,614,396). By targeting the prohancer regulatory sequences to locations upstream of endogenous genes, expression of these genes can be controlled accordingly: Alternatively, the prohancer elements may regulate the inducible expression of a heterologous transgene.

The present invention is widely applicable to a variety of situations where it is desirable to turn gene expression on and off, e.g., to regulate the level of gene expression in a rapid, efficient and controlled manner.

For example, the prohancer element can be ligated into a promoterless expression vector into which genes of interest can be cloned and used for transfection into a variety of cell types. The gene product will be produced at basal levels unless the prohancer element is activated with LPS, IL-1β, TNF-α, or 5-aminosalicylic acid to stimulate transcription. Thus, gene products can be produced in cells in a timed, coordinated fashion, and at very high levels. Advantages over other types of stimulated promoters such as c-fos would be that it is unnecessary to serum starve or to alter the growth media.

Other applications for prohancer elements of the invention include gene therapy. Prohancer elements can be operatively linked to genes of interest and introduced into cells either in vivo or in vitro. The prohancer can then cause inducible expression of the gene upon contact with non-toxic levels of inflammatory stimuli or 5-aminosalicylic acid. Such stimuli can be introduced into the cell along with the prohancer/gene construct or, during active inflammation, inflammatory stimuli are naturally produced, thereby activating the prohancer to induce expression of the gene.

Accordingly, in another embodiment, the invention provides an expression system for specifically inducing the expression of a heterologous polynucleotide. The expression system generally comprises 1) a polynucleotide comprising one or more MnSOD prohancer elements operably linked to a heterologous polynucleotide of interest, wherein expression of the heterologous polynucleotide is under the control of the prohancer element(s), and such that activation of the prohancer results in expression of the heterologous polynucleotide; and 2) a compound which activates the prohancer element, or a polynucleotide encoding a compound compound which activates the prohancer element.

The expression system allows for inducible expression of a polynucleotide in a cell. Accordingly, in a further embodiment, the invention provides a method of achieving inducible transcripton and/or expression of a heterologous polynucleotide in a cell, comprising contacting the cell with an effective amount of a compound which activates the prohancer element.

Prohancers of the invention also can be used to cause inducible expression of antisense polynucleotides (e.g., ribozymes0 which "down-regulate" the expression of a particular gene or nucleic acid in a cell. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave mRNA transcripts to thereby inhibit translation of an unwanted or deleterious mRNA. For example, a derivative of a Tetrahymena L-19 IVS RNA can be constructed in which the nucleotide sequence of the active site is complementary to the nucleotide sequence to be cleaved in an target mRNA. See, e.g., Cech et al. U.S. Pat. No. 4,987,071; and Cech et al. U.S. Pat. No. 5,116,742. Alternatively, known target mRNAs can be used to select a catalytic RNA having a specific ribonuclease activity from a pool of RNA molecules. See, e.g., Bartel, D. and Szostak, J. W. (1993) Science 261:1411–1418.

In other aspects of the present invention, the prohancer elements may be used to modulate inducible expression of a heterologous gene. A heterologous gene may include a native or mutated gene, or a fusion gene. Exemplary heterologous genes which are contemplated to be useful include, but are not limited to, reporter genes (e.g., GFP, GUS, lacZ and aequorin), as well as therapeutically beneficial and cytoprotective genes.

Genes of particular interest to be expressed in cells of a subject for treatment of genetic or acquired diseases include those encoding adenosine deaminase, Factor VIII, Factor IX, dystrophin, β-globin, LDL receptor, CFTR, insulin, erythropoietin, anti-angiogenesis factors, growth hormone, glucocerebrosidase, β-glucouronidase, α1-antitrypsin, phenylalanine hydroxylase, tyrosine hydroxylase, ornithine transcarbamylase, arginosuccinate synthetase, UDP-glucuronysyl transferase, apoA1, TNF, soluble TNF receptor, interleukins (e.g., IL-2), interferons (e.g., α- or γ-IFN) and other cytokines and growth factors. Cytoprotective genes or "cytoprotectants" include genes that protect a cell against free radical damage, e.g., HO-1, IL-10 and HSP70.

Another embodiment of the invention relates to a method of identifying a factor, e.g., a transcriptional regulatory protein, that interacts with a MnSOD prohancer element, or an inducer of a MnSOD prohancer element. This method generally involves contacting a sample suspected of containing a prohancer-interacting element with a prohancer polynucleotide composition under conditions effective to allow binding of the interacting composition to the prohancer element, and detecting the bound complex. Such methods are particularly desirable in determining biological components, polypeptides, and peptide fragments that bind to the prohancer compositions of the present invention.

A further aspect of the invention provides methods for screening compounds (e.g., peptidemimetics, drugs, small molecules, etc.) which alter the promoter activity of a MnSOD prohancer element, or alter the binding of one or more biological components to the prohancer element. The screening for such chemical entities may be performed e.g., by means of a cell-based assay, an in vitro assay for prohancer function and/or rational drug design. Cell-based assays for screening can be designed e.g., by constructing cell lines in which the expression of a reporter protein, i.e. an easily assayable protein, is dependent on prohancer activity. Such an assay enables the detection of compounds that alter prohancer activity, either directly or indirectly. Alternatively, compounds that inhibit other cellular functions required for the activity of one or more gene products placed under the control of such a prohancer element and expressed in a cell in a prohancer-dependent fashion can be identified.

V. Applications/Uses of the Invention

MnSOD prohancer elements of the invention can be used to cause inducible expression of a variety of different polypeptides and/or proteins either in vivo or in vitro, e.g., in the treatment of diseases. In particular, because MnSOD prohancers are activated by inflammatory stimuli, they can be used to induce expression of cytoprotective genes during inflammation when such inflammatory stimuli are naturally present.

Accordingly, host cells can be engineered, by transformation with prohancer constructs of the present invention, to inducibly turn on expression of genes encoding selected genes and polypeptides under particular conditions. Examples of therapeutic proteins which can be expressed using the prohancer elements include, but are not limited to, CD-4, Factor VIII, Factor IX, von Willebrand Factor, TPA, urokinase, hirudin, interferons, TNF, interleukins, hematopoietic growth factors, antibodies, albumin, leptin, transferrin and nerve growth factors, peptide hormones.

Cells engineered to produce such proteins could be used for either in vitro production of the protein or for in vivo, cell-based therapies. In vitro production would entail purification of the expressed protein from either the cell pellet for proteins remaining associated with the cell or from the conditioned media from cells secreting the engineered protein. In vivo, cell-based therapies would be based on expression of the engineered protein.

The cDNA's encoding a number of therapeutically useful human proteins are available.

VI. Production of Polypeptides In Vitro

Large scale production of a protein of interest can be accomplished using cultured cells in vitro which have been modified to contain a gene of interest operatively linked to a prohancer sequence of the invention. For example, mammalian, yeast or bacterial cells can be engineered to contain these nucleic acid components, as described herein. The mammalian, yeast and bacterial cells can then be cultured using standard techniques. Expression of the gene and subsequent production of the protein of interest can then be promoted by treating the cell with an effective amount of an inducer compound (e.g., 5-aminosalicylic acid, IL-1β, TNF-α, or LPS) such as to activate the prohancer element.

Characteristics of particular interest in selecting a host cell for purposes of production include ease of introducing the prohancers of the present invention and the gene of interest into the host, availability of expression systems, efficiency of expression, stability of the gene of interest in the host, and the presence of auxiliary genetic capabilities. In general, vectors containing replicon and control sequences which are compatible with the host cell are used in connection with these hosts.

Nucleic acid constructs will include the prohancers of the present invention functionally linked to a gene of interest, and optionally including a 3' end DNA sequence that acts as a signal to terminate transcription and allow for the polyadenylation of the resultant mRNA. The vector ordinarily carries a replication site, as well as a selectable marker which is capable of providing phenotypic selection in transformed cells.

As the DNA sequence between the transcription initiation site and the start of the coding sequence, i.e. the untranslated leader sequence, can influence gene expression, one may also wish to employ a particular leader sequence. Preferred leader sequences are contemplated to include those which include sequences predicted to direct optimum expression of the attached gene, i.e. to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in animals, and in humans in particular, will be preferred.

Mammalian cells can be propagated in vitro in two modes: as non-anchorage dependent cells growing freely in suspension throughout the bulk of the culture; or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. Large scale suspension culture based on microbial (bacterial and yeast) fermentation technology has clear advantages for the manufacturing of mammalian cell products. The processes are relatively simple to operate and straightforward to scale up. Homogeneous conditions can be provided in the reactor which allows for precise monitoring and control of temperature, dissolved oxygen, and pH, and ensure that representative samples of the culture can be taken.

However, suspension cultured cells cannot always be used in the production of biologicals. Suspension cultures are still considered to have tumorigenic potential and thus their use as substrates for production put limits on the use of the resulting products in human and veterinary applications (Petricciani, 1987; Larsson and Litwin, 1987). Viruses propagated in suspension cultures as opposed to anchorage-dependent cultures can sometimes cause rapid changes in viral markers, leading to reduced immunogenicity (Bahnemann, 1980). Finally, sometimes eve: recombinant cell lines can secrete considerably higher amounts of products when propagated as anchorage-dependent cultures as compared with the same cell line in suspension (Nilsson and Mosbach, 1987). For these reasons, different types of anchorage-dependent cells are used extensively in the production of different biological products.

VII. Production of Polypeptides In Vivo

Transgenic Organisms

A nucleic acid comprising a prohancer element of the invention, either alone or operatively linked to a polynucleotide of interest, can be transferred into a fertilized oocyte of a non-human animal to create a transgenic animal. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. In one embodiment, the non-human transgenic animal is a mouse, although the invention is not limited thereto. Transgenic animals may be useful for the large scale production of proteins, or the production of antibodies.

A transgenic animal can be created, for example, by introducing a nucleic acid comprising a MnSOD regulatory element operatively linked to a heterologous polynucleotide encoding a gene of interest into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and Hogan, B. et al., (1986) *A Laboratory Manual*, Cold Spring Harbor, N.Y., Cold Spring Harbor Laboratory. A transgenic founder animal can be used to breed additional animals carrying the transgene. Transgenic animals carrying a transgene of the invention can further be bred to other transgenic animals carrying other transgenes.

It will be appreciated that, in addition to transgenic animals, the regulatory system described herein can be applied to other transgenic organisms, such as transgenic plants. Transgenic plants can be made by conventional techniques known in the art.

Homologous Recombinant Organisms

The invention also provides a homologous recombinant non-human organism in which a nucleic acid coprising a MnSOD prohancer regulatory element operatively linked to a heterologous polynucleotide encoding a gene of interest has been introduced into a specific site of the organism's genome, i.e., the nucleic acid has homologously recombined with an endogenous gene.

To create such a homologous recombinant organism, a vector is prepared which contains DNA encoding the fusion protein flanked at its 5' and 3' ends by additional nucleic acid of a eukaryotic gene at which homologous recombination is to occur. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA.

In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis; W. and Sauer, B. (1993) *Nucl. Acids Res.* 21:2025–2029; and Fukushige, S. and Sauer, B. (1992) *Proc. Natl. Acad. Sci. USA* 89:7905–7909) and the FLP recombinase-FRT target system (e.g., as described in Dang, D. T. and Perrimon, N. (1992) *Dev. Genet.* 13:367–375; and Fiering, S. et al. (1993) *Proc. Natl. Acad. Sci. USA* 90:8469–8473).

VIII. Gene Therapy

MnSOD prohancer elements of the invention have numerous advantageous properties that render them particularly suitable for application in gene therapy.

Accordingly, an important characteristic of the prohancer elements of the invention is that, unlike other inducible regulatory systems available in gene therapy vectors, this sequence contains the capacity to be activated by the body's own response to inflammation through the endogenous release of IL-1β and/or TNF-α. This discovery enables development of custom gene therapy vector systems, which are exquisitely controlled during an inflammatory response by either elevating expression of cytoprotective proteins or, potentially, by down-regulating deleterious gene products through anti-sense transcription.

For example, the elements can be used as an "on"/"off" switch for gene expression that allows for regulated dosing of a gene product in a subject. Indeed, there are several situations in which it may be desirable to be able to provide a gene product at specific levels and/or at specific times in a regulated manner, rather than simply expressing the gene product constitutively at a set level.

For example, a gene of interest can be switched "on" at fixed intervals (e.g., daily, alternate days, weekly, etc.) to provide the most effective level of a gene product of interest at the most effective time. The level of gene product produced in a subject can be monitored by standard methods (e.g., direct monitoring using an immunological assay such as ELISA or RIA or indirectly by monitoring of a laboratory parameter dependent upon the function of the gene product of interest, e.g., blood glucose levels and the like). This ability to turn "on" expression of a gene at discrete time intervals in a subject while also allowing for the gene to be kept "off" at other times avoids the need for continued administration of a gene product of interest at intermittent intervals. This approach avoids the need for repeated injections of a gene product, which may be painful and/or cause side effects and would likely require continuous visits to a physician. In contrast, the system of the invention avoids these drawbacks.

Moreover, the ability to turn "on" expression of a gene at discrete time intervals in a subject allows for focused treatment of diseases which involve "flare ups" of activity (e.g., many autoimmune diseases) only at times when treatment is necessary during the acute phase when pain and symptoms are evident. At times when such diseases are in remission, the expression system can be kept in the "off" state.

Gene therapy applications that may particularly benefit from the ability of the prohancer elements of the invention to modulate gene expression during discrete time intervals in response to physiologic inflammatory stimuli include both chronic and acute inflammatory conditions such as wound healing, asthma, arthritis, inflammatory bowel disease (e.g., ulcerative colitis), and cardiovascular disease.

Cells types which can be modified for gene therapy purposes include hematopoietic stem cells, myoblasts, hepatocytes, lymphocytes, skin epithelium and airway epithelium. For further descriptions of cell types, genes and methods for gene therapy see e.g., Wilson, J. M et al. (1988) *Proc. Natl. Acad. Sci. USA* 85:3014–3018; Armentano, D. et al. (1990) *Proc. Natl. Acad. Sci. USA* 87:6141–6145; Wolff, J. A. et al. (1990) *Science* 247:1465–1468; Chowdhury, J. R. et al. (1991) *Science* 254:1802–1805; Ferry, N. et al. (1991) *Proc. Natl. Acad. Sci. USA* 88:8377–8381; Wilson, J. M. et al. (1992) *J. Biol. Chem.* 267:963–967; Quantin, B. et al. (1992) *Proc. Natl. Acad. Sci. USA* 89:2581–2584; Dai, Y. et al. (1992) *Proc. Natl. Acad. Sci. USA* 89:10892–10895; van Beusechem, V. W. et al. (1992) *Proc. Natl. Acad. Sci. USA* 89:7640–7644; Rosenfeld, M. A. et al. (1992) *Cell* 68:143–155; Kay, M. A. et al. (1992) *Human Gene Therapy* 3:641–647; Cristiano, R. J. et al. (1993) *Proc. Natl. Acad. Sci. USA* 90:2122–2126; Hwu, P. et al. (1993) *J. Immunol.* 150:4104–4115; and Herz, J. and Gerard, R. D. (1993) *Proc. Natl. Acad. Sci. USA* 90:2812–2816.

Gene therapy applications of particular interest in cancer treatment include overexpression of a cytokine gene (e.g., TNF-α) in tumor infiltrating lymphocytes or ectopic expression of cytokines in tumor cells to induce an anti-tumor immune response at the tumor site), expression of an enzyme in tumor cells which can convert a non-toxic agent into a toxic agent, expression of tumor specific antigens to induce an anti-tumor immune response, expression of tumor suppressor genes (e.g., p53 or Rb) in tumor cells, expression of a multidrug resistance gene (e.g., MDR1 and/or MRP) in bone marrow cells to protect them from the toxicity of chemotherapy.

Gene therapy applications of particular interest in treatment of viral diseases include expression of trans-dominant negative viral transactivation proteins, such as trans-dominant negative tat and rev mutants for HIV or trans-dominant 1Cp4 mutants for HSV (see e.g., Balboni, P. G. et al. (1993) *J. Med. Virol.* 41:289–295; Liem, S. E. et al. (1993) *Hum. Gene Ther.* 4:625–634; Malim, M. H. et al. (I992) *J. Exp. Med.* 176:1197–1201; Daly, T. J. et al. (1993) *Biochemistry* 32:8945–8954; and Smith, C. A. et al. (1992) *Virology* 191:581–588), expression of trans-dominant negative envelope proteins, such as env mutants for HIV (see e.g., Steffy, K. R. et al. (1993) *J. Virol.* 67:1854–1859), intracellular expression of antibodies, or fragments thereof, directed to viral products ("internal immunization", see e.g., Marasco, W. A. et al. (1993) *Proc. Natl. Acad. Sci. USA* 90:7889–7893) and expression of soluble viral receptors, such as soluble CD4. Additionally, the system of the invention can be used to conditionally express a suicide gene in cells, thereby allowing for elimination of the cells after they have served an intended function.

IX. In Vivo Delivery and Treatment Protocols

As discussed above, in certain applications, it is desirable to introduce prohancer elements into cells in vivo.

Adenovirus

One of the preferred methods for in vivo delivery involves the use of an adenovirus expression vector. "Adenovirus expression vector" is meant to include those constructs containing adenovirus sequences sufficient to (a) support packaging of the construct and (b) to express a heterologous polynucleotide that has been cloned therein.

The expression vector comprises a genetically engineered form of adenovirus. Knowledge of the genetic organization or adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be lintked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5□-tripartite leader (TPL) sequence which makes them preferred mRNAs for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell innoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5☐ and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other Viral Vectors

Other viral vectors may be employed as expression constructs in the present invention. Vectors derived from viruses such as vaccinia virus (Ridgeway, 1988; Coupar et al., 1988) adeno-associated virus (AAV) (Ridgeway, 1988; Hermonat and Muzycska, 1984) and herpesviruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-viral Vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, the preferred mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1992a; 1992b). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Eur. Pat. Appl. Publ. No. EP0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also maybe specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues. U.S. Pat. No. 5,399,346 (incorporated herein by reference in its entirety) discloses exemplary ex vivo therapeutic methods.

X. Pharmaceutical Compositions

In certain embodiments, it may be desirable to formulate one or more polynucleotide compositions comprising the prohancer elements of the invention for administration to a mammal, or even, to a human. As such, it may be important to prepare pharmaceutically-acceptable formulations of these polynucleotides, or the polypeptides which they produce. As used herein, the phrase "pharmraceutically-acceptable" refers to molecular entities and compositions that do not produce an adverse, allergic or similar untoward reaction when administered to a human or animal, as appropriate. The term "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Pharmaceutical compositions may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of an aqueous composition that contains a protein as an active ingredient is well understood in the art. Typically, such compositions are prepared as injectables, either as liquid solutions or suspensions, solid forms suitable for solution in, or suspension in, liquid prior to injection can also be prepared. The preparation can also be emulsified.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580) Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

When the route is topical, the form may be a cream, ointment, salve or spray.

The pharmaceutical compositions can be included in a container, pack or dispenser together with instructions for use.

XI. Pharmaceuticals and Methods of Treating Disease

The disclosed compositions may also lend themselves to the development of methods for the treatment of various disease states. Treatment methods will involve treating an individual with an effective amount of a viral particle, as described above, containing a therapeutic gene of interest. An effective amount is described, generally, as that amount sufficient to detectably and repeatedly to ameliorate, reduce, minimize or limit the extent of a disease or its symptoms. More rigorous definitions may apply, including elimination, eradication or cure of disease.

Administration of the therapeutic virus particle to a patient will follow general protocols for the administration of chemotherapeutics, taking into account the toxicity, if any, of the vector. It is anticipated that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. For example, aqueous compositions of the present invention comprise an effective amount of the compound, dissolved or dispersed in a pharmaceutically acceptable carrier or aqueous medium. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

A wide variety of disease states may be treated with compositions according to the present invention. In essence, any disease that can be treated by provision of a protein or nucleic acid is amenable to this approach. Disease states include a variety of genetic abnormalities such as diabetes, cancer, cystic fibrosis and various other diseases that could be treated by increasing or decreasing expression of a protein in a target cell.

Depending on the particular disease to be treated, administration of therapeutic compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients.

In certain embodiments, ex vivo therapies also are contemplated. Ex vivo therapies involve the removal, from a patient, of target cells. The cells are treated outside the patient's body and then returned. One example of ex vivo therapy would involve a variation of autologous bone marrow transplant. Many times, ABMT fails because some cancer cells are present in the withdrawn bone marrow, and return of the bone marrow to the treated patient results in repopulation of the patient with cancer cells. In one embodiment, however, the withdrawn bone marrow cells could be treated while outside the patient with an viral particle that targets and kills the cancer cell. Once the bone marrow cells are "purged," they can be reintroduced into the patient.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time. Unit dose of the present invention may conveniently may be described in terms of plaque forming units (pfu) of the viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher.

Preferably, patients will have adequate bone marrow function (defined as a peripheral absolute granulocyte count of >2,000/mm$^3$ and a platelet count of 100,000/mm$^3$), adequate liver function (bilirubin $\leq$1.5 mg/dl) and adequate renal function (creatinine <1.5 mg/dl).

Viral vectors may be employed to deliver therapeutic genes to cancer cells. Target cancer cells include cancers of the lung, brain, prostate, kidney, liver, ovary, breast, skin, stomach, esophagus, head & neck, testicles, colon, cervix, lymphatic system and blood. Of particular interest are non-small cell lung carcinomas including squamous cell carcinomas, adenocarcinomas and large cell undifferentiated carcinomas.

According to the present invention, one may treat the cancer by directly injecting a tumor with the viral vector. Alternatively, the tumor may be infused or perfused with the vector using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 weeks or longer following the initiation of treatment. Generally, the dose of the therapeutic composition via continuous perfusion will be equivalent to that given by a single or multiple injections, adjusted over a period of time during which the perfusion occurs.

For tumors of $\geq$4 cm, the volume to be administered will be about 4–10 ml (preferably 10 ml), while for tumors of <4 cm, a volume of about 1–3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional viral treatments subsequent to resection will serve to eliminate microscopic residual disease at the tumor site.

A typical course of treatment, for a primary tumor or a post-excision tumor bed will involve multiple doses. Typical primary tumor treatment involves a 6 dose application over a two week period. The two week regimen may be repeated one, two, three, four, five, six or more times. During a course of treatment, the need to complete the planned dosings may be reevaluated.

Cancer therapies also include a variety of combination therapies with both chemical and radiation based treatments. Combination chemotherapies include, for example, cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate.

Combination radiation therapies may be x- and -irradiation. Dosage ranges for x-irradiation range from daily doses of 2000 to 6000 roentgens for prolonged periods of time (3 to 4 weeks), to single doses of 2000 to 6000 roentgens. Dosages for radioisotopes vary widely, and depend on the half-life of the isotope, the strength and type of radiation emitted, and the uptake by neoplastic cells.

Various combinations may be employed, gene therapy is "A" and the radio- or chemotherapeutic agent is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

This invention is further illustrated by the following examples which should not be construed as limiting. The contents of all references, patents and published patent applications cited throughout this application are hereby incorporated by reference.

EXAMPLES

Experimental Procedures

Cell Culture and Transfection

L2 cells, a rat pulmonary epithelial-like cell line (ATCC CCL 149), were grown in Ham's modified F12K medium (GIBCO) with 10% fetal bovine serum (Flow Laboratories), ABAM (Penicillin G 100 U/ml, Streptomycin 0.1 mg/ml, Amphotericin B 0.25 $\mu$g/ml (Sigma) and 4 mM glutamine at 37° C. in room air, 5% $CO_2$. Transfections were carried out using a batch transfection method. Cells were grown on 150 mm tissue culture plates until 70–90% confluent. The cells were transfected with 10 $\mu$g of each expression vector using a modified DEAE-dextran method (Kriegler, 1990). After 24 hours, cells from each 150 mm, batch transfected plate were trypsinized, pooled, and plated onto four separate 100 mm tissue culture plates. After 24 hours, inflammatory mediators were added to the medium of each plate with final concentrations of 0.5 $\mu$g/ml LPS, 10 ng/ml TNF-$\alpha$, or 2 ng/ml IL-1β. Twenty four hours later, total RNA was isolated from the cell monolayers for northern analysis. For the human growth hormone protein assay, individual 100 mm plates were allowed to incubate for 48 hours after the addition of LPS, TNF-α or IL-1β before media samples were collected. Each vector was tested in n≧4 independent experiments to evaluate the reproducibility and effectiveness of each construct.

Generation of Reporter Constructs

From the 17 kb rat MnSOD genomic clone, a 4.5 kb EcoRI/Eag I fragment of 5' untranslated sequence was isolated and the 5' overhang ends filled in using the Klenow fragment of E. coli DNA polymerase I. The resulting blunt-end EcoRI/EagI fragment was cloned into the HincII polylinker site in a promoterless, pUC 12-based human growth hormone expression vector, pØGH, (Selden et al., 1986), creating a 9.3 kb plasmid referred to as Eco/E GH. Unique restriction enzyme sites were utilized to delete increasing portions of the MnSOD Eco/E sequence, creating the promoter deletion vectors illustrated in FIG. 1A. To test for non-specific effects of the inflammatory mediators on hGH expression, we used an hGH expression vector, pTKGH, that contains a minimal promoter from herpes simplex thymidine kinase (Selden et al., 1986).

Figure 2A:
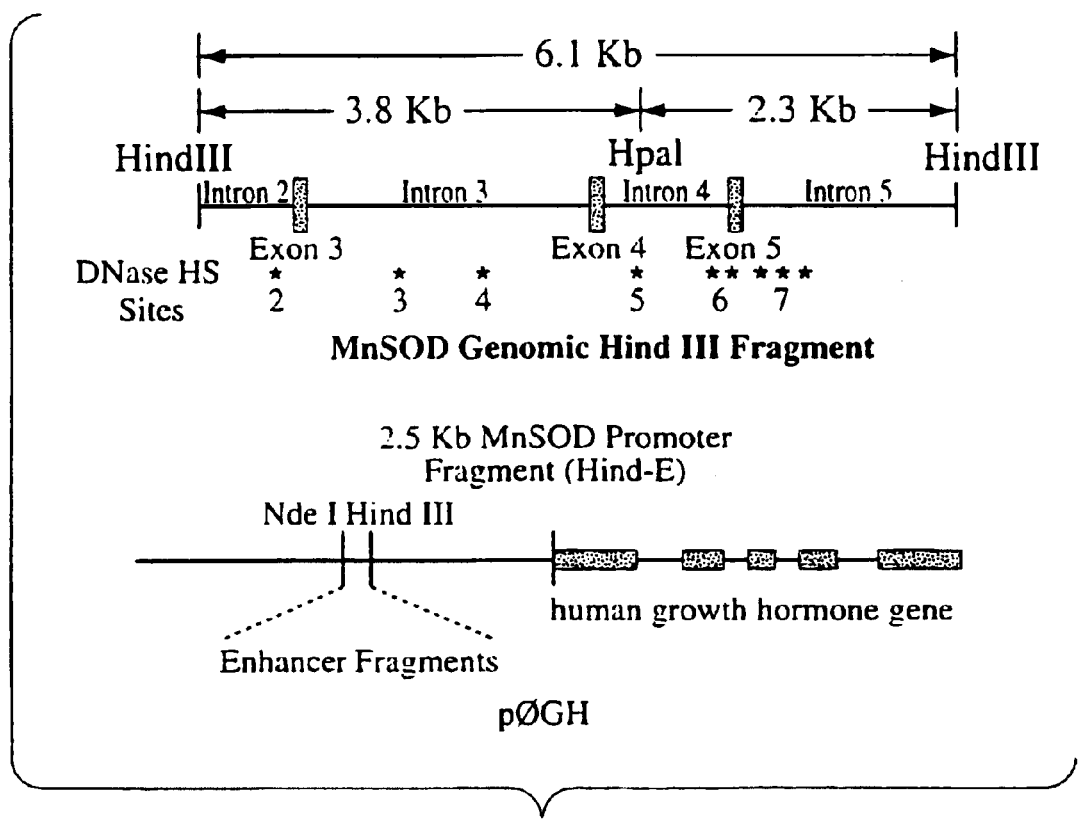
FIG. 2A shows a schematic representation and restriction map of a rat MnSOD genomic clone, and the construction of pØGH expression vectors containing restriction fragments of the MnSOD gene to assess potential enhancer activity. The restriction enzyme sites are indicated above the sequence. DNase I hypersensitive sites 2 through 7 (★) are also indicated.

To identify possible regulatory elements in the MnSOD gene that might interact with the 5' promoter and induce and/or enhance expression of transgene sequences, an internal 6.1 kb HindIII fragment (+1180 to +7312) from the rat MnSOD genomic clone was cloned into the HindIII site of pØGH vector containing the Hind/E promoter fragment, creating a 13.45 kb vector (FIG. 2A). The same 6.1 kb HindIII fragment was also cloned into the pØGH vector containing the Hind/E promoter fragment in the opposite orientation (e.g., 3'→5').

To localize enhancer activity within the 6.1 kb HindIII fragment, the 3.8 Kb HindIII/HpaI fragment (+1180 to +5046) and the 2.3 Kb HpaI/HindIII fragment (+5046 to +7312) (both part of the 6.1 kb fragment) were independently cloned in both orientations into the pØGH vector containing the Hind/E promoter fragment. To clarify the position of the enhancer within the 3.8 Kb HindIII/HpaI fragment, serial 3' and 5' deletions of this fragment were generated (FIGS. 3A and 4A) and cloned into the pØGH vector containing the Hind/E promoter fragment at the HindIII site or the NedI site. Oligonucleotides flanking the regions of interest were designed containing either Hind III or NedI sites for convenient ligation into the restriction sites.

Figure 6A:
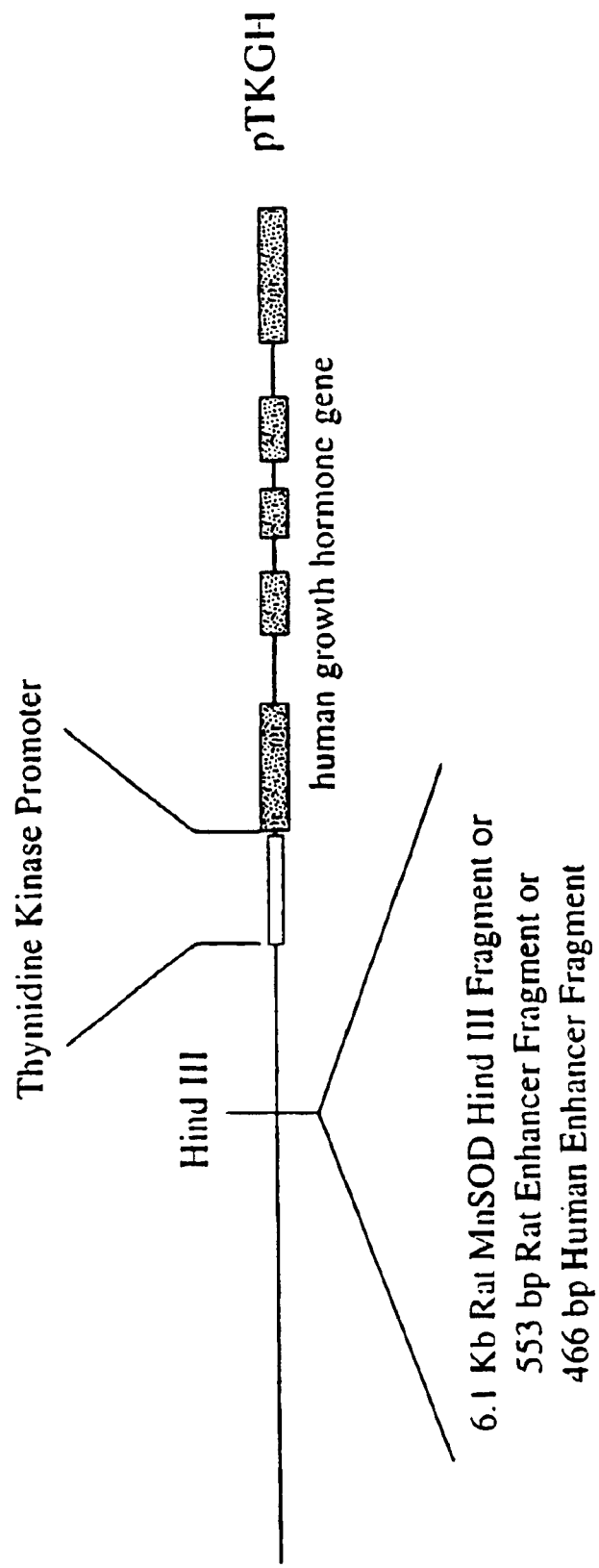
FIG. 6A shows a schematic representation indicating the placement of the rat and human MnSOD enhancer fragments 5' to the human growth hormone reporter gene in the thymidine kinase promoter-human growth hormone vector (pTKGH).

To test whether the enhancer activity was specific to the MnSOD promoter, the plasmid pTKGH, which contains a heterologous, TATA-containing, non-GC-rich promoter, was also used. The 6.1 kb HindIII MnSOD genomic fragment (+1180 to +7312) was cloned into the HindIII site in the pTKGH polylinker in both orientations (FIG. 6A). To evaluate the interaction of the MnSOD promoter with the internal enhancer fragment, the 919 bp fragment of the MnSOD gene containing the entire enhancer region was ligated into the NedI site of the promoter deletion constructs previously described (see FIGS. 3A and 8A).

Comparison of the rat MnSOD enhancer sequence with the analogous region in intron 2 of the human MnSOD gene revealed a high degree of homology in intron 2 (FIG. 5). PCR was used to amplify a 466 bp fragment (+2410 to +2875, human MnSOD, GenBank Accession No. S77127) from human genomic DNA using the following primers:

5'-CGTTAGTGGTTTGCACAAGGAAGATAATCG-3' (SEQ ID NO:3)

5'-GGCTCTGATTCCACAAGTAAAGGACTG-3' (SEQ ID NO:4)

The human MnSOD enhancer fragment was inserted into the pTKGH vector in both orientations (FIG. 6A). The 466 bp human enhancer fragment and the 260 bp, 553 bp or 746 bp rat enhancer fragments were also ligated into the pØGH vector (see FIG. 9A).

RNA Isolation and Northern Analysis

Inducible gene expression in transfected cells was analyzed by directly measuring hGH mRNA and/or endogenous MnSOD mRNA levels. Total RNA was isolated by the guanidinium thiocyanate-phenol-chloroform extraction method described by Chomczynski and Sacchi (1987) with modifications. Twenty μg of RNA was size fractionated on a 1% denaturing agarose gel, transferred to a nylon membrane and UV-crosslinked. Membranes were hybridized with $^{32}$P-labelled cDNA probes from the appropriate genes (e.g., hGH, MnSOD) generated by random primer extension. Membranes were reprobed with cathepsin B as a loading control.

Human Growth Hormone Assay

The concentration of secreted hGH was measured using an $^{125}$Iodine-labeled monoclonal antibody assay kit purchased from Nichols Institute with a lower limit sensitivity of 0.06 ng/ml. Each experimental sample was assayed in duplicate.

Human growth hormone assay data from similarly transfected and treated plates from all experiments were combined. To determine whether treatment with inflammatory mediators increased expression of the hGH reporter, the mean concentration of hGH from all plates transfected with the same vector and treated with the same agonist was compared to untreated transfected control plates (n≧16). We also tested for differences in basal and stimulated hGH expression between vectors. A student's unpaired, two-tailed t test or two way analysis of variance was performed, and a p value of <0.05 was considered significant.

Electrophoretic Mobility Shift Assays (EMSA)

EMSAs were performed as previously described (Fried and Crothers, 1981) with 8 μg nuclear extract prepared from control and LPS, TNF-α, or IL-1β treated L2 cells by high salt extraction (Andrews and Faller, 1991). Binding reactions were carried out at room temperature in 10 mM HEPES, pH 7.9, 100 mM KCl, 1 mM dithiothreitol (DTT), 0.5 mM $MgCl_2$, 0.1 mM EDTA and 8.5% glycerol, to yield a final volume of 20 μl. EMSA probes were made from cloned PCR products of the MnSOD enhancer region between +4130 and +4491 of the rat MnSOD gene. Probes were end-labeled by filling the recessed 3' termini of EcoRI digested fragments with $^{32}$P-dATP using the Klenow fragment of E. coli DNA polymerase I. Fragments used in EMSAs were 3' 143 bp (+4348 to +4491), 5' 143 bp (+4231 to +4374), 100 bp (+4231 to +4331), 95 bp (+4331 to +4426), and 103 bp (+4426 to +4529). Numbers in parentheses refer to the sequence of the rat MnSOD gene, GenBank Accession No. X56600.

Example 1

Characterization of the Rat MnSOD Promoter

The following studies were performed to characterize the region of the rat MnSOD gene responsible for induction of gene expression in response to inflammatory mediators.

Figure 1B:
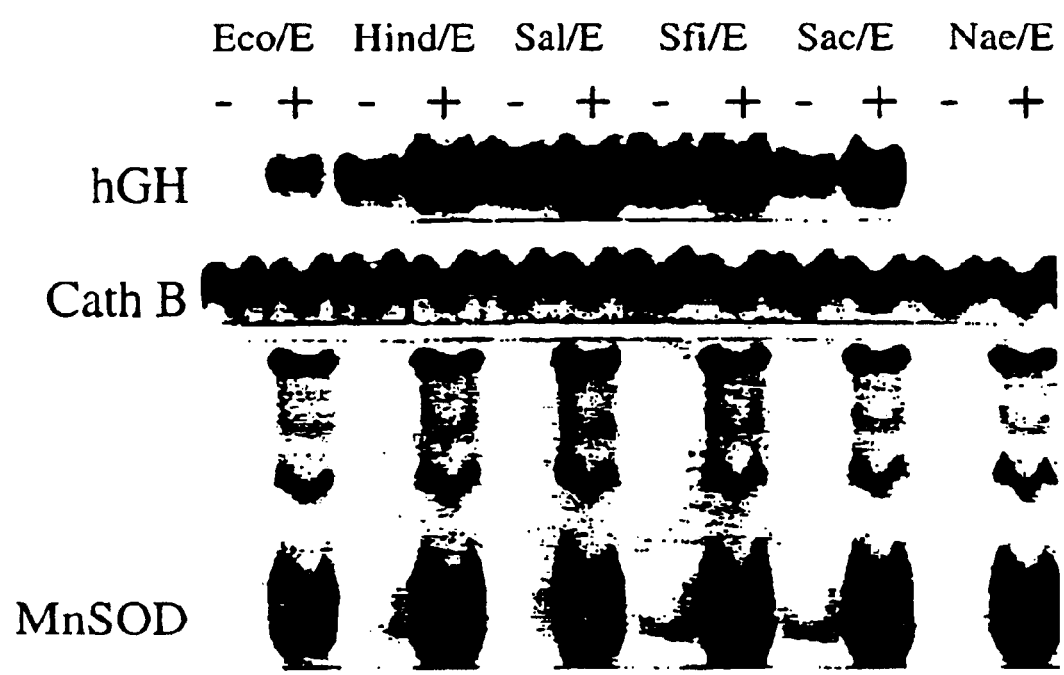
FIG. 1B shows a Northern analysis of hGH and MnSOD mRNA levels in rat lung epithelial cells transfected with pØGH vectors containing promoter deletion fragments of the rat MnSOD gene (FIG. 1A), and stimulated with LPS.
Figure 1C:
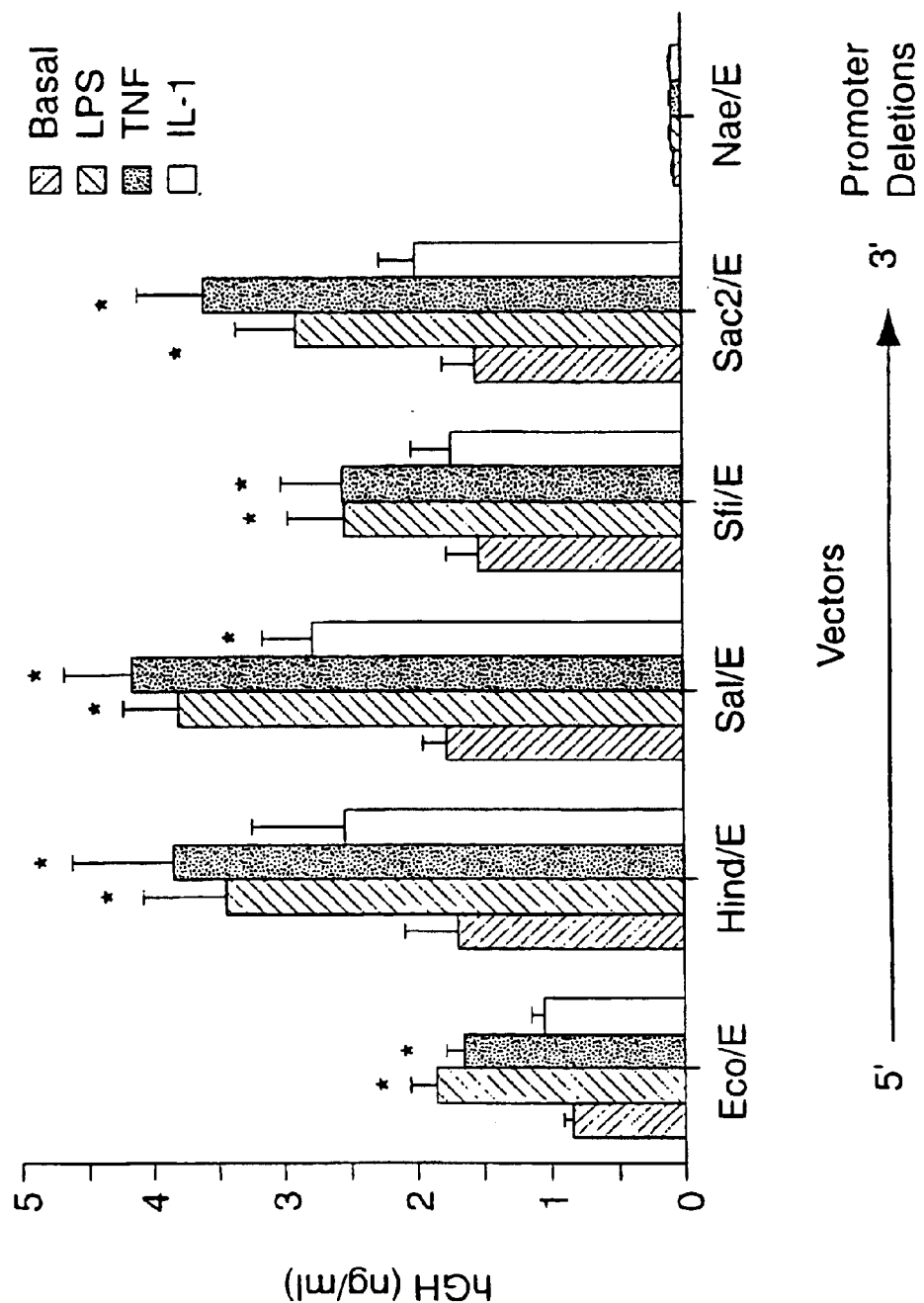
FIG. 1C shows levels of human growth hormone (hGH) protein expressed in rat lung epithelial cells transfected with pØGH vectors containing promoter deletion fragments of the rat MnSOD gene (FIG. 1A), and stimulated with LPS, TNF-α, or IL-1β. Error bars represent the standard error of the mean. A p value of <0.05 was considered significant and is indicated by the *.

The Rat MnSOD Promoter does not Contain all the DNA Elements Necessary for Cytokine-inducible Expression MnSOD gene expression is stimulated by inflammatory mediators, including LPS, TNF-α, and IL-1β, and is due at least in part to de novo gene transcription. To identify sequences in rat MnSOD which confer specificity for LPS-, TNF-α- and IL-1β-dependent gene induction, a series of MnSOD promoter deletion constructs were generated using the promoterless human growth hormone vector pØGH (FIG. 1A). Unique restriction sites within the rat MnSOD 5' flanking sequence were used to create vectors containing the promoter deletions. Each 5' promoter deletion construct contained sequences which incorporated the MnSOD transcriptional start site. Cells transfected with a pØGH reporter vector containing a 4.5 Kb fragment (Eco/E) of the rat MnSOD promoter showed a 2 to 3 fold induction of hGH mRNA levels in response to stimulation with LPS, TNF-α, and IL-1β (FIGS. 1B and 1C). To assure that hGH in the medium reflected the majority of total hGH protein produced by the transfected cells, hGH was also measured in the cell monolayer. Only 2–3% of total hGH was retained in the cells and 97% was secreted into the medium. As the MnSOD promoter was progressively shortened, the deletions had no effect on either basal or stimulated hGH expression (mRNA or protein), until the MnSOD promoter fragment was shortened from the SacII restriction site to the NaeI site at which point all expression was lost. Messenger RNA (FIG. 1B) and protein levels (FIG. 1C) of hGH were comparable suggesting that cytokines did not significantly affect translation, post-translational modification or secretion.

The promoter deletion data suggests that the 5' flanking sequence of the rat MnSOD gene between positions −154 and +32 contains cis-acting elements necessary for basal and a small amount of inducible MnSOD expression. Relative to the ten protein binding sites identified in the MnSOD promoter by in vivo footprinting experiments, these data would indicate that the five sites most proximal to the transcriptional initiation site (within the Sac II fragment) are responsible for the 2 to 3 fold increase in hGH levels compared to controls. However, the magnitude of induction of hGH mRNA and protein levels in the pØGH MnSOD promoter deletion constructs is low (only a 2 to 3 fold induction) compared to the induction of endogenous MnSOD as evaluated by northern analysis. In addition, these constructs contained only 5' flanking sequences of the rat MnSOD gene, which incorporated only one of the seven DNaseI hypersensitive sites identified within the MnSOD gene (see FIG. 2A). Therefore, other regulatory elements outside of the 5' proximal promoter must be involved in the induction of MnSOD gene expression by LPS, TNF-α and IL-1β.

Example 2

Characterization of MnSOD Enhancer Elements

The studies described in Example 1 showed that the rat MnSOD gene 5' proximal promoter was not solely responsible for inducible gene expression. Accordingly, the following studies were performed to identify and characterize further transcriptional regulatory elements within the MnSOD gene itself (e.g., within intron sequences).

Figure 2B:
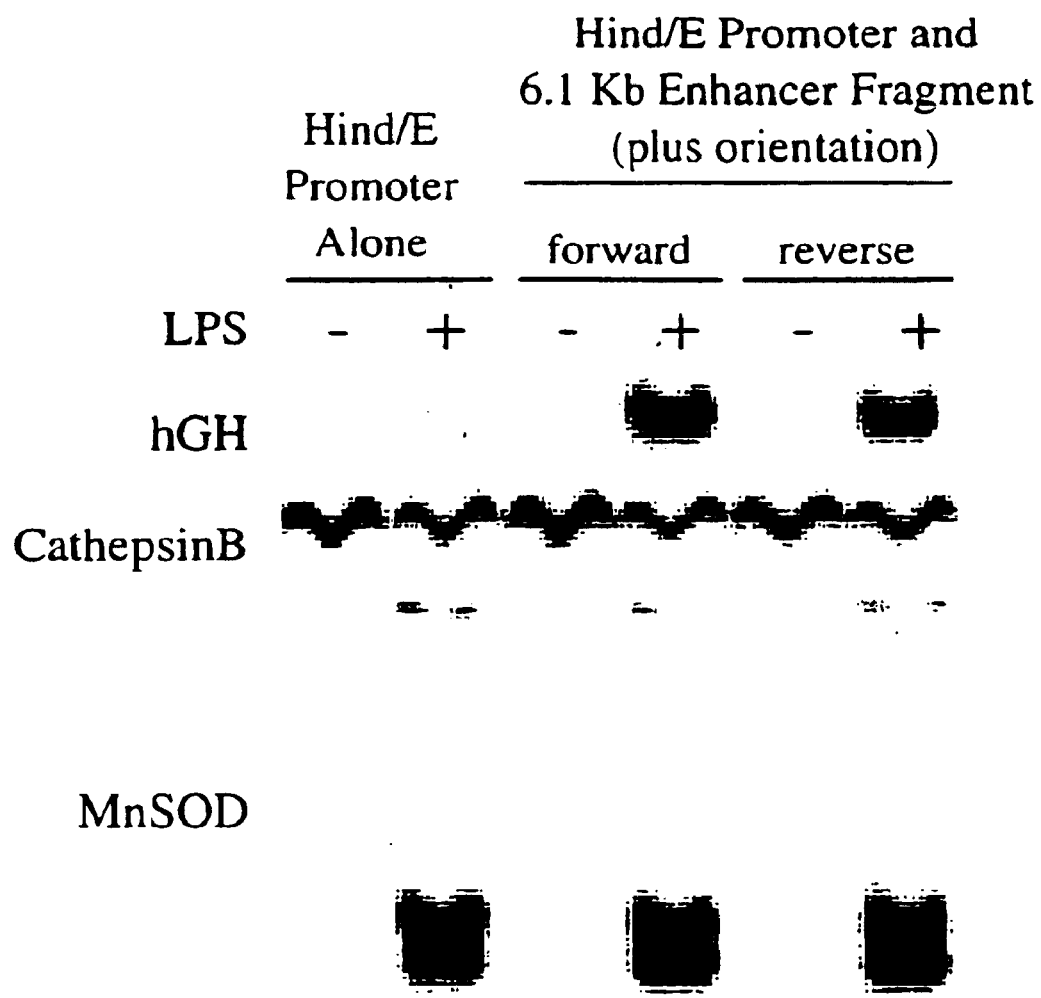
FIG. 2B shows a Northern analysis of hGH and MnSOD mRNA levels in rat lung epithelial cells transfected with the pØGH vector containing the 6.1 Kb internal Hind III fragment of the rat MnSOD gene (FIG. 2A), and stimulated with LPS.

A Novel Inducible Cis-acting Enhancer Element Exists within the Rat and Human MnSOD Genes To determine whether the remaining DNaseI hypersensitive sites described in Example 1 (within the MnSOD gene) contained regulatory function, pØGH expression vectors were created that contained both a 2.5 Kb fragment of the MnSOD promoter (Hind/E) and a 6.1 kb HindIII internal fragment of the MnSOD gene which contains all of the other Dnase I hypersensitive sites (FIG. 2A). Expression of hGH mRNA in cells transfected with this vector was compared to expression of hGH in cells transfected with a pØGH construct containing only the 5' Hind/E promoter fragment. Inclusion of the 6.1 Kb HindIII internal MnSOD genomic fragment, resulted in a robust induction (10–15 fold) of hGH mRNA levels in response to LPS, TNF-α and IL-1β stimulation, and the effect was independent of the orientation of the 6.1 kb HindIII fragment within the vector (FIG. 2B).

Figure 2C:
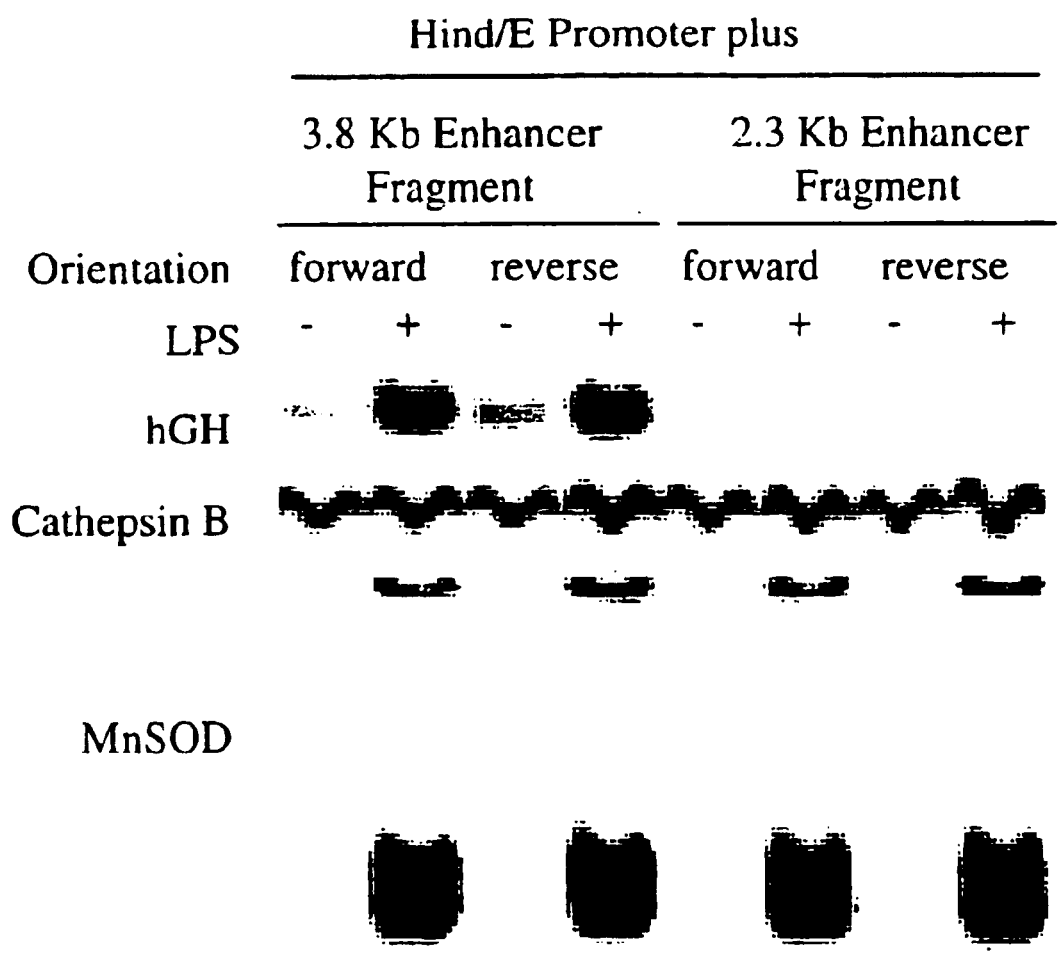
FIG. 2C shows a Northern analysis of hGH and MnSOD mRNA levels in rat lung epithelial cells transfected with pØGH vectors containing either the 3.8 Kb or the 2.3 Kb internal fragments of the rat MnSOD gene (FIG. 2A), and stimulated with LPS.

Furthermore, the 6.1 Kb Hind III internal MnSOD fragment was cleaved at the unique HpaI site, and the enhancer activity of the resulting 3.8 Kb and 2.3 Kb internal MnSOD fragments were tested using the pØGH vector. The cis-acting element responsible for the inducible activity was localized to the 3.8 Kb fragment, which represents the 5' half of the original 6.1 Kb HindIII fragment (FIG. 2C). Again, orientation did not influence the inducible activity in response to inflammatory mediators, thus indicating that this element has the properties of an enhancer.

Localization of the Novel MnSOD Inducible Enhancer Element within Intron 2

To further localize the region of the inducible cis-acting element within the 3.8 kb HindIII-HpaI MnSOD fragment, the polymerase chain reaction (PCR) was used to amplify serial deletion fragments (from both the 5' and 3' ends) spanning this region (FIG. 3A). Oligonucleotides complementary to regions of the 3.8 kb HindIII-HpaI fragment were generated containing restriction sites (HindIII or NedI) to facilitate cloning of the enhancer fragments into the pØGH vector containing the Hind/E fragment of the MnSOD promoter. The inducible enhancer activity was assessed by transient transfection of the pØGH vector constructs into L2 cells and northern analysis.

Figure 3B:
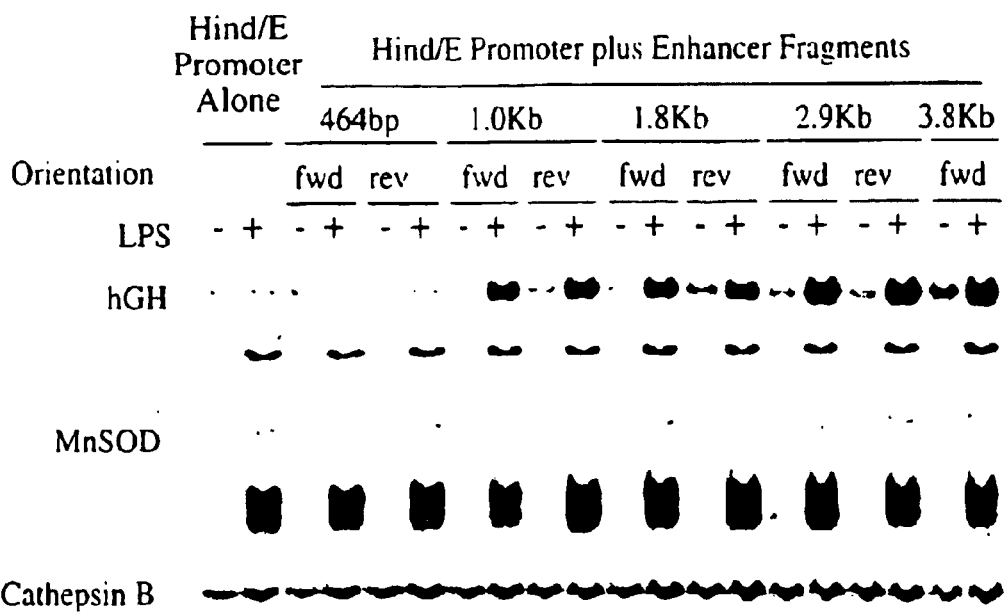
FIGS. 3B and 3C show a Northern analysis of hGH and MnSOD mRNA levels in rat lung epithelial cells transfected with pØGH vectors containing 3' deletion fragments of the 3.8 Kb internal enhancer fragment of the rat MnSOD gene, and stimulated with LPS.
Figure 3C:
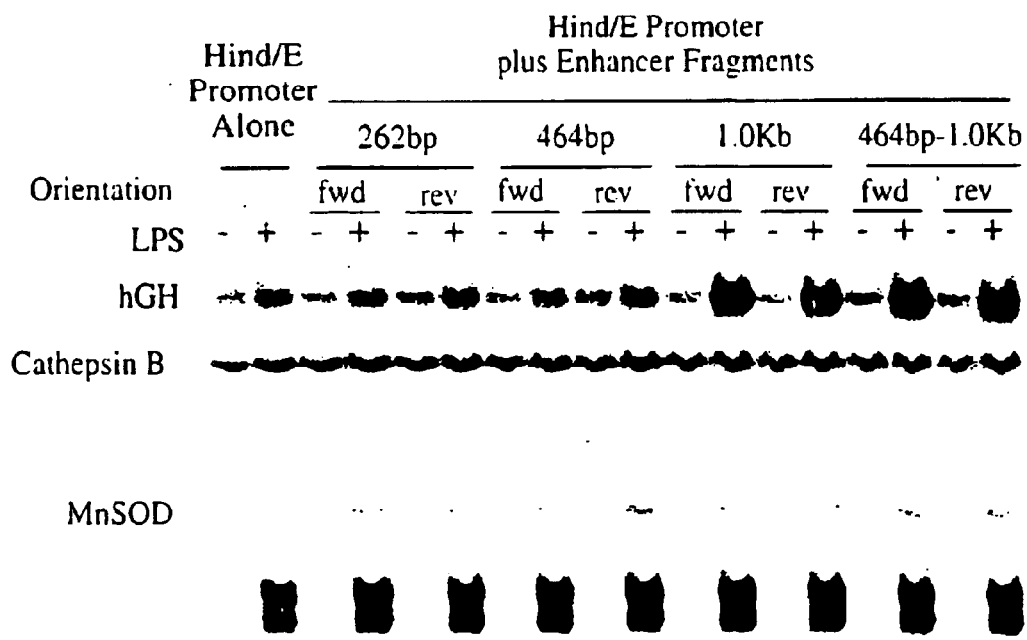
Figure 3D:
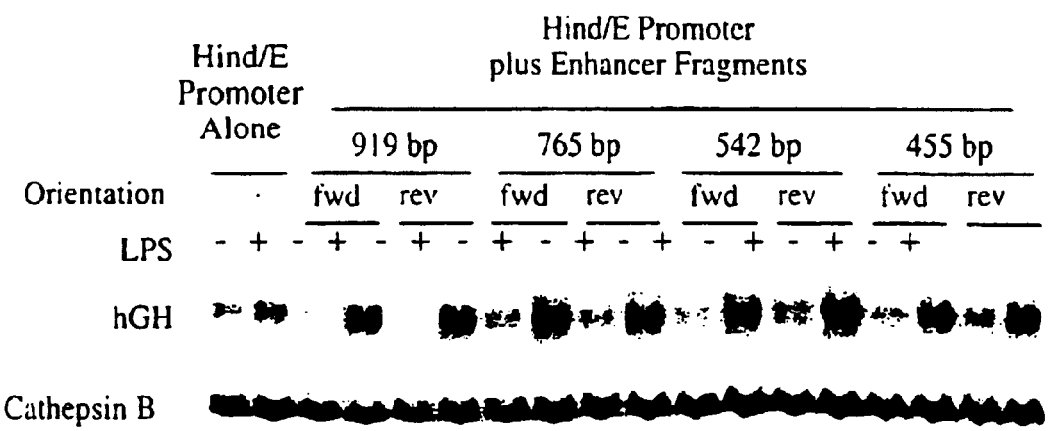
FIGS. 3D and 3E show a Northern analysis of hGH mRNA levels in rat lung epithelial cells transfected with pØGH vectors containing 5' deletion fragments of the 3.8 Kb internal enhancer fragment of the rat MnSOD gene, and stimulated with LPS.
Figure 3E:
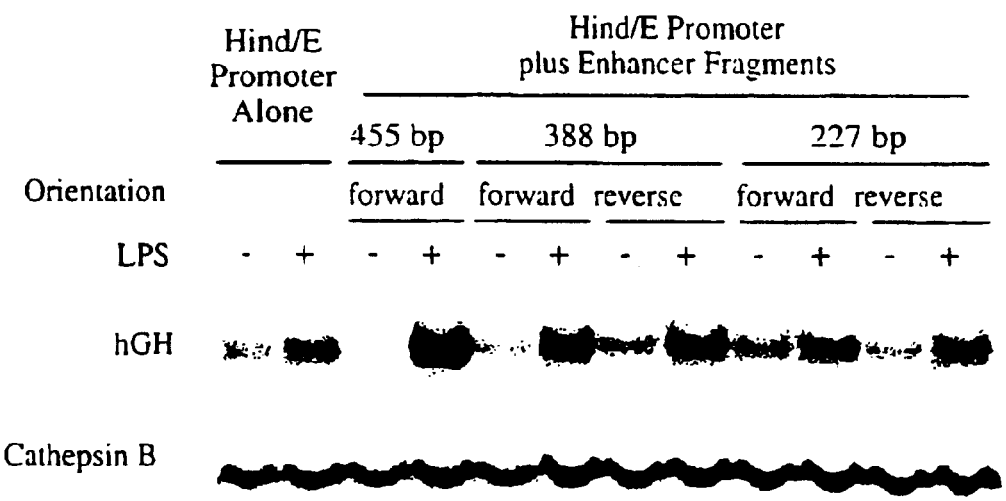

Multiple 3' and 5' deletions of the 3.8 kb HindIII-HpaI enhancer fragment demonstrated inducible activity that was comparable to the induction of endogenous MnSOD mRNA levels. Based on the 3' deletions of this 3.8 Kb internal MnSOD fragment, the inducible enhancer activity was localized to the 464 bp-1.0 Kb fragment in the 5' end of the fragment (FIGS. 3B and 3C). This position coincides to DNase hypersensitive site 2 close to the intron 2-exon 3 boundary. 5' deletion analysis of the 3.8 Kb internal MnSOD fragment indicated that the 338 bp and 227 bp fragments show reduced enhancer activity relative to the 455 bp fragment (FIGS. 3D and 3E). Taken together, these data indicate that the MnSOD enhancer activity regulated by LPS, TNF-α, and IL-1β appears to exist within a 200 to 300 bp region near the 3' end of intron 2.

The Enhancer is Composed of a Complex Set of Interacting Elements

Figure 4A:
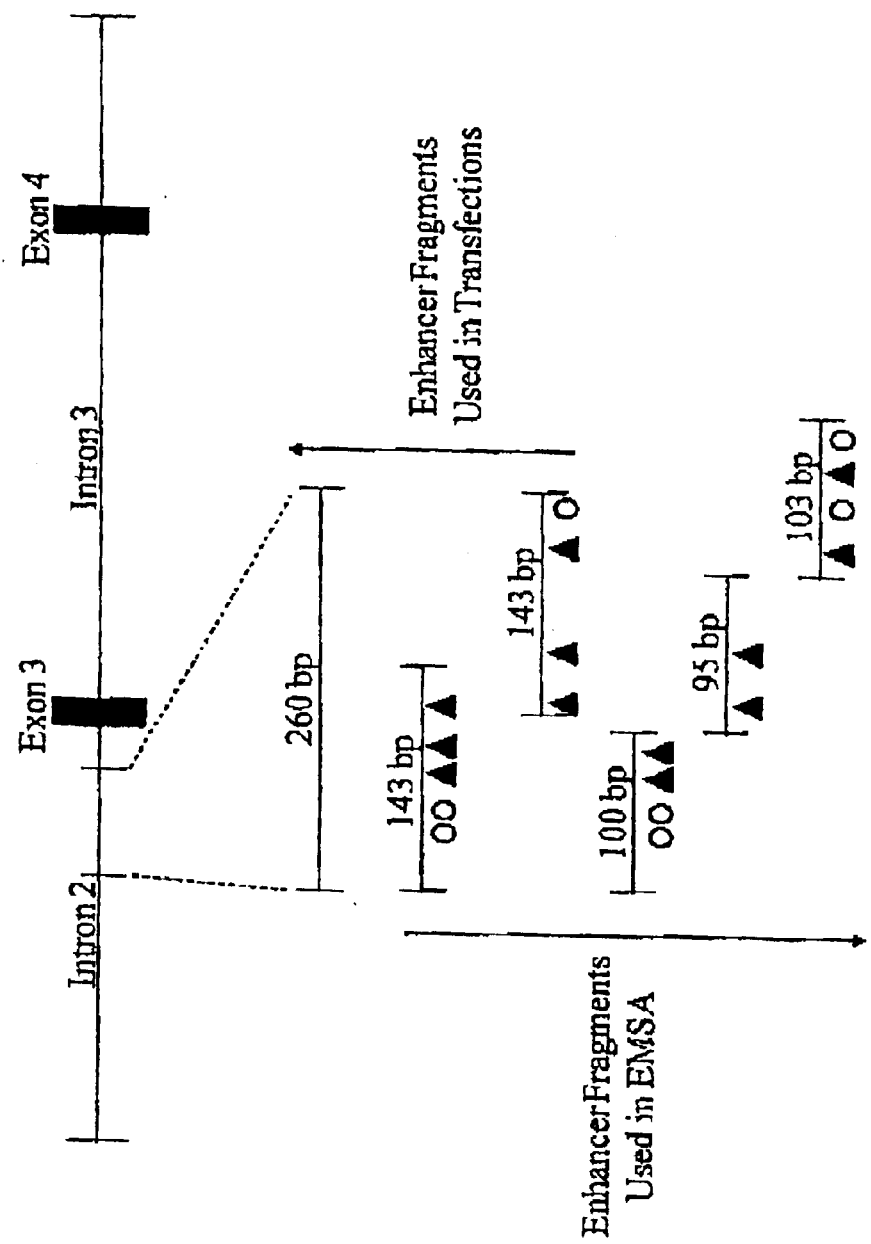
FIG. 4A shows a schematic representation of a 260 bp enhancer region in intron 2 of the rat MnSOD gene, and internal fragments of the enhancer region generated for transfection studies and electrophoretic mobility shift assays (EMSA). Putative constitutive and inducible protein binding sites are illustrated by open circles (○) and filled triangles (▲), respectively.
Figure 4B:
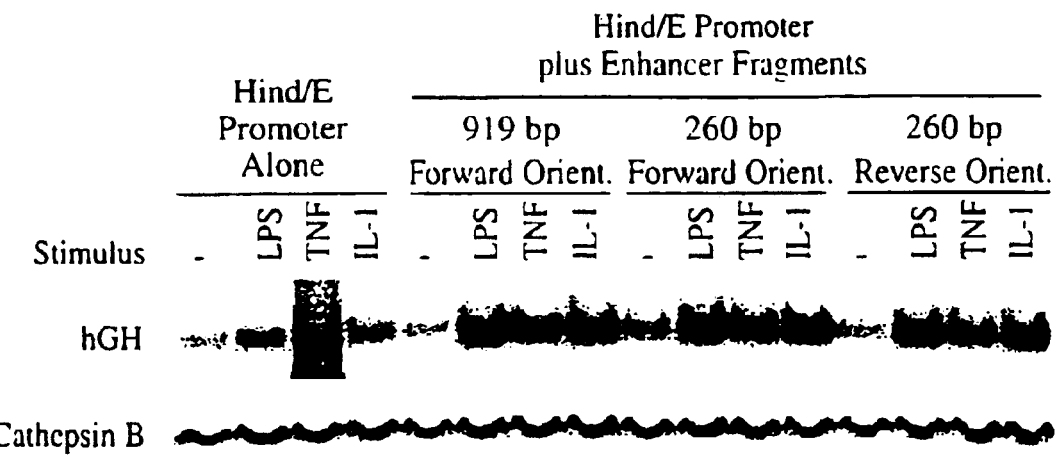
FIG. 4B shows a Northern analysis of hGH mRNA levels in rat lung epithelial cells transfected with the pØGH vector containing either the 919 bp (FIG. 3A) or the 260 bp fragment (FIG. 4A) of the MnSOD enhancer region, and stimulated with LPS, TNF-α, or IL-1β.
Figure 4C:
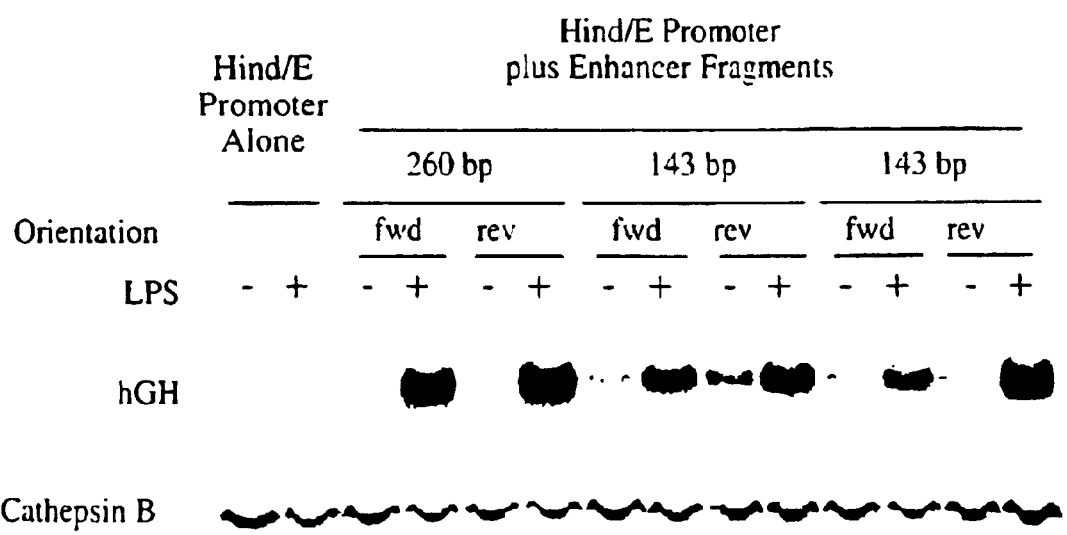
FIG. 4C shows a Northern analysis of hGH mRNA levels in rat lung epithelial cells transfected with the pØGH vector containing either the 260 bp MnSOD enhancer region, or the internal 143 bp fragments (FIG. 4A) of the 260 bp MnSOD enhancer, and stimulated with LPS.

To further characterize the enhancer within the 3' region of intron 2 of the rat MnSOD gene additional deletion constructs were created which contained either 260 bp or 143 bp fragments of the intron 2 region. PCR amplification was used to generate a 260 bp fragment spanning the region between the two 5' deletions (455 bp and 227 bp) shown in FIG. 3A, as well as two 143 bp fragments which overlap each other within this 260 bp fragment (FIG. 4A). This region was felt to contain the entire regulatory sequence responsive to LPS, TNF-α, and IL-1β. The ability of these fragments to cause inducible expression was evaluated by transient transfection and northern analysis. The 260 bp fragment contained all the enhancer activity seen in the larger 919 bp fragment (FIG. 4B), and retained responsiveness to all of the inflammatory mediators (e.g., LPS, TNF-α, and IL-1β). The two 143 bp fragments retain enhancer activity, although possibly less than the full 260 bp region (FIG. 4C). These results are consistent with the deletion analysis, which showed partial enhancer activity in the 338 bp fragment compared to the 455 bp fragment, and a total loss of activity with the 227 bp fragment (FIG. 3E). This is also consistent with the fact that the 260 bp fragment spans the region between the 455 bp deletion fragment and the 227 bp deletion fragment (FIG. 3A). Taken together, the results summarized in FIGS. 3E and 4C demonstrate that the 260 bp fragment delineates the minimum functional boundaries of the MnSOD enhancer.

Figure 4D:
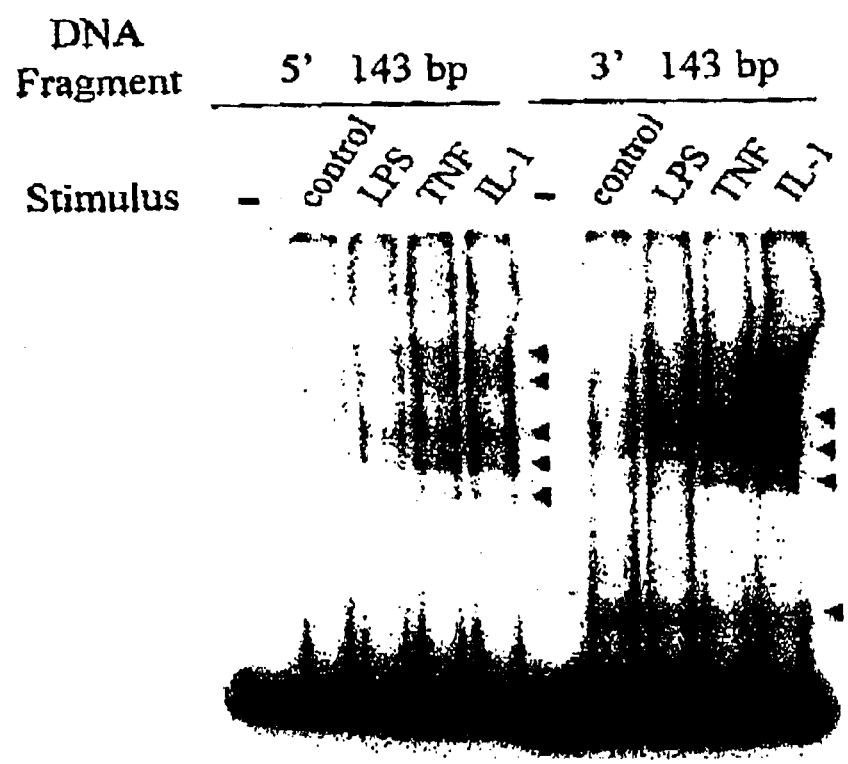
FIGS. 4D and 4E show an EMSA analysis of protein binding within the MnSOD enhancer region. Internal fragments of the 260 bp enhancer region of the rat MnSOD gene (FIG. 4A) were used as probes, and incubated with nuclear extracts from untreated cells and cells treated with LPS, TNF-α, and IL-1β. DNA-protein complexes are indicated by arrowheads (◄).
Figure 4E:
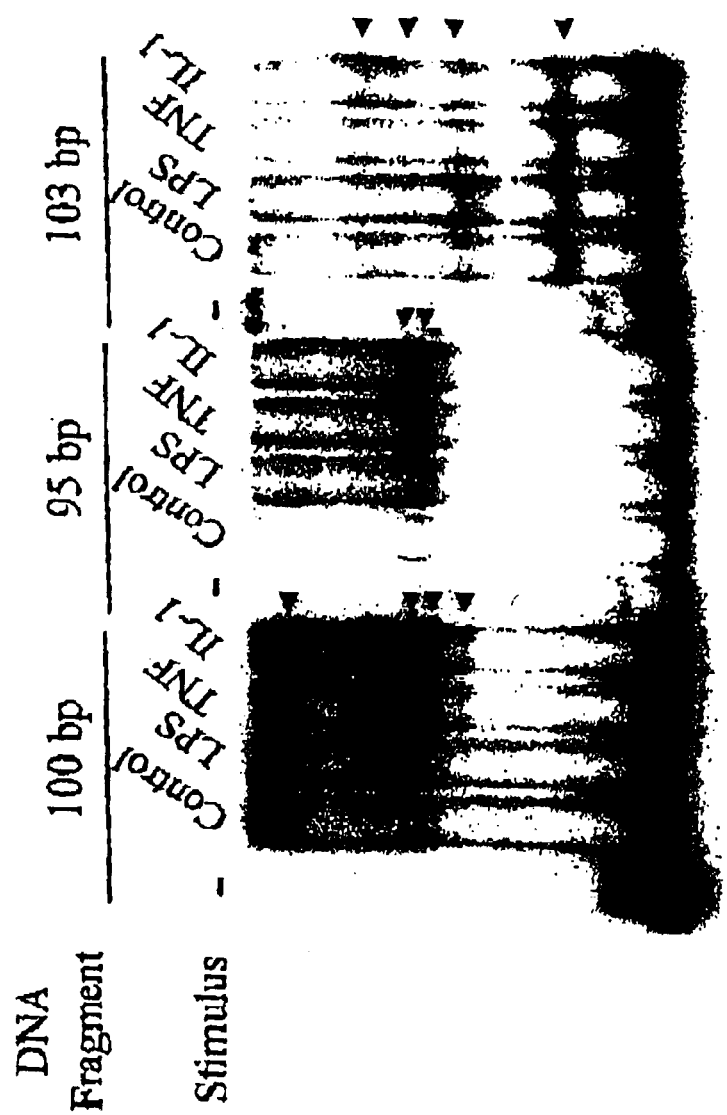

To evaluate protein binding to the MnSOD enhancer elements, electrophoretic mobility shift assays were performed with nuclear extracts from control and treated (LPS, TNF-α, IL-1β) cells. FIG. 4D shows the difference in the protein binding patterns between treated and control nuclear extracts as well as the different patterns of m protein binding between the two functional 143 bp DNA fragments that comprise the enhancer element. Constitutive protein binding is observed in the 3' 143 bp fragment, but several inducible DNA-protein complexes can be appreciated in both fragments. In an attempt to further localize the protein binding sites, smaller fragments of the enhancer region were generated by PCR and evaluated by electrophoretic mobility shift assays (FIG. 4E). Once again, constitutive protein binding was observed in the 100 bp and 103 bp fragments. However, as with the 143 bp fragments, inducible protein binding was also observed in two of the smaller fragments (100 bp and 95 bp), most notably in the 95 bp fragment which shows a dramatic difference in binding between control and treated nuclear extracts. Further localization of protein binding was attempted with 50 bp and 30 bp fragments from the enhancer region, however, stimulus specific protein-DNA complexes were not observed. Therefore, protein-protein interactions are most likely a prerequisite for specific DNA binding, thus explaining the loss of stimulus-specific protein-DNA interactions in the smaller deletions of this complex regulatory element.

The Rat and Human MnSOD Gene Enhancers Act with a Heterologous Promoter

Sequence analysis identified a high level of homology between the sequence of intron 2 of the rat MnSOD gene, comprising the enhancer element, and the corresponding region in the human MnSOD gene (FIG. 5).

Figure 6B:
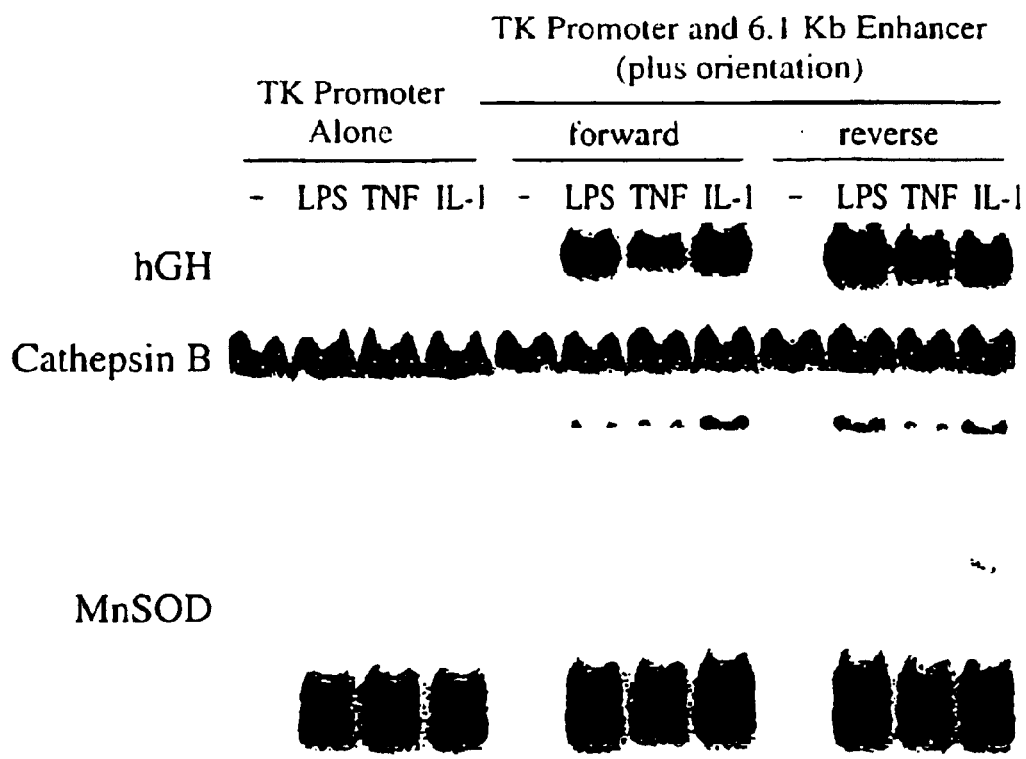
FIG. 6B shows a Northern analysis of hGH and MnSOD mRNA levels in rat lung epithelial cells transfected with the pTKGH vector containing the 6.1 Kb internal Hind III fragment of the rat MnSOD gene (FIG. 2A), and stimulated with LPS, TNF-α, or IL-1β.

To determine whether the MnSOD, enhancers could function with a heterologous promoter, rat and human enhancer fragments were cloned into the pTKGH expression vector (FIG. 6A). The herpes virus thymidine kinase promoter in this vector is a 200 bp minimal, TATA containing promoter, quite dissimilar unlike the GC-rich, TATA- and CAAT-less MnSOD promoter. Results of transient transfections and northern analysis of the 6.1 kb HindIII internal MnSOD fragment in pØGH showed that the rat cis-acting enhancer element dramatically increased transcriptional activity in response to inflammatory mediators (FIG. 6B). Cells treated with LPS, TNF-α, and IL-1β had marked levels of hGH mRNA in comparison with almost undetectable levels in control, untreated cells. The rat MnSOD enhancer element functioned equally well in both orientations. The ability of this novel element to enhance transcriptional activity of a heterologous promoter in an orientation-independent and position-independent manner further qualifies it as an enhancer element.

Figure 6C:
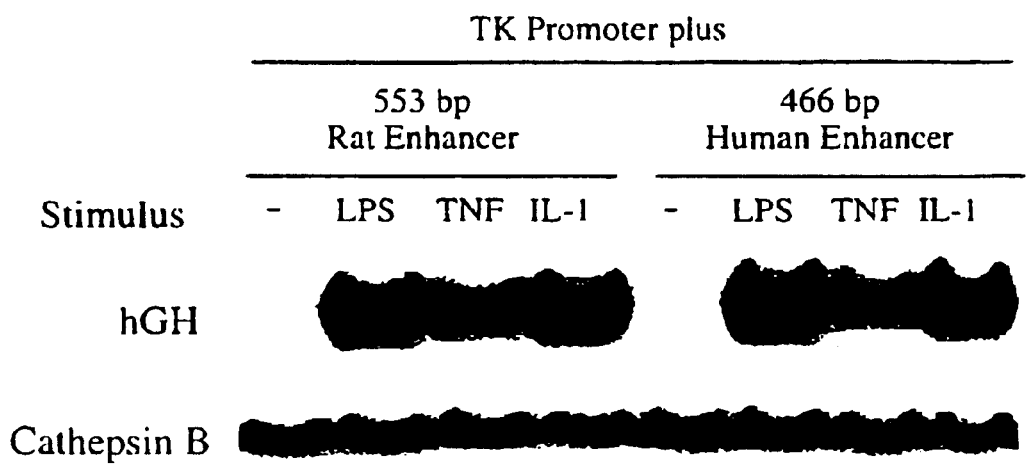
FIG. 6C shows a Northern analysis of hGH mRNA levels in rat lung epithelial cells transfected with the pTKGH vector containing either a 553 bp fragment containing the rat MnSOD enhancer, or a 466 bp fragment containing the human MnSOD enhancer, and stimulated with LPS, TNF-α, or IL-1β.

In order to evaluate the functional significance of the homologous human MnSOD enhancer region, a 553 bp fragment of the rat enhancer and an analogous 466 bp region (generated by PCR amplification from human genomic DNA) from intron 2 of the human MnSOD gene were inserted into the pTKGH vector. The ability of the fragments to cause inducible enhancer activity was assessed by transient transfection and northern analysis. Both the rat and the human MnSOD enhancer fragments promoted essentially identical inducible gene expression in response to LPS, TNF-α and IL-1β (FIG. 6C), indicating that the analogous region of intron 2 of the human MnSOD gene likely acts as an enhancer in the endogenous gene, and that the enhancer element itself is well conserved between species.

Figure 7:
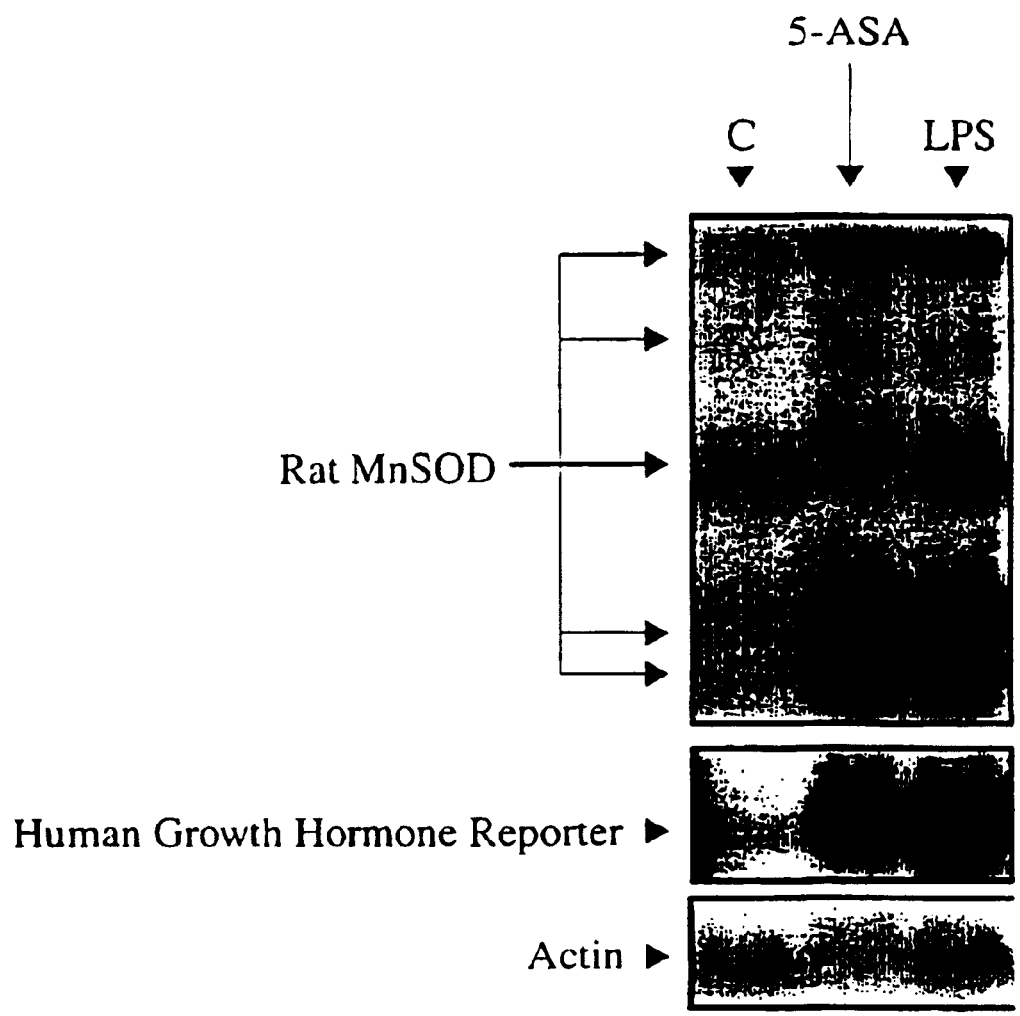
FIG. 7 shows a Northern analysis of hGH and MnSOD mRNA levels in rat intestinal epithelial cells transfected with the pTKGH vector containing a 508 bp fragment containing the MnSOD enhancer.

Rat intestinal epithelial cells were also transfected with a pTKGH vector containing a 508 bp fragment of the MnSOD enhancer element and treated with both mesalamine (5-ASA, 2 mg/ml) and LPS (0.5 µg/ml) for 8 hours. Total RNA was isolated and rat MnSOD and hGH mRNA levels were evaluated by northern analysis (FIG. 7). Both endogenous MnSOD and the human growth hormone reporter gene were induced by mesalamine and LPS in an identical fashion, indicating that the enhancer element is responsive to both endogenous inflammatory stimuli as wells exogenous pharmaceutical compositions.

Characterization of MnSOD Promoter-enhancer Interactions

Figure 8A:
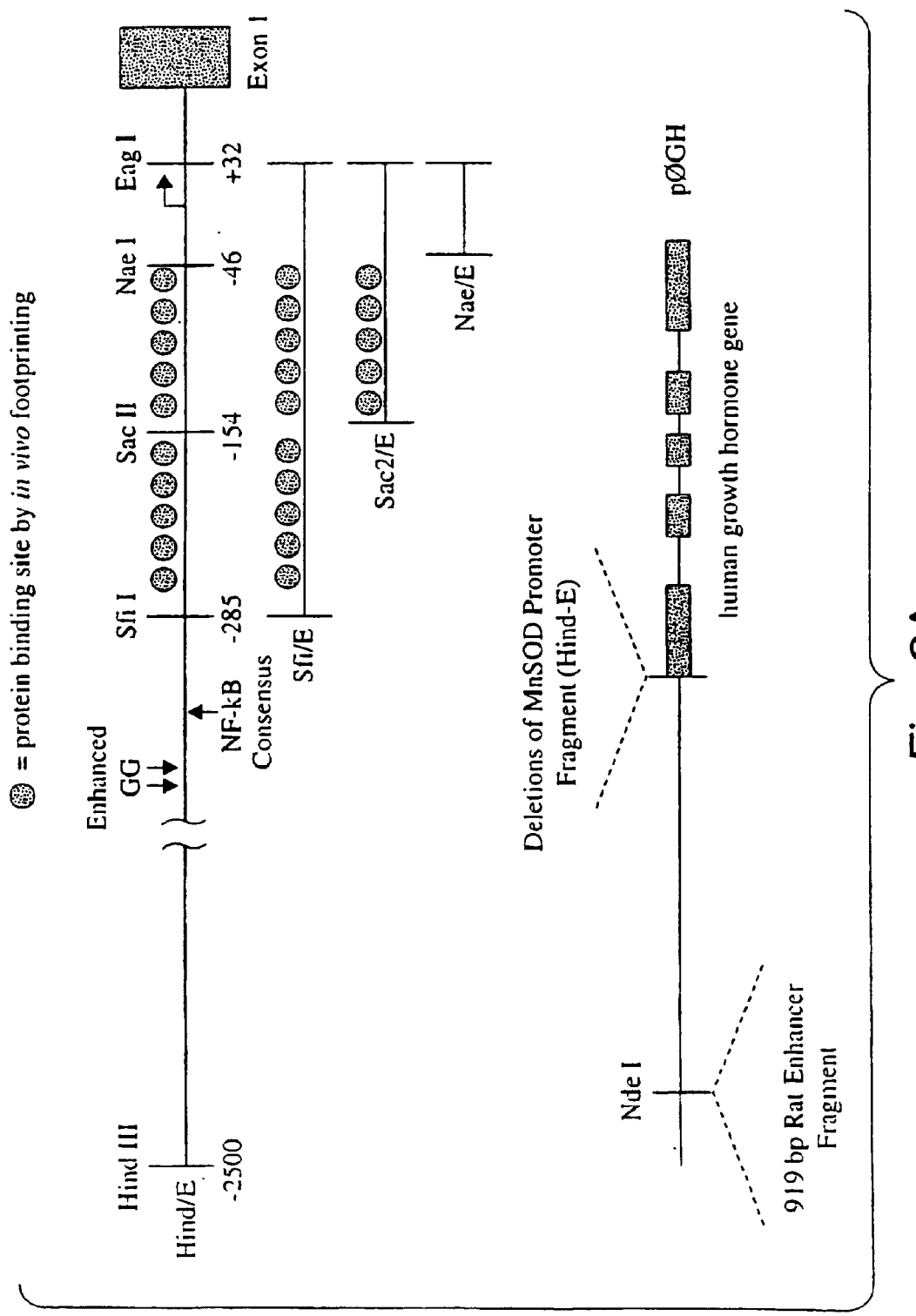
FIG. 8A shows a schematic representation of deletion fragments of the rat MnSOD promoter, indicating protein binding sites found by in vivo footprinting (●). Placement of the promoter deletion fragments 5' to the human growth hormone reporter gene in the promoterless human growth hormone vector (pØGH) containing the rat MnSOD enhancer fragment is indicated.
Figure 8B:
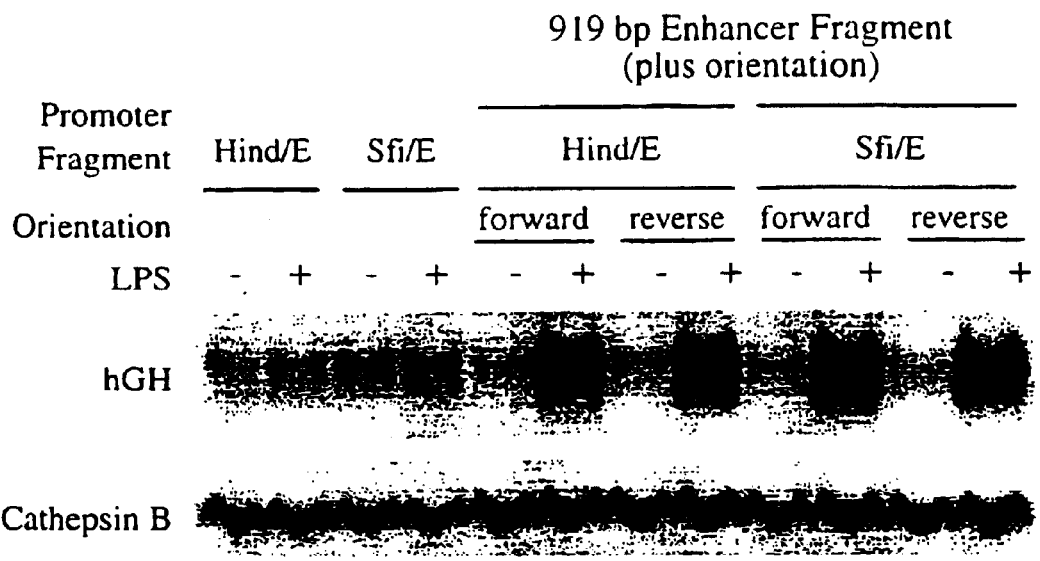
FIGS. 8B and 8C show a Northern analysis of hGH mRNA levels in rat lung epithelial cells transfected with the pØGH vector containing the rat MnSOD enhancer and promoter deletion fragments of the rat MnSOD gene (FIG. 6A), and stimulated with LPS.
Figure 8C:
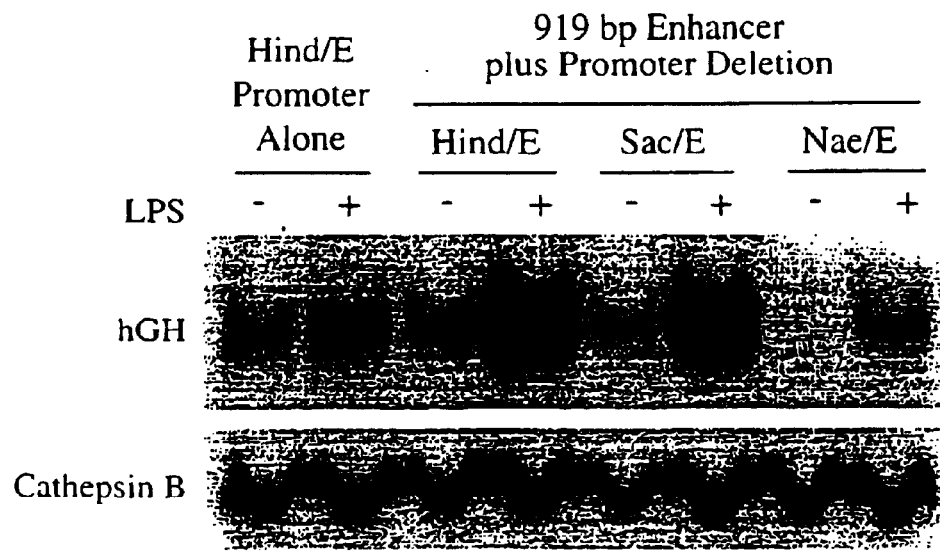

In vivo footprinting has demonstrated that the MnSOD 5' proximal promoter (described in Example 1) contains 10 potential protein binding sites. These sites are illustrated in FIG. 8A relative to the restriction sites that were employed for the promoter deletion analysis ((●), FIG. 1A). To define the areas within the MnSOD promoter required for interaction with the enhancer element, the rat MnSOD promoter deletion constructs were coupled with a 919 bp enhancer fragment in the pØGH vector (FIG. 8A). Transient transfection and northern analysis were used to evaluate the inducible activity of these constructs. The five most distal protein binding sites in the MnSOD 5' proximal promoter could be deleted without any detectable decrease in inducible activity (FIGS. 8B and 8C). However, when the remaining five proximal binding sites in the MnSOD 5' proximal promoter were eliminated, almost complete basal activity was lost (FIG. 8C). LPS-inducible transcription could still occur when all of the protein binding sites in the MnSOD promoter were deleted (Nae/E deletion construct), but only when the vector construct contained the 919 bp enhancer fragment (FIG. 8C). In the absence of the enhancer element, deletion of the same promoter region eliminated any transcription (FIGS. 1B and 1C). These studies demonstrate that a minimal MnSOD promoter deletion fragment (Nae/E) is not capable of supporting significant levels of transcription by itself, but can support inducible transcription when coupled to the MnSOD enhancer.

Figure 9A:
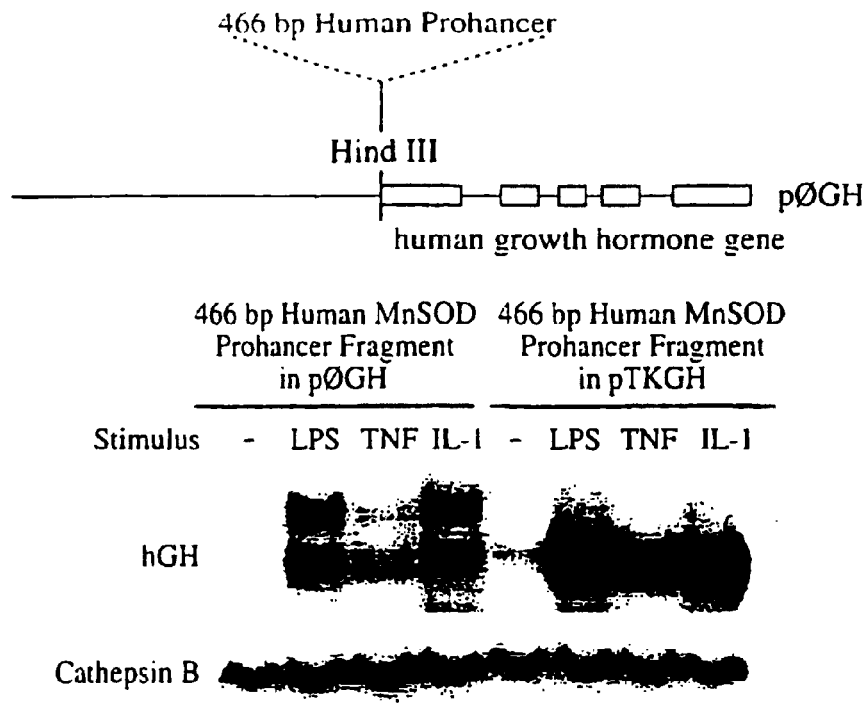
FIG. 9A shows a schematic representation of the promoter-less human growth hormone vector (pØGH) and the position of the human 466 bp MnSOD prohancer fragment. Northern analysis of hGH mRNA levels in rat lung epithelial cells transfected with the pØGH vector containing the human 466 bp MnSOD prohancer, and stimulated with LPS, TNF-α, or IL-1β.
Figure 9B:
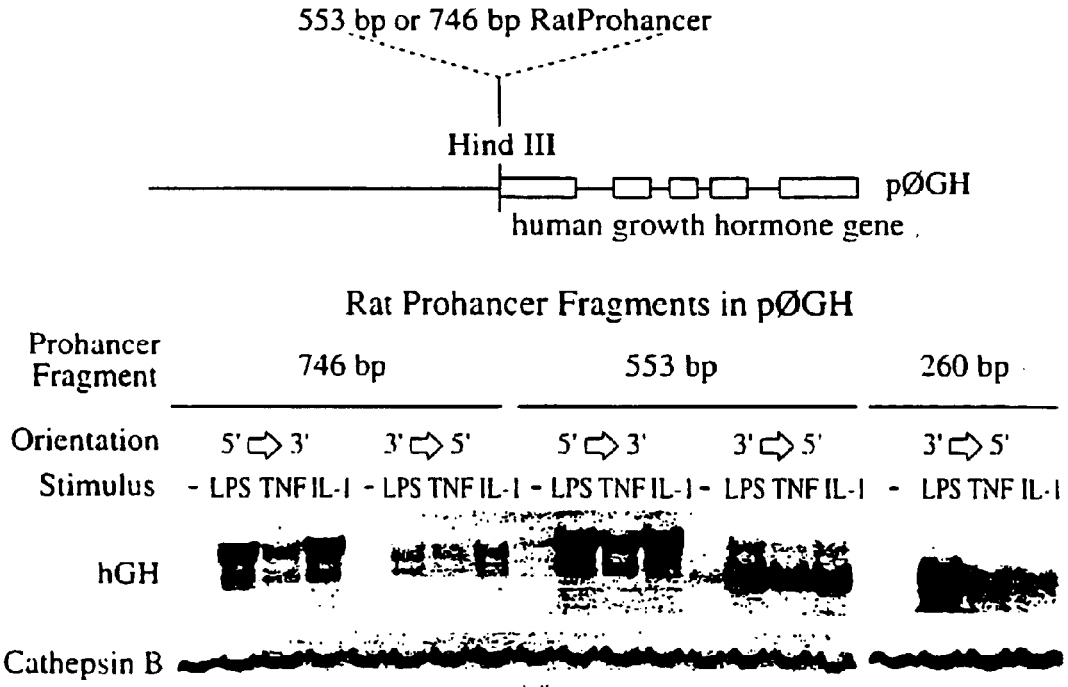
FIG. 9B shows a schematic representation of the promoter-less human growth hormone vector (pØGH) and the position of the rat 746 bp, 553 bp and 260 bp MnSOD prohancer fragments. Northern analysis of hGH mRNA levels in rat lung epithelial cells transfected with the pØGH vector containing the rat MnSOD prohancer fragments, and stimulated with LPS, TNF-α, or IL-1β.

Characterization of Rat and Human MnSOD Enhancer Elements as Additionally Having Promoter Activity To determine whether the MnSOD enhancer element might exhibit stimulus-dependent promoter activity in the absence of a true promoter, the rat and the human enhancer elements were inserted into the promoterless pØGH vector and the pTKGH vector (FIGS. 9A and 9B). FIG. 9A shows the results of the 466 bp human MnSOD enhancer fragment in the presence (pØGH) and absence (PTKGH) of the TK promoter. The MnSOD enhancer alone mediated inducible transcription in response to LPS, TNF-α and IL-1β stimulation, but at lower levels than when the enhancer was coupled with the TK promoter. Interestingly, two transcripts, one the correct size and one larger, were seen when the human 466 bp enhancer fragment acted as its own promoter. When the 553 bp and 746 bp rat enhancer fragments were tested in the pØGH vector, similar results to the human enhancer element were obtained, in that, two different-sized transcripts were observed (FIG. 9B). Of note, however, is that when the 553 bp fragment containing the enhancer was inserted in front of the hGH gene in the 3'→5' orientation, the correct-sized transcript predominated. Furthermore, as can be seen in FIG. 7B, when the rat 260 bp enhancer fragment acting as a promoter was inserted into the pØGH vector in the 3'→5' orientation, a single stimulus-responsive transcript of the correct size resulted.

These studies indicate that the MnSOD enhancer can indeed act independently as a promoter, and that orientation and position relative to the start of transcription were important for promoter function. The finding that the MnSOD enhancer has both inducible enhancer and promoter activity is also referred to herein as the identification of a novel prohancer element.

Discussion

Extensive studies have been performed on the molecular regulation of the MnSOD gene in a variety of mammalian cells including: pulmonary endothelial (Visner et al., 1992) and epithelial cells (Visner et al., 1990); intestinal epithelial (Valentine and Nick, 1992), smooth muscle (Tannahill et al., 1997) and myenteric neurons (Valentine et al., 1996); mesangial (Stephanz et al., 1996) and glomerular epithelial cells (Gwinner et al., 1995); neurons and glial cells (Kifle et al., 1996); as well as primary hepatocytes cultures (Dougall and Nick, 1991).

In many cells, MnSOD levels are dramatically induced by LPS, IL-1β, and TNF-α with induction levels ranging from 15–100 fold depending on the cell type (FIG. 12). One exception is that hepatocytes show responses primarily with IL-6 and INF-γ. The extension of these results has led to the identification of an extremely potent enhancer element, described herein, which mediates the regulation of the MnSOD gene in an LPS-IL-1β-, and TNF-α-dependent manner. This element can function in an orientation and position independent manner, and also retains the ability to function as a totally independent stimulus-responsive promoter. In addition, this element has been evolutionarily conserved between rodents and man.

Another characteristic of this enhancer is its ability to function with a TATA- and CAAT-box containing minimal promoter, whereas the endogenous MnSOD promoter lacks these elements. The potency of the enhancer is increased with a minimal viral thymidine kinase promoter, exhibiting stimulus-specific induction levels of up to 45 fold. Given the inducibility, minimal size, and stimulus-specificity of this enhancer, it appears to be an ideal regulatory element for gene therapy. The inherent ability of this element to respond to IL-1β and TNF-α will allow this enhancer to drive transgene expression, when and only when endogenous levels of IL-1β and TNF-α are increased. Therefore, the transgene expression will directly mimic the changes in cellular IL-1β and TNF-α levels, which occur during acute and chronic inflammation. Moreover, this enhancer element will also respond during inflammatory situations associated with bacterial infections where systemic LPS concentrations presumably increase, analogous to *Pseudomonas aeruginosa* colonization in cystic fibrosis patients.

Example 3

Figure 10:
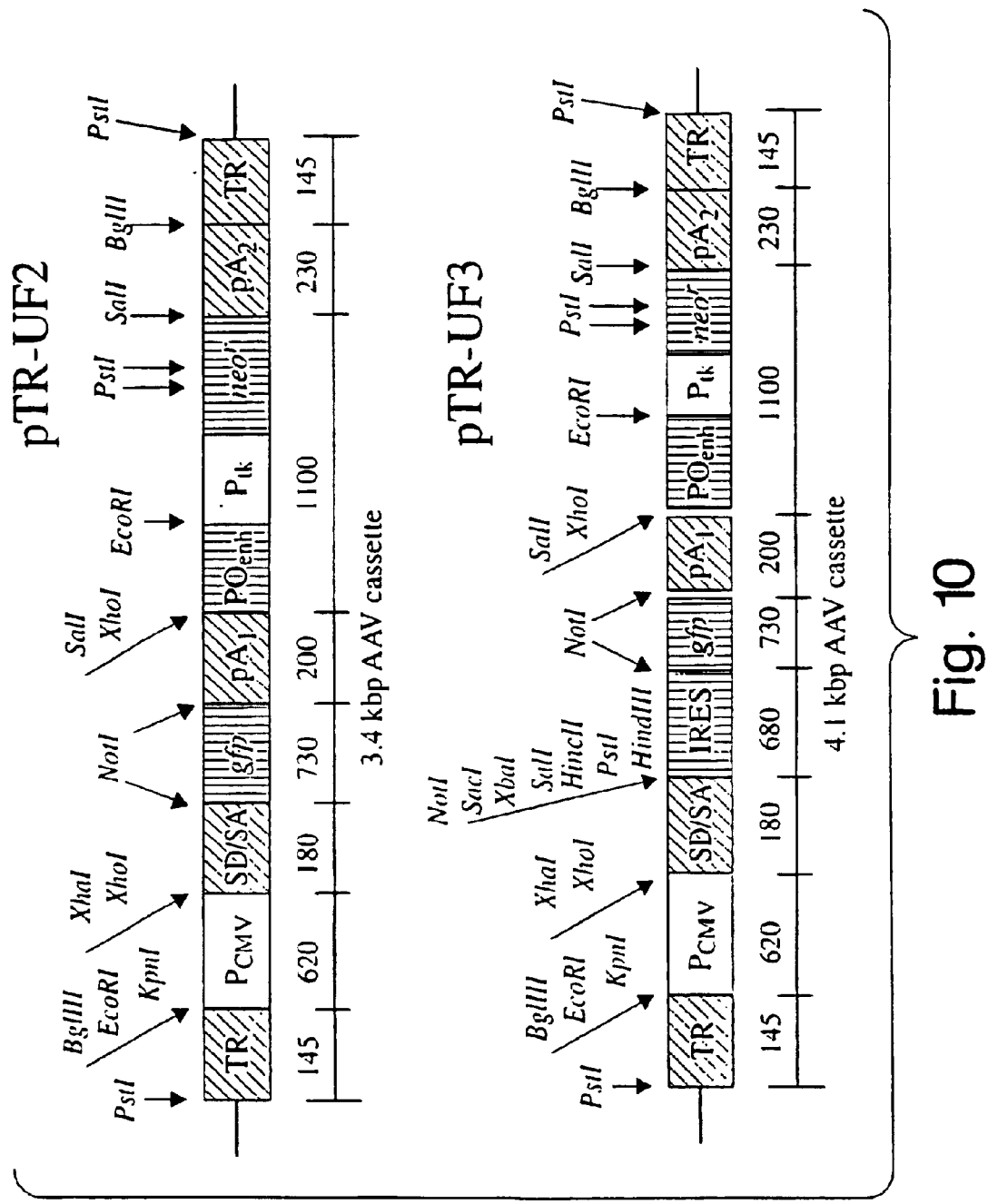
FIG. 10 shows restriction maps of the pTR-UF (User Friendly) series of AAV vector plasmids constructed by the Vector Core at the University of Florida, pTR-UF2 and pTR-UF3 contain the jellyfish gfp cDNA sequence with a humanized codon preference, pTR-UF3 is identical to pTR-UF2 except that pTR-UF3 has a poliovirus IRES element that allows the construction of bicistronic genes.

Construction of Recombinant Adeno-AssociatedVirus (AAV) Vectors Containing MnSOD Prohancer Elements The novel MnSOD prohancer elements of the invention can also be used to generate delivery vectors suitable for inducible heterologous gene expression. A series of AAV vectors can be engineered containing the MnSOD prohancer element. To do this, the $P_{CMV}$ promoter is removed from pTR-UF2 using KpnI and XhaI, and the MnSOD prohancer, either alone or coupled to a minimal promoter, is inserted (FIG. 10). The recombinant AAV plasmids are packaged using the current method for isolating rAAV as developed by Hermonat and Muzyczka (1984). Human cells (e.g., 293 cells) are transfected with the plasmid which consists of a transgene flanked by the AAV terminal repeats (TR), the only AAV sequences required for viral DNA replication, packaging and integration. The cells are also transfected with a complementing plasmid that is defective for packaging, but supplies the wild type AAV rep and cap genes in trans. Finally, the cells are infected with adenovirus to supply the adenovirus helper functions, E1A, E1B, E2A, E4, and VA. The rAAV virus stock produced contains both adenovirus and the AAV recombinant virus.

A fast and reproducible protocol has developed for the purification and concentration of rAAV. This protocol is based on partial purification of the initial freeze/thaw lysate by ammonium sulfate fractionation, followed by ion exchange batch chromatography and a final CsCl gradient centrifugation step. The helper Ad virus is eliminated by heat-inactivation early in the process and is no longer present as a distinct band in the CsCl gradient. A PCR based assay is employed to monitor rAAV-positive fractions from the CsCl gradient. The final rAAV stock is titered by the infectious center assay and a QC-PCR assay. By optimizing the transfection protocol, the time of addition of adenovirus, the pH of the extraction buffer, and the method of purification, a typical yield is about 30–50 infectious units per cell. A preparative isolation from a total of twenty 15 cm tissue culture dishes provides a final yield of approximately $10^{10}$ infectious units of rAAV in a total volume of 0.5 ml. Quality control assays for purity and infectivity are performed, as appropriate.

Packaged vectors are used to transduce cell cultures (e.g., A549 cells and astrocyte cultures) at a multiplicity of 1, 10 and 100 infectious units per cell. Cells are selected with G418 at 2 to 3 days after transduction. Selection is continued for 10 days followed by isolation of individual clones using cloning cylinders. Green fluorescent protein (GFP) will be assayed using phase contrast and epifluorscence microscopy followed by northern analysis to detect the GFP message. The AAV cassette in vector pTR-UF3 may also be used (FIG. 10), which allows for a dicistronic expression system in which the $P_{CMV}$ promoter is removed and the MnSOD prohancer element inserted, and a transgene of interest is inserted via the multiple cloning sites in the flanking polio IRES element.

Figure 11:
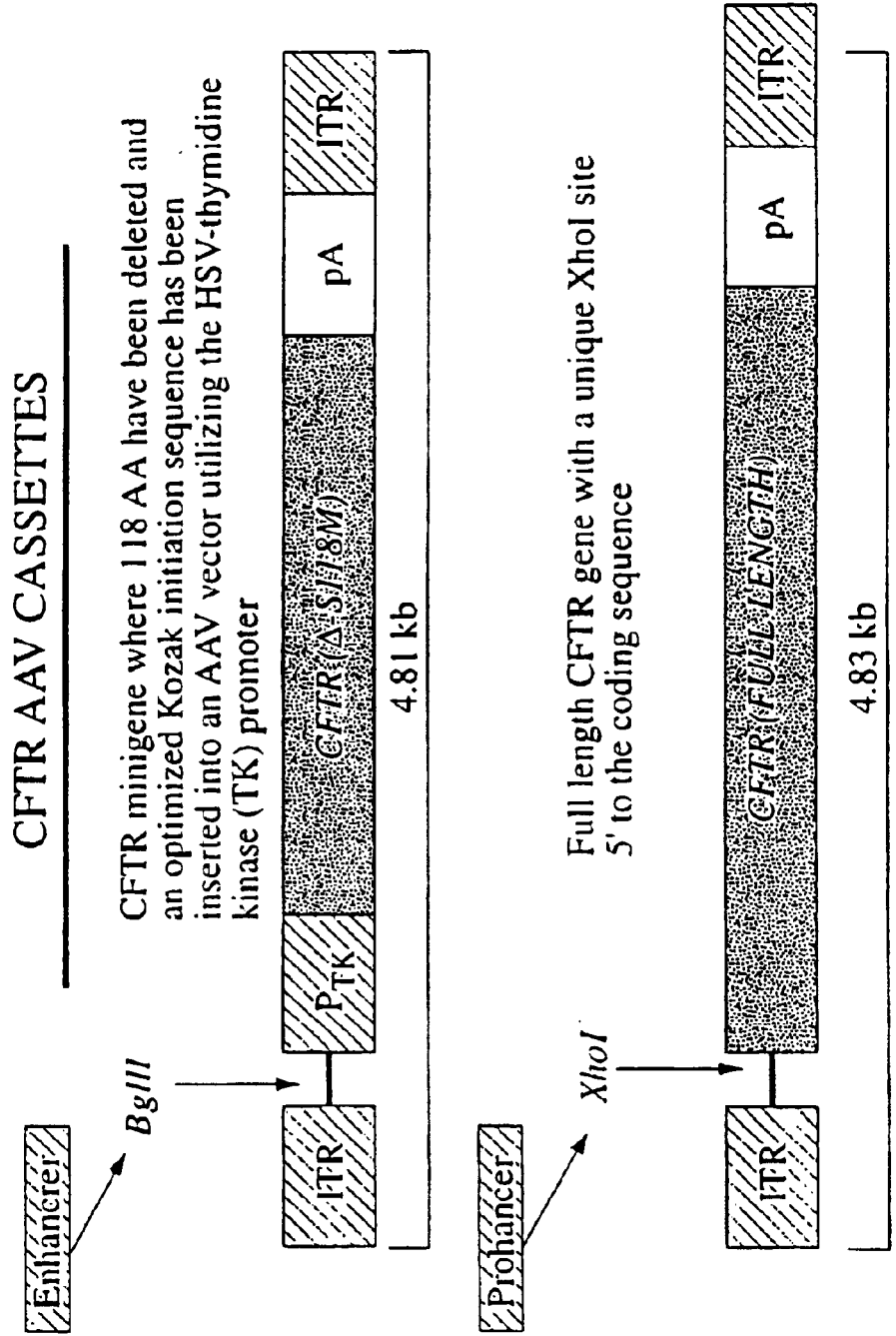
FIG. 11 shows AAV vectors developed for gene targeting of CFTR.

AAV vectors are employed for gene targeting of candidate genes (e.g., CFTR) that are ideally suited to test the unique characteristics of the "prohancer" (FIG. 11). One of the difficulties associated with the use of AAV in cystic fibrosis is the packaging limit of the virion (~5 kb), based on the large size of the CFTR coding sequence. To address this issue, a CFTR minigene has been generated with a 118 amino acid deletion which retains 75% of the channel activity as confirmed by using $^{36}Cl^-$ isotope tracer efflux. The 260 bp MnSOD enhancer element may be inserted in the unique BglII site 5' to the minimal TK promoter already incorporated in this vector. An alternative construct involves the ligation of the prohancer into a unique XhoI site 5' to the full length CFTR coding region. It is possible that with the incorporation of the 260 bp prohancer fragment that this rAAV vector (5.09 kb) will be larger than the packaging limit of the AAV virion. Given this possibility, exonuclease digestion of the XhoI digested vector may be used to eliminate 120–145 bp of vector sequence between the left ITR and the beginning of the CFTR coding sequence, followed by a blunt-end ligation of the prohancer element. These constructs are packaged, produced on a large scale and subsequently transduced into cells, as described above.

References

U.S. Pat. No. 3,791,932, issued Feb. 12, 1974.
U.S. Pat. No. 3,949,064, issued Apr. 6, 1976.
U.S. Pat. No. 4,174,384, issued Nov. 13, 1979.
U.S. Pat. No. 4,196,265, issued Apr. 1, 1980.
U.S. Pat. No. 4,237,224, issued Dec. 2, 1980.
U.S. Pat. No. 4,271,147, issued Jun. 2, 1981.
U.S. Pat. No. 4,329,332, issued May 11, 1982.
U.S. Pat. No. 4,352,883, issued Oct. 5, 1982.
U.S. Pat. No. 4,358,535, issued Nov. 9, 1982.
U.S. Pat. No. 4,489,055, issued Dec. 18, 1984.
U.S. Pat. No. 4,514,498, issued Apr. 30, 1985.
U.S. Pat. No. 4,554,101, issued Nov. 19, 1985.
U.S. Pat. No. 4,578,770, issued Mar. 25, 1986.
U.S. Pat. No. 4,596,792, issued Jun. 24, 1986.
U.S. Pat. No. 4,599,230, issued Jul. 8, 1986.
U.S. Pat. No. 4,599,231, issued Jul. 8, 1986.
U.S. Pat. No. 4,601,903, issued Jul. 22. 1986.
U.S. Pat. No. 4,608,251, issued Aug. 26, 1986.
U.S. Pat. No. 4,683,195, issued Jul. 28, 1987.
U.S. Pat. No. 4,683,202, issued Jul. 28, 1987.
U.S. Pat. No. 4,740,467, issued Apr. 26, 1988.
U.S. Pat. No. 4,795,804, issued Jan. 3, 1989.
U.S. Pat. No. 4,800,159, issued Jan. 24, 1989.
U.S. Pat. No. 4,877,864, issued Oct. 31, 1989.
U.S. Pat. No. 4,883,750, issued Nov. 28, 1989.
U.S. Pat. No. 4,913,908, issued Apr. 3, 1990.
U.S. Pat. No. 4,952,496, issued Aug. 28, 1990.
U.S. Pat. No. 4,965,188, issued Oct. 23, 1990.
U.S. Pat. No. 4,968,590, issued Nov. 6, 1990.
U.S. Pat. No. 5,011,691, issued Apr. 30, 1991.
U.S. Pat. No. 5,013,649, issued May 7, 1991.
U.S. Pat. No. 5,106,748, issued Apr. 21, 1992.
U.S. Pat. No. 5,108,753, issued Apr. 28, 1992.
U.S. Pat. No. 5,108,922, issued Apr. 28, 1992.
U.S. Pat. No. 5,116,738, issued May 26, 1992.
U.S. Pat. No. 5,139,941, issued Aug. 18, 1992.
U.S. Pat. No. 5,141,905, issued Aug. 25, 1992.
U.S. Pat. No. 5,166,058, issued Nov. 24, 1992.
U.S. Pat. No. 5,168,050, issued Dec. 1, 1992.
U.S. Pat. No. 5,176,995, issued Jan. 5, 1993.
U.S. Pat. No. 5,187,076, issued Feb. 16, 1993.
U.S. Pat. No. 5,354,855, issued Oct. 11, 1994.
U.S. Pat. No. 5,359,046, issued Oct. 25, 1994.
U.S. Pat. No. 5,399,346, issued Mar. 21, 1995.
U.S. Pat. No. 5,451,410, issued Sep. 19, 1995.
U.S. Pat. No. 5,478,745, issued Dec. 26, 1995
U.S. Pat. No. 5,500,224, issued Mar. 19, 1996.
U.S. Pat. No. 5,556,617, issued Sep. 17, 1996.
U.S. Pat. No. 5,620,708, issued Apr. 15, 1997.
U.S. Pat. No. 5,641,515, issued Jun. 24, 1997.
U.S. Pat. No. 5,698,515, issued Dec. 16, 1997.
U.S. Pat. No. 5,700,922, issued Dec. 23, 1997.
U.S. Pat. No. 5,741,683, issued Apr. 21, 1998.
U.S. Pat. No. 5,753,500, issued May 19, 1998.
U.S. Pat. No. 5,773,289, issued Jun. 30, 1998.
Intl. Pat. Appl. Publ. No. PCT/US87/00880.
Intl. Pat. Appl. Publ. No. PCT/US89/01025.
Intl. Pat. Appl. Publ. No. WO 88/10315.
Intl. Pat. Appl. Publ. No. WO 89/06700.
Intl. Pat. Appl. Publ. No. WO 94/17178.
Eur. Pat. Appl. Publ. No. EP0273085.
Eur. Pat. Appl. Publ. No. EP0320308.
Eur. Pat. Appl. Publ. No. EP0329822.
Great Britain Patent No. GB2202328.

Afione, Conrad, Kearns, Chunduru, Adams, Reynolds, Guggino, Cutting, Carter, Flotte, "In vivo model of adeno-associated virus vector persistence and rescue," *J. Virol.*, 70(5):3235–41, 1996.

Akashi, Hachiya, Paquette, Osawa, Suzuki, "Irradiation increases manganese superoxide dismutase mRNA levels in human fibroblasts. Possible mechanisms for its accumulation," *J. Biol. Chem.*, 270(26):15864–9, 1995.

Allen and Choun, "Large Unilamellar Liposomes with Low Uptake into the Reticuloendothelial System," *FEBS Lett.*, 223:42–46, 1987.

Anderson, "Human Gene Therapy," *Science*, 256, 808–813, 1992.

Andrews, N. C. and Faller, D. V., (1991) A rapid micro-preparation technique for extraction of DNA-binding proteins from limiting numbers of mammalian cells. *Nucleic Acids Res*, 19, 2499.

Armitage et al., *Proc. Natl. Acad. Sci. USA*, 94(23):12320–12325, 1997.

Armstrong and Emerson, "Transcription of chromatin" these are complex times," *Curr. Opin. Genet. Dev.*, 8(2):165–172, 1998.

Bachmann and Knust, "Dissection of cis-regulatory elements of the drosophila gene serrate," *Gene Dev. Evol.*, 208(6):346–351, 1998.

Balazsovits et al., "Analysis of the effect of liposome encapsulation on the vesicant properties, acute and cardiac toxicities, and antitumor efficacy of doxorubicin," *Cancer Chemother. Pharmacol.*, 23:81–86, 1989.

Bahnemann, "Inactivation of viral antigens for vaccine preparation with particular reference to the application of binary ethylenimine," *Vaccine*, 8(4):299–303, 1990.

Baker, K., Marcus, C. B., Huffman; K., Kruk, H., Malfroy, B., and Doctrow, S. R. (1998) Synthetic combined superoxide dismutase/catalase mimetics are protective as a delayed treatment in a rat stroke model: a key role for reactive oxygen species in ischemic brain injury, *J Pharmacol Exp Ther*, 284(1),215–21.

Bate and Twell, "Functional architecture of a late pollen promoter: pollen-specific transcription is developmentally regulated by multiple stage-specific and co-dependent activator elements," *Plant Mol. Biol.*, 37(5):859–869, 1998.

Bedzyk, Weidner, Denzin, Johnson, Hardman, Pantoliano, Asel, Voss Jr., "Immunological and structural characterization of a high affinity anti-fluorescein single-chain antibody," *J. Biol. Chem.*, 265(30):18615–20, 1990.

Bennett, Cox, Hoeffler, "Fusion of green fluorescent protein with the Zeocin-resistance marker allows visual screening and drug selection of transfected eukaryotic cells," *Biotechniques*, 24(3):478–482, 1998.

Bensmail, Quillet, Petit, Barray and Guespin-Michel, "Regulation of the expression of a gene encoding beta-endoglucanase secreted by *Myxococcus xanthus* during growth: role of genes involved in developmental regulation", *Res. Microbiol.*, 149(5):319–326, 1998.

Benvenisty and Neshif, "Direct introduction of genes into rats and expression of the genes," *Proc Natl Acad Sci USA.*, 83(24): 9551–9555, 1986.

Berns and Giraud, "Adenovirus and adeno-associated virus as vectors for gene therapy," *Ann. N. Y. Acad. Sci.*, 772:95–104, 1995.

Blacklow, Hoggan, Rowe, "Isolation of adenovirus-associated viruses from man," *Proc. Natl. Acad. Sci. USA*, 58(4):1410–5, 1967.

Blacklow, Hoggan, Rowe, "Serologic evidence for human infection with adenovirus-associated viruses," *J. Natl. Cancer Inst.*, 40(2):319–27, 1968.

Blacklow, Hoggan, Sereno, Brandt, Kim, Parrott, Chanock, "A seroepidemiologic study of adenovirus-associated virus infection in infants and children," *Am. J. Epidemiol.*, 94(4):359–66, 1971.

Blackwood and Kadonaga, "Going the distance: a current view of enhancer action," *Science*, 281(5373):61–63, 1998.

Boffa, Carpaneto, Allfrey, *Proc. Natl. Acad. Sci. USA*, 92:1901–1905, 1995.

Boffa, Morris, Carpaneto, Louissaint, Allfrey, *J. Biol. Chem.*, 271:13228–13233, 1996.

Bolivar, Rodriguez, Betlach, Boyer, "Construction and characterization of new cloning vehicles. 1. Ampicillin-resistant derivatives of the plasmid pMB9,"*Gene*, 2(2):75–93, 1977.

Borrello, De Leo, Landriscina, Palazzotti, Galeotti, "Diethyldithiocarbamate treatment up regulates manganese superoxide dismutase gene expression in rat liver," *Biochem. Biophys. Res. Commun.*, 220(3):546–52, 1996.

Brenner, "Human somatic gene therapy: progress and problems," *J. Intern. Med.*, 237(3):229–239, 1995.

Callis, J., Fromm, M., & Walbot, V. (1987) Introns increase gene expression in cultured maize cells. *Genes Dev*, 1, 1183–1200.

Capecchi, M. R., "High efficiency transformation by direct microinjection of DNA into cultured mammalian cells," *Cell* 22(2):479–488, 1980.

Carlsson et al., *Nature*, 380:207, 1996.

Casey, Lo-Hsuch, Lopez, Volgelstein, Stanbridge, "Growth suppression of human breast cancer cells by the introduction of a wild-type p53 gene," *Oncogene*, 6(10):1791–7, 1991.

Cech and Brehm, "Replication of the extrachromosomal ribosomal RNA genes of *Tetrahymena thermophilia*," *Nucleic Acids Res.*, 9(14):3531–43, 1981.

Cech, Zaug, Grabowski, "In vitro splicing of the ribosomal RNA precursor of Tetrahymena: involvement of a guanosine nucleotide in the excision of the intervening sequence," *Cell*, 27(3 Pt 2):487–96, 1981.

Chang, Nunberg, Kaufman, Erlich, Schimke, Cohen, "Phenotypic expression in *E. coli* of a DNA sequence coding for mouse dihydrofolate reductase," *Nature*, 275(5681):617–624, 1978.

Chang et al., "Foreign gene delivery and expression in hepatocytes using a hepatitis B virus vector,"*Hepatology*, 14:134A, 1991.

Chaudhary, Batra, Gallo, Willingham, FitzGerald, Pastan, "A rapid method of cloning functional variable-region antibody genes in *Escherichia coli* as single-chain immunotoxins," *Proc. Natl. Acad. Sci. USA*, 87(3):1066–70, 1990.

Chen and Okayama, "High-efficiency transfection of mammalian cells by plasmid DNA," *Mol. Cell Biol.*, 7:2745–2752, 1987.

Cheung, Hoggan, Hauswirth, Berns. "Integration of the adeno-associated virus genome into cellular DNA in latently infected human Detroit 6 cells," *J. Virol.*, 33(2):739–748, 1980.

Chomczynski, P., and Sacchi, N. (1987) Single-step method of RNA isolation by acid guanidinium thiocyanate-phenol-chloroform extraction. *Anal Biochem*, 162, 156–159.

Chow, Plumb, Wen, Sohn, Lu, Zhang, Lukacs, Tanswell, Hui, Buchwald, Hu, "Development of an epithelium-specific expression cassette with human DNA regulatory elements for transgene expression in lung airways," *Proc. Natl. Acad. Sci. USA*, 94(26):14695–14700, 1997.

Christensen et al., *J. Pept. Sci.*, 1(3):175–183, 1995.

Church, "Manganese superoxide dismutase: nucleotide and deduced amino acid sequence of a cDNA encoding a new human transcript," *Biochim. Biophys. Acta*, 1087(2):250–2, 1990.

Clapp, D. W., "Somatic gene therapy into hematopoietic cells. Current status and future implications," *Clin. Perinatol.*, 20(1):155–168, 1993.

Coffin, "Retroviridae and their replication," *In: Virology*, Fields et al. (eds.), New York: Raven Press, pp. 1437–1500, 1990.

Corey, *Trends Biotechnol.*, 15(6):224–229, 1997.

Conrad, Allen, Afione, Reynolds, Beck, Fee-Maki, Barrazza-Ortiz, Adams, Askin, Carter, Guggino, Flotte, "Safety of single-dose administration of an adeno-associated virus (AAV)-CFTR vector in the primate lung," *Gene Ther.*, 3(8):658–68, 1996.

Couch et al., "Immunization with types 4 and 7 adenovirus by selective infection of the intestinal tract," *Am. Rev. Resp. Dis.*, 88:394–403, 1963.

Coupar et al., "A general method for the construction of recombinant vaccinia virus expressing multiple foreign genes," *Gene*, 68:1–10, 1988.

Couvreur et al., "Nanocapsules, a New Lysosomotropic Carrier," *FEBS Lett.*, 84:323–326, 1977.

Couvreur, "Polyalkyleyanoacrylates as Colloidal Drug Carriers," *Crit. Rev. Ther. Drug Carrier Syst.*, 5:1–20, 1988.

Curiel, D. T., Agarwal, S., Wagner, E., and Cotten, M., "Adenovirus enhancement of transferrin-polylysine-mediated gene delivery," *Proc. Natl. Acad. Sci. USA* 88(19):8850–8854, 1991.

Day and Tuite, "Post-transcriptional gene regulatory mechanisms in eukaryotes: an overview," *J. Endocrinol.*, 157 (3):361–371, 1998.

Del Maestro, R., and McDonald, W. (1989) Subcellular localization of superoxide dismutases, glutathione peroxidase and catalase in developing rat cerebral cortex. *Mech Aging Dev* 48(1), 15–31.

Delort and Capecchi, "TAXI/UAS: a molecular switch to control expression of genes in vivo," *Hum. Gen. Ther.*, 7:809–820, 1996.

Dougall and Nick, *Endocrinology*, 129(5):2376–84, 1991.

Dubensky et al., "Direct transfection of viral and plasmid DNA into the liver or spleen of mice," *Proc. Nat. Acad. Sci. USA*, 81:7529–7533, 1984.

Dueholm et al., *J. Org. Chem.*, 59:5767–5773, 1994.

Eastgate, J., Moreb, J., Nick, H. S., Suzuki, K., Taniguchi, N., & Zucali, J. R. (1993) A role for manganese superoxide dismutase in radioprotection of hematopoeitic stem cells by interleukin-1. *Blood*, 81, 639–646.

Egholm et al., *Nature*, 365:566–568, 1993.

Eglitis, M. A., and Anderson, W. F., "Retroviral vectors for introduction of genes into mammalian cells," *Biotechniques* 6(7):608–614, 1988.

Eglitis, M. A., Kantoff, P. W., Kohn, D. B., Karson, E., Moen, R. C., Lothrop, C. D., Blaese, R. M., and Anderson, W. F., "Retroviral-mediated gene transfer into hemopoietic cells," *Adv. Exp. Med. Biol.*, 241:19–27, 1988a.

Fani, Gallo, Fancelli, Mori, Tamburini, Lazcano, "Heterologous gene expression in an *escherichia coli* population under starvation stress conditions," *J. Mol. Evol.*, 47(3):363–368, 1998.

Fechheimer et al., "Transfection of mammalian cells with plasmid DNA by scrape loading and sonication loading," *Proc. Natl. Acad. Sci. USA*, 84:8463–8467, 1987.

Ferkol et al., *FASEB J.*, 7:1081–1091, 1993.

Fiers, Contreras, Haegemann, Rogiers, Van de Voorde, Van Heuverswyn, Van Herreweghe, Volckaert, Ysebaert, "Complete nucleotide sequence of SV40 DNA," *Nature*, 273(5658):113–120, 1978.

Finke, Trojaneck, Lefterova, Csipai, Wagner, Kircheis, Neubauer, Huhn Wittig, Schmidt-Wolf, "Increase of proliferation rate and enhancement of antitumor cytotoxicity of expanded human CD3!+ CD56!+ immunologic effector cells by receptor-mediated transfection with the interleukin-7 gene," *Gene Therapy*, 5(1):31–39, 1998.

Flotte, Solow, Owens, Afione, Zcitlin, Carter, "Gene expression from adeno-associated virus vectors in airway epithclial cells," *Am. J. Respir. Cell Mol. Biol.*, 7(3):349–56, 1992.

Flotte, Afione, Conrad, McGrath, Solow, Oka, Zeitlin, Gugino, Carter, "Stable in vivo expression of the cystic fibrosis transmembrane conductance regulator with an adeno-associated virus vector," *Proc. Natl. Acad. Sci. USA*, 90(22):10613–7, 1993.

Footer, Engholm, Kron, Coull, Matsudaira, *Biochemistry*, 35:10673–10679, 1996.

Forster and Symons, "Self-cleavage of plus and minus RNAs of virusoid and a structural model for the active sites," *Cell*, 49(2):211–20, 1987.

Fraley et al., "Entrapment of a bacterial plasmid in phospholipid vesicles: Potential for gene transfer," *Proc. Nat'l Acad. Sci. USA*, 76:3348–3352, 1979.

Fried, M. G. and Crothers, D. M., (1981) Equilibria and kinetics of lac repressor-operator interactions by polyacrylamide gel electrophoresis *Nucleic Acids Res*, 9, 6505–6525.

Friedmann, "Progress toward human gene therapy," *Science*, 244:1275–1281, 1989.

Frohman, PCR Protocols, a Guide to Methods and Applications XVIII Ed., Academic Press, 1990.

Fromm, M., Taylor, L. P., and Walbot, V., "Expression of genes transferred into monocot and dicot plant cells by electroporation," *Proc. Natl. Acad. Sci. USA*, 82(17): 5824–5828, 1985.

Fujii, J., and Taniguchi, N. (1991) Phorbol ester induces manganese-superoxide dismutase in tumor necrosis factor-resistant cells. *JBiol Chem* 266, 23142–6.

Fynan, E. F., Webster, R. G., Fuller, D. H., Haynes, J. R., Santoro, J. C., and Robinson, H. L., "DNA vaccines: protective immunizations by parenteral, mucosal, and gene gun inoculations," *Proc. Natl. Acad. Sci. USA* 90(24):11478–11482, 1993.

Gabizon and Papahadjopoulos, "Liposomes formulations with prolonged circulation time in blood and enhanced uptake by tumors," *Proc. Natl. Acad. Sci. USA*, 85:6949–6953, 1988.

Gambacorti-Passerini et al., *Blood*, 88:1411–1417, 1996.

Gefter et al., "A simple method for polyethylene glycol-promoted hybridization of mouse myeloma cells," *Somatic Cell Genet.*, 3(2): 231–236, 1977.

Ghosh-Choudhury et al "Protein IX, a minor component of the human adenovirus capsid, is essential for the packaging of full-length genomes," *EMBO J.*, 6:1733–1739, 1987.

Ghosh and Bachhawat, "Targeting of liposomes to hepatocytes," In: Wu G. and C. Wu ed. Liver diseases, targeted diagnosis and therapy using specific receptors and ligands. New York: Marcel Dekker, pp. 87–104, 1991.

Goding, "Monoclonal Antibodies: Principles and Practice," 2nd Edition, Academic Press, Orlando, Fla., pp. 60–74, 1986.

Goeddel, Heyneker, Hozumi, Arentzen, Itakura, Yansura, Ross, Miozzari, Crea, Seeburg, "Direct expression in *Escherichia coli* of a DNA sequence for human growth hormone," *Nature*, 281(5732):544–548, 1979.

Goeddel, Shepard, Yelverton, Leung, Crea, Sloma, Pestka, "Synthesis of human fibroblast interferon by *E. coli*," *Nucl. Acids Res.*, 8(18):4057–4074, 1980.

Goldstein and Doi, "Prokaryotic promoters in biotechnology," *Biotechnol. Annu. Rev.*, 1:105–128, 1995.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Good and Nielsen, *Antisense Nucleic Acid Drug Dev.*, 7(4):431–437, 1997.

Goodman, Xiao, Donahue, Moulton, Miller, Walsh, Young, Samulski, Nienhuis, "Recombinant adeno-associated virus-mediated gene transfer into hematopoietic progenitor cells," *Blood*, 84(5):1492–1500, 1994.

Gopal, "Gene transfer method for transient gene expression, stable transfection, and cotransfection of suspension cell cultures," *Mol. Cell Biol.*, 5:1188–1190, 1985.

Gossen and Bujard, "Tight control of gene expression in mammalian cells by tetracycline-responsive promoters," *Proc. Natl. Acad. Sci. USA*, 89(12):5547–5551, 1992.

Graham and Prevec, "Manipulation of adenovirus vector." In: E. J. Murray (ed.), Methods in Molecular Biology: Gene Transfer and Expression Protocol, Clifton, N.J.: Humana Press, 7:109–128, 1991.

Graham and Prevec, "Adenovirus-based expression vectors and recombinant vaccines," *Biotechnology*, 20:363–90, 1992.

Graham and van der Eb, "Transformation of rat cells by DNA of human adenovirus 5," *Virology*, 54(2):536–539, 1973.

Graham et al., "Characteristics of a human cell line transformed by DNA from human adenovirus type 5", *J. Gen. Virol.*, 36:59–72, 1977.

Griffith et al., *J. Am. Chem. Soc.*, 117:831–832, 1995.

Grunhaus and Horwitz, "Adenovirus as cloning vector," *Seminar in Virology*, 3:237–252, 1992.

Gwinner et al., *Kidney Int.*, 48(2):354–62, 1995.

Haaima, Lohse, Buchardt, Nielsen, *Angew. Chem. Int. Ed. Engl.*, 35:1939–1942, 1996.

Halliwell, B. & Gutteridge, J. M. (1990) Role of free radicals and catalytic metal ions in human disease: An overview. *Meth in Enzymol. Part B) Oxygen radicals in biological systems*, pp.1–85.

Hanvey et al., *Science*, 258:1481–1485, 1992.

Harland & Weintraub, "Translation of mammalian mRNA injected into Xenopus oocytes is specifically inhibited by antisense RNA," *J. Cell Biol.*, 101: 1094–1099, 1985.

Harlow, E. and Lane, D. "Antibodies: A Laboratory Manual," Cold Spring Harbor Laboratory, Cold Spring Harbor, N.Y., 1988.

Harris, C. A., Derbin, K. S., Hunte McDonough, B., Krauss, M. R., Chen, K. T., Smith, D. M. and Epstein, L. B. (1991) Manganese superoxide dismutase is induced by IFN-gamma in multiple cell types. Synergistic induction by IFN-gamma and tumor necrosis factor or IL-1, *J Immunol* 147, 149–54.

Heath et al., "Liposome-mediate delivery of pteridine antifolates to cells in vitro: potency of methotrexate, and its a and y substituents," *Biochem. Biophys. Acta*, 862:72–80, 1986.

Hermonat and Muzycska, "Use of adenoassociated virus as a mammalian DNA cloning vector: Transduction of neomycin resistance into mammalian tissue culture cells," *Proc. Natl Acad. Sci. USA*, 81(20):6466–6470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol-clearance in normal mice," *Proc. Natl. Acad. Sci. USA* 90:2812–2816, 1993.

Hesdorffer, Ayello, Ward, Kaubisch, Vahdat, Balmaceda, Garrett, Fetell, Reiss, Bank, Antman, "Phase I trial of retroviral-mediated transfer of the human MDR1 gene as marrow chemoprotection in patients undergoing high-dose chemotherapy and autologous stem-cell transplantation." *J. Clin. Oncol.*, 16(1):165–172, 1998.

Hess, Boiteux, Kruger, "Cooperation of glycolytic enzymes," *Adv. Enzyme Regul.*, 7:149–167, 1969.

Hettwer, Jackel, Boch, Meyer, Ulrich, "Cloning, nucleotide sequence, and expression in *escherichia coli* of levansucrase genes from the plant pathogens *pseudomonas syringae* pv. glycinea and *P. syringae* pv. phaseolicola," *Appl. Environ. Microbiol.*, 64(9):3180–3187, 1998.

Hitzeman, Clarke, Carbon, "Isolation and characterization of the yeast 3-phosphoglycerokinase gene (PGK) by an immunological screening technique," *J. Biol. Chem.*, 255 (24):12073–12080, 1980.

Hoggan, "Adneovirus associated viruses," *Prog. Med. Virol.*, 12:211–39, 1970.

Hollstein, Sidranksy, Vogelstein, Harris, "p53 mutations in human cancers," *Science*, 253(5015):49–53, 1991.

Horwich et al. "Synthesis of hepadenovirus particles that contain replicationefective duck hepatitis B virus genomes in cultured HuH7 cells," *J. Virol.*, 64:642–650, 1990.

Hurt, J., Hsu, J. L., Dougall, W. C., Visner, G. A., Burr, I. M., & Nick, H. S. (1992) Multiple mRNA species generated by alternate polyadenylation from the rat manganese superoxide dismutase gene, *Nucleic Acids Res*, 20, 2985–2990.

Hwang, Kaiser, Anderson, "Development of a conditional self-inactivating (C-SIN) retroviral vector for liver-directed gene expression," Hepatology, 26(4 Pt 2):195A, 1997.

Hyrup and Nielsen, *Bioorg. Med. Chem.*, 1996.

Imaizumi et al., "Liposome-entrapped superoxide dismutase ameliorates infarct volume in focal cerebral ischemia," *Acta Neurochurgia Suppl.* 51:236–239, 1990.

Imaizumi et al., "Liposome-entrapped superoxide dismutase reduces cerebral infarction in cerebral ischemia in rats," *Stroke*, 21:1312–1317, 1990. Jensen et al., *Biochemistry*, 36(16):5072–5077, 1997.

Itakura, Hirose, Crea, Riggs, Heyneker, Bolivar, Boyer, "Expression in *Escherichia coli* of a chemically synthesized gene for the hormone somatostatin," *Science*, 198 (4321):1056–1063, 1977.

Jaenisch, "Transgenic animals," *Science*, 240(4858): 1468–1474, 1988.

Johnston, S. A., and Tang, D. C., "Gene gun transfection of animal cells and genetic immunization," *Methods Cell. Biol.* 43(A):353–365, 1994.

Jones, "Proteinase mutants of *Saccharomyces cerevisiae*," *Genetics*. 85(1):23–33, 1977.

Jones and Shenk, "Isolation of deletion and substitution mutants of adenovirus type 5," *Cell*, 13:181–188, 1978.

Jones, P. L., Dongsbeng, P and Boss, J. M. (1997) Tumor necrosis factor alpha and interleukin-1β regulate the murine manganese superoxide dismutase gene through a complexintronic enhancer involving C/EPB-β and NF-κB. *Mol Cell Biol.*, 17, 6970–6981.

Joyce and Inoue, "Structure of the catalytic core of the Tetrahymena ribozyme as indicated by reactive abbreviated forms of the molecule," *Nucleic Acids Res.*, 15(23): 9825–40, 1987.

Judde, J. & Max, E. E. (1992) Characterization of the human immunoglobulin kappa gene 3" enhancer: functional importance of three motifs that demonstrate B-cell-specific in vivo footprints, *Mol Cell Biol*, 12, 5206–5216.

Kaneda et al., "Introduction and expression of the human insulin gene in adult rat liver," *J Biol Chem.*, 264(21): 12126–12129, 1989.

Kaplitt, Leone, Samulski, Xiao, Pfaff, O'Malley, During, "Long-term gene expression and phenotypic correction using adeno-associated virus vectors in the mammalian brain," *Nat. Genet.*, 8(2):148–54, 1994.

Karlsson et al., *EMBO J.*, 5:2377–2385, 1986.

Kato et al., "Expression of hepatitis β virus surface antigen in adult rat liver," *J. Biol. Chem.*, 266:3361–3364, 1991.

Kessler, Podsakoff, Chen, McQuiston, Colosi, Matelis, Kurtzran, Byrne, "Gene delivery to skeletal muscle results in sustained expression and systemic delivery of a therapeutic protein," *Proc. Natl. Acad. Sci. USA*, 93(24): 14082–7, 1996.

Kifle et al., *J. Neurochem*, 66(5):2128–35, 1996.

Kim and Cech, "Three-dimensional model of the active site of the self-splicing rRNA precursor of Tetrahymena," *Proc. Natl. Acad. Sci. USA*, 84(24):8788–92, 1987.

Kingsman, Clarke, Mortimer, Carbon, "Replication in *Saccharomyces cerevisiae* of plasmid pBR313 carrying DNA from the yeast trpl region," *Gene*, 7(2):141–152, 1979.

Klein et al., "High-velocity microprojectiles for delivering nucleic acids into living cells," *Nature*, 327:70–73, 1987.

Koch et al., *Tetrahedron Lett.*, 36:6933–6936, 1995.

Kohler and Milstein, *Eur. J. Immunol.*, 6:511–519, 1976.

Kohler and Milstein, *Nature*, 256:495–497, 1975.

Koike, "Cloning, structure, chromosomal localization and promoter analysis of human 2-oxoglutarate dehydrogenase gene," *Biochem. Biophys. Acta*, 1385(2):373–384, 1998.

Koppelhus, *Nucleic Acids Res.*, 25(11):2167–2173, 1997.

Kremsky et al., *Tetrahedron Lett.*, 37:4313–4316, 1996.

Kriegler, M. (1990) DNA Transfer. In *Gene Transfer and Expression: A Laboratory Manual*, pp. 96–100.

Kuby, J., *Immunology 2nd Edition*, W. H. Freeman & Company, N.Y., 1994

Kunkel et al., *Methods Enzymol.*, 154:367–3892, 1987.

Kyte and Doolittle, "A simple method for displaying the hydropathic character of a protein," *J. Mol. Biol.*, 157(1): 105–32, 1982.

Landsdorp et al., *Hum. Mol. Genet.*, 5:685–691, 1996.

Larsson and Litwin, "The growth of polio virus in human diploid fibroblasts grown with cellulose microcarriers in suspension cultures," *Dev. Biol. Stand.*, 66:385–90, 1987.

Le Gal La Salle et al., "An adenovirus vector for gene transfer into neurons and glia in the brain," *Science*, 259:988–990, 1993.

Levrero et al., "Defective and nondefective adenovirus vectors for expressing foreign genes in vitro and in vivo," *Gene*, 101:195–202, 1991.

Li, Y., Huang, T-T., Carlson, E. J., Melov, S., Ursell, P. C., Olson, J. L., Noble, L. J., Yoshimura, M. P., Berger, C., Chan, P. H., Wallace, D. C., and Epstein, C. J. (1995) Dilated cardiomyopathy and neonatal lethality in mutant mice lacking manganese superoxide dismutase. *Nature Genetics*, 11, 376–381.

Lim, *J. Pharm. Sci.*, 70(4):351–4, 1981.

Lu, L., Xiao, M., Clapp, D. W., Li, Z. H., and Broxmeyer, H. E., "High efficiency retroviral mediated gene transduction into single isolated immature and replatable CD34(3+) hematopoietic stem/progenitor cells from human umbilical cord blood," *J. Exp. Med.* 178(6): 2089–2096, 1993.

Macejak and Saenow, "Internal initiation of translation mediated by the 5□ leader of a cellular mRNA," *Nature*, 353:90–94, 1991.

Maloy et al., "Microbial Genetics" 2nd Edition. Jones and Bartlett Publishers, Boston, Mass., 1994.

Manganaro, F., Chopra, V. S., Mydlarski, M. B., Bernatchez, G., and Schipper, H. M. (1995) Redox perturbations in cysteamine-stressed astroglia: implications for inclusion formation and gliosis in the aging brain. *Free Radio Biol Med*, 19(6),823–35.

Mann et al., "Construction of a retrovirus packaging mutant and its use to produce helper-free defective retrovirus," *Cell*, 33:153–159, 1983.

Markowitz et al., "A safe packaging line for gene transfer: Separating viral genes on two different plasmids," *J. Virol.*, 62:1120–1124, 1988.

Massie, Couture, Lamoureux, Mosser, Guilbault, Jolicoeur, Belanger, Langelier, "Inducible overexpression of a toxic protein by an adenovirus vector with a tetracycline-regulatable expression cassette," *J. Virol.*, 72(3): 2289–2296, 1998.

Melov, S., Schneider, J. A., Day, B. J., Hinerfeld, D., Coskun, P., Mirra, S. S., Crapo, J. D., Wallace, D. C. (1998) A novel neurological phenotype in mice lacking mitochondrial manganese superoxide dismutase. *Nature Genetics*, 18, 159–163.

Meyrick, B., & Magnuson, M. A. (1994) Identification and functional characterization of the bovine manganous superoxide dismutase promoter. *Am J Respir Cell Mol Biol*, 10, 113–121.

Michel and Westhof, "Modelling of the three-dimensional architecture of group 1 catalytic introns based on comparative sequence analysis," *J. Mol. Biol.*, 216(3): 585–610, 1990.

Michael, *Biotechniques*, 16:410–412, 1994.

Mizrahi and Van Wezel, In: *Advances in Biotechnological Processes*, Vol. 2, New York, N.Y. 1983.

Mollegaard, Buchardt, Egholm, Nielsen, *Proc. Natl. Acad. Sci. USA*, 91:3892–3895, 1994.

Mulligan, "The Basic Science of Gene Therapy," *Science*, 260:926–932, 1993.

Muzyczka, "Use of adeno-associated virus as a general transduction vector for mammalian cells," *Curr. Top Microbiol. Immunol.*, 158:97–129, 1992.

Namba, Tagawa, Iwadate, Kimura, Sueyoshi, Sakiyama, "Bystander effect-mediated therapy of experimental brain tumor by genetically engineered tumor cells [see comments]," *Hum. Gene Ther.*, 9(1):5–11, 1998.

Neilsen, In: *Perspectives in Drug Discovery and Design* 4, Escom Science Publishers, pp. 76–84, 1996.

Nicolas and Rubinstein, "Retroviral vectors," In: *Vectors: A survey of molecular cloning vectors and their uses*, Rodriguez and Denhardt (eds.), Stoneham: Butterworth, pp. 494–513, 1988.

Nicolau and Sene, "Liposome-mediated DNA transfer in eukaryotic cells," *Biochem. Biophys. Acta*, 721:185–190, 1982.

Nicolau et al., "Liposomes as carriers for in vivo gene transfer and expression," *Methods Enzymol.*, 149:157–176, 1987.

Nielsen, Kahn, Duell, Weier, Taylor, Young, "Apolipoprotein B gene expression in a series of human apolipoprotein B transgenic mice generated with recA-assisted restriction endonuclease cleavage-modified bacterial artificial chromosomes. An intestine-specific enhancer element is located between 54 and 62 kilobases 5' to the structural gene," *J. Biol Chem.*, 273(34):21800–21807, 1998.

Nielsen, P. E., Egholm, M., Berg, R. H., and Buchardt, O, "Peptide nucleic acids (PNAs): Potential antisense and anti-gene agents," *Anti-Cancer Drug Design*, 8(1):53–63, 1993.

Nielsen, P. E., Egholm, M., Berg, R. H., and Buchardt, O, "Sequence-selective recognition of DNA by strand displacement with a thymine-substituted polyamide," *Science* 254, 1497–1500, 1991.

Nilsson and Mosbach, "Immobilized animal cells," *Dev. Biol. Stand.*, 66:183–93, 1987.

No, Yao, Evans, "Ecdysone-inducible gene expression in mammalian cells and transgenic mice," *Proc. Nat. Acad. Sci. USA*, 93:3346–3351, 1996.

Norton, Piatyszek, Wright, Shay, Corey, *Nat. Biotechnol.*, 14:615–620, 1996.

Norton, Waggenspack, Varnum, Corey, *Bioorg. Med. Chem.*, 3:437–445, 1995.

Ohara et al., *Proc. Natl. Acad. Sci. USA*, 86(15):5673–5677, 1989.

Orum, Nielsen, Egholm, Berg, Buchardt, Stanley, *Nucl. Acids Res.*, 21:5332–5336, 1993.

Orum, Nielsen, Jorgensen, Larsson, Stanley, Koch, *BioTechniques*, 19:472–480, 1995.

Pardridge, Boado, Kang, *Proc. Natl. Acad. Sci. USA*, 92:5592–5596, 1995.

Paskind et al., "Dependence of moloney murine leukemia virus production on cell growth," *Virology*, 67:242–248, 1975.

Pelletier and Sonenberg, "Internal initiation of translation of eukaryotic mRNA directed by a sequence derived from poliovirus RNA," *Nature*, 334:320–325, 1988.

Perales et al., *Proc. Natl. Acad. Sci. USA*, 91:4086–4090, 1994.

Perera, St. Clair, McClain, "Differential regulation of manganese superoxide dismutase activity by alcohol and TNF in human hepatoma cells," *Arch. Biochem. Biophys.*, 323(2):471–6, 1995.

Perrimon, "New advances in Drosophilia provide opportunities to study gene function," *Proc. Natl. Acad. Sci.*, 95(17):9716–9717, 1998.

Perry-O'Keefe, Yao, Coull, Fuchs, Egholm, *Proc. Natl. Acad. Sci. USA*, 93:14670–14675, 1996.

Petersen, Jensen, Egholm, Nielsen, Buchardt, *Bioorg. Med. Chem. Lett.*, 5:1119–1124, 1995.

Petricciani, "Should continuous cell lines be used as substrates for biological products?" *Dev. Biol. Stand.*, 66:3–12, 1987.

Potter et al., "Enhancer-dependent expression of human k immunoglobulin genes introduced into mouse pre-B lymphocytes by electroporation," *Proc. Natl. Acad. Sci. USA*, 81:7161–7165, 1984.

Prokop, A., and Bajpai, R. K. "Recombinant DNA Technology I" *Ann. N. Y. Acad. Sci.* Vol. 646, 1991.

Proud and Denton, "Molecular mechanisms for the control of translation by insulin," *Biochem. J.*, 328(Pt. 2):329–341, 1997.

Ptashne, M. (1986) Gene regulation by proteins acting nearby and at a distance, *Nature*, 322, 697–701.

Queen, C. & Baltimore, D. (1983) Immunoglobulin gene transcription is activated by downstream sequence elements, *Cell*. 33, 741–748.

Racher et al., *Biotechnology Techniques*, 9:169–174, 1995.

Ragot et al "Efficient adenovirus-mediated transfer of a human minidystrophin gene to skeletal muscle of mdx mice," *Nature*, 361:647–650, 1993.

Reeds, Burrin, Davis, Stoll, "Amino acid metabolism and the energetics of growth," *Arch. Tierernahr.*, 51(2–3): 187–197, 1998.

Reinhold-Hurek and Shub, "Self-splicing introns in tRNA genes in widely divergent bacteria," *Nature*, 357(6374): 173–6, 1992.

Renan, "Cancer genes: current status, future prospects, and applicants in radiotherapy/oncology," *Radiother. Oncol.*, 19:197–218, 1990.

Rhodes and Oshima, "A regulatory element of the human keratin 18 gene with AP-1-dependent promoter activity," *J. Biol. Chem.*, 273(41):26534–26542, 1998.

Rich et al., "Development and analysis of recombinant adenoviruses for gene therapy of cystic fibrosis." *Hum. Gene Ther.*, 4:461–476, 1993.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.*, 10:689–695, 1990.

Rose. *Anal. Chem.*, 65(24):3545–3549, 1993.

Rosenfeld et al., "Adenovirus-mediated transfer of a recombinant a1-antitrypsin gene to the lung epithelium in vivo," *Science*, 252:431–434, 1991.

Rosenfeld et al., "In vivo transfer of the human cystic fibrosis transmembrane conductance regulator gene to the airway epithelium," *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Ruskowski et al., *Cancer*, 80(12 Suppl):2699–2705, 1997.

Sachs and Buratowski, "Common themes in translational and transcriptional regulation," *Trends Biochem. Sci.*, 22(6): 189–192, 1997.

Sakonju, S., Bogenhagen, D. F., and Brown, D. D. (1980) A control region in the center of the 5S RNA gene directs specific initiation of transcription: The 5' border of the region. *Cell*, 19, 13–25.

Sambrook, Fristch, Maniatis, "Molecular Cloning: A Laboratory Manual," C. Nolan, ed., Cold Spring Harbor Laboratory Press, Cold Spring Harbor, N.Y., 1989.

Sandig and Strauss, "Liver-directed gene transfer and application to therapy," *J. Mol. Med.* (Berlin), 74(4):205–212, 1996.

Sarver, Cantin, Chang, Zaia, Ladne, Stephens, Rossi, "Ribozymes as potential anti-HIV-1 therapeutic agents," *Science*, 247(4947):1222–1225, 1990.

Sato, Watanabe, Iwashita, "Synthesis and characterization of superoxide dismutase-deferoxamine conjugate via polyoxyethylene: a new molecular device ofr removal of a variety of reactive oxygen species," *Bioconjug. Chem.*, 6(3):249–54, 1995.

Scanlon, Jiao, Funato, Wang, Tone, Rossi, Kashani-Sabet, "Ribozyme-mediated cleavage of c-fos mRNA reduces gene expression of DNA synthesis enzymes and metallothionein," *Proc. Natl. Acad. Sci. USA*, 88(23): 10591–5, 1991.

Segal, In: *Biochemical Calculations*, 2nd Edition. John Wiley & Sons, New York, 1976.

Selden, R. F., Howie, K. B., Rowe, M. E., Goodman, H. M., and Moore, D. D. (1986) Human Growth Hormone as a Reporter Gene in Regulation Studies Employing Transient Gene Expression. *Mol Cell Biol.*, 6, 3173–3179.

Serrano, Hannon, Beach, "A new regulatory motif in cell-cycle control causing specific inhibition of cyclin D/CDK4, " *Nature*, 366(6456):704–7, 1993.

Serrano, Gomez-Lahoz, DePinho, Beach, Bar-Sagi, "Inhibition of ras-induced proliferation and cellular transformation by p16INK4," *Science*, 267(5195):249–52, 1995.

Shields, J. M. and Yang, V. W. (1998) Identification of the DNA sequence that interacts with the Gut-enriched Kruppel-like factor. *Nucleic Acids Res*, 26, 796–802.

Shull, S., Heintz, N. H., Periasamy, M., Manohar, M., Janssen, Y. M., Marsh, J. P., & Mossman, B. T. (1991). Differential regulation of antioxidant enzymes in response to oxidants. *J Biol Chem*, 266, 24398–24403.

Sirnkevich, C. P., Thompson, J. P Poppleton. H., & Raghow, R. (1992) The transcriptional tissue specificity of the human proα1 (I) collagen gene is determined by a negative cis regulatory element in the promoter. *Biochem J*, 286, 179–185.

Srivastava, Lusby, Berns, "Nucleotide sequence and organization of the adeno-associated virus 2 genome," *J. Virol.*, 45(2):555–64, 1983.

Stephanz et al., *Exp. Nephrol*, 4(3):151–8, 1996.

Stetsenko, Lubyako, Potapov, Azhikina, Sverdlov, *Tetrahedron Lett.*, 37:3571–3574, 1996.

Stinchcomb, Struhl, Davis, "Isolation and characterization of a yeast chromosomal replicalor," *Nature*, 282(5734): 39, 1979.

Stratford-Perricaudet and Perricaudet, "Gene transfer into animals: the promise of adenovirus," p. 51–61, In: *Human Gene Tranfer*, Eds, O. Cohen-Haguenauer and M. Boiron, Editions John Libbey Eurotext, France, 1991.

Stratford-Perricaudet et al., "Evaluation of the transfer and expression in mice of an enzyme-encoding gene using a human adenovirus vector," *Hum. Gene Ther.*, 1:241–256, 1990.

Sullenger, "Revising messages traveling along the cellular information superhighway," *Chem. Biol.*, 2(5):249–253, 1995.

Suzuki, Takahashi, Kuroishi, Suyama, Ariyoshi, Takahashi, Ueda, "p53 mutations in non-small cell lung cancer in Japan: association between mutations and smoking," *Cancer Res.*, 52(3):734–6, 1992.

Suzuki, K., Tatsumi, H., Satoh, S., Senda, T., Nakata, T., Fujii, J., and Taniguchi, N. (1993) Manganese-superoxide dismutase in endothelial cells: localization and mechanism of induction. *Am J Physiol* 265(4 Pt 2), H1173-8.

Takimoto, Y. & Kuramoto, A. (1993) Presence of a regulatory element within the first intron of the human platelet-derived growth factor -A chain gene. *Jpn J Cancer Res*, 84, 1268–1272.

Tannahill et al., *Gastroenterology*, 109(3):800–11, 1995.

Temin, "Retrovirus vectors for gene transfer: Efficient integration into and expression of exogenous DNA in vertebrate cell genome." In: *Gene Transfer*, Kucherlapati (ed.), New York: Plenum Press, pp. 149–188, 1986.

Thiede, Bayerdorffer, Blasczyk, Wittig, Neubauer, *Nucleic Acids Res.*, 24:983–984, 1996.

Thisted, Just, Petersen, Hyldig-Nielsen, Godtfredsen, *Cell Vision.* 3:358–363, 1996.

Thomson et al., *Tetrahedron*, 51:6179–6194, 1995.

Tomic et al., *Nucl. Acids Res.*, 12:1656, 1990.

Top et al., "Immunization with live types 7 and 4 adenovirus vaccines, II. Antibody response and protective effect against acute respiratory disease due to adenovirus type 7," *J. Infect. Dis.*, 124:155–160, 1971.

Tschumper and Carbon, "Sequence of a yeast DNA fragment containing a chromosomal replicator and the TRP1 gene," *Gene*, 10(2):157–166, 1980.

Tur-Kaspa et al., "Use of electroporation to introduce biologically active foreign genes into primary rat hepatocytes," *Mol. Cell Biol.*, 6:716–718, 1986.

Ulmann, Will, Breipohl, Langner, Ryte, *Angew. Chem., Int. Ed. Engl.*, 35:2632–2635, 1996.

Upender et al., *Biotechniques*, 18:29–31, 1995.

Valentine and Nick, *Gastroenterology*, 103(3):905–12, 1992.

Valentine et al., *Gastroenterology*, 111 (1):56–64, 1996.

van Holde and Zlatanova, "Chromatin architectural proteins and transcription factors: a structural connection," *Bioessays*, 18(9):697–700, 1996.

Varmus et al., "Retroviruses as mutagens: Insertion and excision of a nontransforming provirus alter the expression of a resident transforming provirus," *Cell*, 25:23–36, 1981.

Veselkov, Demidov, Nielsen, Frank-Kamenetskii, *Nucl. Acids Res.*, 24:2483–2487, 1996.

Vickers, Griffith, Ramasamy, Risen, Freier, *Nucl. Acids Res.*, 23:3003–3008, 1995.

Visner et al., *Biochem Biophys. Res. Commun.*, 188(1):453–62, 1992.

Visner et al., *J. Biol. Chem.*, 265(5):2856–64, 1990.

Visner, G. A., Block, E. R., Burr, I. M., & Nick, H. S. (1991) Regulation of manganese superoxide dismutase in porcine pulmonary artery endothelial cells. *Am J Physiol Lung Cell Mol Physiol*, 260, L444–L449.

Wagner, Plank, Zatloukal, Cotten, Birnstiel, "Influenza virus hemagglutinin HA-2 N-terminal fusogenic peptides augment gene transfer by transferrin-polylysine-DNA complexes: toward a synthetic virus-like gene-transfer vehicle," *Proc. Natl. Acad. Sci. USA*, 89(17):7934–8, 1992a.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," *Proc. Natl. Acad. Sci. USA*, 89(13):6099–6103, 1992b.

Walker et al. *Proc. Natl. Acad. Sci. USA*, 89(1):392–396, 1992.

Walther and Stein, "Targeted vectors for gene therapy of cancer and retroviral infections," *Mol. Biol.*, 6(3):267–286, 1996.

Wang et al., *Cytotechnology*, 9(1–3):41–9, 1992.

Wang, Stacy, Binder, Marin-Padilla, Sharpe, Speck, "Disruption of the Cbfa2 gene causes necrosis and hemorrhaging in the central nervous system and blocks definitive hematopoiesis," *Proc. Natl. Acad. Sci. USA*, 93:3444–3449, 1996a.

Wang, Stacy, Miller, Lewis, Gu, Huang, Bushweller, Bories, Alt, Ryan, Liu, Wynshaw-Boris, Binder, Marin-Padilla, Sharpe, Speck, "The Cbfβ subunit is essential for CBFα2 (AML1) function in vivo," *Cell*, 87:697–708. 1996b.

Watson, J. D. et al., *Molecular Biology of the Gene*, 4th Ed., W. A. Benjamin, Inc., Menlo Park, Calif., 1987.

Warner, Stuart, Gebb, Wispe, "Redox regulation of manganese superoxide dismutase," *Am. J. Physiol.*, 271(1 Pt 1):L150–8, 1996.

Webb and Hurskainen, *J. Biomol. Screen.*, 1:119–121, 1996.

Weinberg, Zaaoli, Kadiwar, Yuspa, "p53 gene dosage modifies growth and malignant progression of keratinocytes expressing the v-rasHa oncogene," *Cancer Res.*, 54(21):5584–92, 1994.

Wettstein, Colombo, Jaenisch, "Non-H2 histocompatibility antigens encoded by Moloney-murine leukemia virus in mov mouse strains are detectable by skin grafting and cytolytic T lymphocytes," *J. Immunol.*, 140(12):4337–4341, 1988.

Wispe, J. R., Warner, B. B., Clark, J. C., Dey, C. R., Neuman, J., Glasser, S. W., Crapo, J. D., Chang, L., & Whitsett, J. A. (1992) Human Mn-superoxide dismutase in pulmonary epithelial cells of transgenic mice confers protection from oxygen injury, *J Biol Chem*, 267, 23937–23941.

Wong et al., "Appearance of β-lactamase activity in animal cells upon liposome mediated gene transfer," *Gene*, 10:87–94, 1980.

Wong, G. H., Elwell, J. Oberly, L & Goeddel, D. V. (1989) Manganous superoxide dismutase is essential for cellular resistance to cytotoxicity by tumor necrosis factor. *Cell*, 58, 923–931.

Wong, G. H. and Goeddel, D. V. (1988) Induction of manganous superoxide dismutase by tumor necrosis factor: possible protective mechanism. *Science*, 242, 941–944.

Wong, T. E and Neumann, E., "Electric field mediated gene transfer," *Biochim. Biophys. Res. Commun.* 107(2):584–587, 1982.

Wu and Wu. "Evidence for targeted gene delivery to HepG2 hepatoma cells in vitro," *Biochemistry* 27:887–892, 1988.

Wu and Wu, "Receptor-mediated in vitro gene transfections by a soluble DNA carrier system," *J. Biol. Chem.*, 262:4429–4432, 1987.

Wu and Wu, *Adv. Drug Delivery Rev.*, 12:159–167, 1993.

Wu, and Dean, "Functional significance of loops in the receptor binding domain of *Bacillus thuringiensis* CryIIIA δ-endotoxin," *J. Mol. Biol.* 255:628–640, 1996.

Yang and Trempe, "Analysis of the terminal repeat binding abilities of mutant adeno-associated virus replication proteins," *J. Virol.*, 67(7):4442–7, 1993.

Yang et al., "In vivo and in vitro gene transfer to mammalian somatic cells by particle bombardment," *Proc. Natl. Acad. Sci. USA*, 87:9568–9572, 1990.

Zaphiropoulos, "Mechanisms of pre-mRNA splicing: classical versus non-classical pathways," *Histol. Histopathol.*, 13(2):585–589, 1998.

Zatloukal, L Wagner, E., Cotten, M., Phillips, S., Plank, C., Steinlein, P., Curiel, D. T., and Bimstiel, M. L., "Transferrinfection: a highly efficient way to express gene constructs in eukaryotic cells," *Ann. N. Y. Acad. Sci.*, 660:136–153, 1992.

Zelenin et al., "High-velocity mechanical DNA transfer of the chloramphenicol acetyltransferase gene into rodent liver, kidney and mammary gland cells in organ explants and in vivo," *FEBS Lett.*, 280:9496, 1991.

Zhang, Olsen, Nguyen, Olson, Rhodes, Mascarenhas, "Expression of eukaryotic proteins in soluble form in *Escherichia coli*," *Protein Expr. Purif.*, 12(2):159–165, 1998.

Zhang, W., Shields, J. M., Sogawa, K., Fujii-Kuriyama, Y., and Yang, V. W. (1998) The Gut-enriched Kruppel-like factor suppresses the activity of the CYP1A1 promoter in a Sp1-dependent fashion. *J Biol Chem*, 273, 17917–17925.

Zhang, N. (1996) Characterization of the 5' flanking region of the human MnSOD gene. *Biochem Biophys Res Comm*, 220, 171–180.

What is claimed is:

1. An isolated polynucleotide comprising a manganese superoxide dismutase regulatory element operably linked to a heterologous polynucleotide, wherein the regulatory element comprises the nucleotide sequence of SEQ ID NO:2, the regulatory element being capable of causing inducible transcription or expression of an operably linked heterologous polynucleotide.

2. An isolated human manganese superoxide dismutase regulatory element consisting of the nucleotide sequence of SEQ NO:2, the regulatory element-being capable of causing inducible transcription or expression of an operably linked heterologous polynucleotide.

3. An isolated regulatory element of claims 2 operably linked to a heterologous polynucleotide so that, upon activation of the regulatory element, transcription or expression of the heterologous polynucleotide is induced.

4. An isolated polynucleotide of claim 1, wherein the heterologous polynucleotide encodes a cytoprotectant.

5. An isolated polynucleotide of claim 1, wherein the heterologous polynucleotide encodes an antisense mRNA.

6. An isolated polynucleotide of claim 1 which induces transcription or expression of an operatively linked heterologous polynucleotide in the presence of an inflammatory stimulus.

7. An isolated polynucleotide of claim 6, wherein the inflammatory stimulus is selected from the group consisting of TNF-α, IL-1β, and LPS.

8. An isolated polynucleotide of claim 1, which induces transcription or expression of an operatively linked heterologous polynucleotide in the presence of 5-aminosalicylic acid.

9. An isolated polynucleotide of claim 1, wherein the regulatory sequence is operatively linked to a promoter sequence.

10. The isolated polynucleotide of claim 9, wherein the promoter is the Herpes simplex thymidine kinase promoter.

11. A cell transformed with an isolated polynucleotide of claim 1.

12. An inducible expression system comprising:
a) an isolated polynucleotide comprising a manganese superoxide dismutase regulatory element operably linked to a heterologous polynucleotide, wherein the regulatory element comprises the nucleotide sequence of SEQ ID NO:2, he regulatory element being capable of causing inducible transcription or expression of the heterologous polynucleotide upon activation; and
b) a compound which activates the regulatory element, or a polynucleotide encoding a compound which activates the regulatory element.

13. The expression system of claim 12 wherein the regulatory element is a human regulatory element.

14. The expression system of claim 12 wherein the compound which activates the regulatory element is an inflammatory mediater.

15. The expression system of claim 14 wherein the mediater which activates the regulatory element is selected from the group consisting of TNF-α, IL-1β, and LPS.

16. The expression system of claim 16 wherein the compound which activates the regulatory element is 5-aminosalicylic acid.

17. The expression system of claim 12 further comprising a promoter operably linked to the regulatory element.

18. A method of producing a polypeptide comprising introducing the expression system of claim 12 into a cell under conditions suitable for expression of the heterologous polypeptide.

19. A method of achieving inducible transcription or expression of a heterologous polynucleotide in a cell, the method comprising introducing into a cell an isolated polynucleotide comprising a manganese superoxide dismutase regulatory element operably linked to a heterologous polynucleotide, wherein the regulatory element comprises the nucleotide sequence of SEQ ID NO:2, the regulatory element being capable of causing inducible transcription or expression of an operably linked heterologous polynucleotide.

20. The method of claim 19 further comprising introducing into the cell an effective amount of a compound which activates the regulatory element to induce transcription or expression of an operatively linked polynucleotide, or a polynucleotide encoding the compound.

21. The method of claim 20 wherein the compound is an inflammatory mediator.

22. The method of claim 21 wherein the compound is selected from the group consisting of TNF-α, IL-1β, and LPS.

23. The method of claim 26 wherein the compound is 5-aminosalicylic acid.

* * * * *